United States Patent
Orimoto et al.

(10) Patent No.: US 9,884,858 B2
(45) Date of Patent: Feb. 6, 2018

(54) DIARYL-AZOLE COMPOUND

(71) Applicant: Sumitomo Chemical Company, Limited, Tokyo (JP)

(72) Inventors: Kohei Orimoto, Takarazuka (JP); Hajime Mizuno, Takarazuka (JP); Yoshihiko Nokura, Takarazuka (JP); Yuji Nakajima, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 15/305,027

(22) PCT Filed: Apr. 21, 2015

(86) PCT No.: PCT/JP2015/062627
§ 371 (c)(1),
(2) Date: Oct. 18, 2016

(87) PCT Pub. No.: WO2015/163478
PCT Pub. Date: Oct. 29, 2015

(65) Prior Publication Data
US 2017/0190696 A1    Jul. 6, 2017

(30) Foreign Application Priority Data

Apr. 24, 2014  (JP) ................. 2014-089864

(51) Int. Cl.
| | | |
|---|---|---|
| C07D 413/04 | (2006.01) |
| A01N 43/32 | (2006.01) |
| C07D 417/14 | (2006.01) |
| A01N 43/82 | (2006.01) |
| C07D 413/14 | (2006.01) |

(52) U.S. Cl.
CPC ........... *C07D 417/14* (2013.01); *A01N 43/82* (2013.01); *C07D 413/04* (2013.01); *C07D 413/14* (2013.01)

(58) Field of Classification Search
None
See application file for complete search history.

(56) References Cited

U.S. PATENT DOCUMENTS

| | | |
|---|---|---|
| 4,414,221 A | 11/1983 | Parsons et al. |
| 5,318,959 A | 6/1994 | Ozaki et al. |
| 6,277,872 B1 | 8/2001 | Brenner et al. |
| 6,413,992 B1 | 7/2002 | Tisdell et al. |
| 2009/0163545 A1 | 6/2009 | Goldfarb |
| 2011/0212949 A1 | 9/2011 | Bretschneider et al. |
| 2014/0194290 A1 | 7/2014 | Takahashi et al. |

FOREIGN PATENT DOCUMENTS

| | | |
|---|---|---|
| CN | 1250049 A | 4/2000 |
| DE | 19643037 A1 | 4/1998 |
| JP | S56154464 A | 11/1981 |
| JP | H02304069 A | 12/1990 |
| JP | H051060 A | 1/1993 |
| JP | H06234751 A | 8/1994 |
| JP | 2000318312 A | 11/2000 |
| JP | 2002528447 A | 9/2002 |
| JP | 2011507910 A | 3/2011 |
| JP | 2011527995 A | 11/2011 |
| WO | 2006069155 A2 | 6/2006 |

OTHER PUBLICATIONS

National Center for Biotechnology Information. PubChem Compound Datatbase; CID=1484135; pp. 1-14; https://pubchem.ncbi.nlm.nih.gov/compound/1484135; retrieved Jul. 11, 2017.*
Int'l Search Report dated Jun. 30, 2015 in Int'l Application No. PCT/JP2015/062627 (English Translation).
Int'l Preliminary Report on Patentability dated Oct. 25, 2016 in Int'l Application No. PCT/JP2015/062627 (English Translation).
Murty et al, "Recyclable CuO Nanoparticles-Catalyzed Synthesis of Novel-2,5-Disubstituted 1,3,4-Oxidiazoles as Antiproliferative, Antibacterial, and Antifungal Agents," Medicinal Chemistry Research, vol. 23, No. 10, pp. 4579-4594 (2014).

* cited by examiner

*Primary Examiner* — Zinna Northington Davis
(74) *Attorney, Agent, or Firm* — Panitch Schwarze Belisario & Nadel LLP

(57) ABSTRACT

Provided is a diaryl-azole compound represented by formula (1)

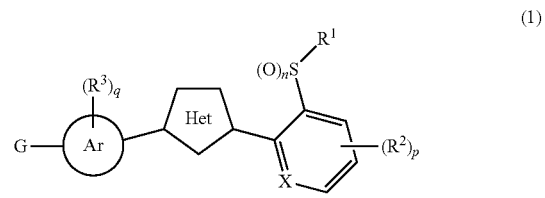

wherein $R^{1-3}$ are $C_{1-6}$ chain hydrocarbon, etc.; p=0-3; q=0-4; n=0-2; X is N, CH, etc.; Ar is phenyl, or 5-6-member aromatic heterocyclic ring; G is $C_{1-6}$ chain hydrocarbon, etc.; and Het is a group selected from formulas (H1) (H2) (H3) described in the specification. The diaryl-azole compound of formula (1) has an excellent controlling effect against arthropod pests. Also provided are a control agent having an excellent controlling effect against arthropod pests, and a method for controlling arthropod pests in which the control agent is used.

9 Claims, No Drawings

DIARYL-AZOLE COMPOUND

CROSS-REFERENCE TO RELATED APPLICATION

This application is a Section 371 of International Application No. PCT/JP2015/062627, filed Apr. 21, 2015, which was published in the Japanese language on Oct. 29, 2015, under International Publication No. WO 2015/163478 A1, and the disclosure of which is incorporated herein by reference.

TECHNICAL FIELD

The present invention relates to a certain type of a diaryl-azole compound and a use thereof for arthropod pest control.

BACKGROUND ART

So far, for the purpose of arthropod pest control, various compounds have been studied and put to practical use.

In addition, a certain type of a diaryl-azole compound (for example, see Patent Document 1) has been known.

PRIOR ART DOCUMENTS

Patent Documents

Patent Document 1: JP-A-2000-318312

SUMMARY OF THE INVENTION

Problems to be Solved by the Invention

An object of the present invention is to provide a compound having an excellent control effect on arthropod pests, a control agent having an excellent control effect on arthropod pests, and a method for controlling arthropod pests using the control agent.

Means for Solving the Problems

As a result of an intensive study to solve the above problem, the present inventors have found that a diaryl-azole compound represented by the following formula (1) has an excellent control effect on arthropod pests, and thereby reaching the present invention.

The present invention is as described below.

[1] An arthropod pest control agent comprising a diaryl-azole compound represented by formula (1):

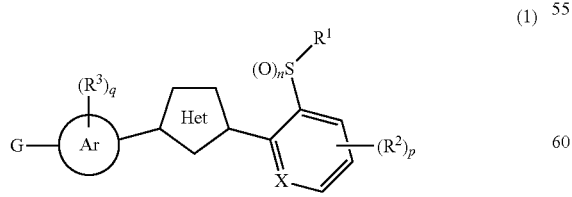

wherein
X represents a nitrogen atom or $CR^4$,
$R^1$ represents a C1 to C6 chain hydrocarbon group optionally having one or more atoms or groups selected from group $\alpha$ or a C3 to C9 alicyclic hydrocarbon group optionally having one or more atoms or groups selected from group $\beta$,
$R^2$ and $R^3$ independently represent a C1 to C6 chain hydrocarbon group optionally having one or more atoms or groups selected from group $\alpha$, a C3 to C9 alicyclic hydrocarbon group optionally having one or more atoms or groups selected from group $\beta$, a phenyl group optionally having one or more atoms or groups selected from group $\gamma$, a 5- or 6-membered heterocyclic group optionally having one or more atoms or groups selected from group $\gamma$, $C(O)R^5$, $C(O)OR^5$, $C(O)NR^5R^6$, $OR^5$, $SR^5$, $S(O)_rR^{5x}$, $S(O)_2NR^5R^6$, $NR^6R^6$, $NR^5C(O)R^6$, $NR^5C(O)OR^6$, a nitro group, a cyano group, or a halogen atom,
$R^4$ represents a C1 to C6 chain hydrocarbon group optionally having one or more atoms or groups selected from group $\alpha$, a C3 to C9 alicyclic hydrocarbon group optionally having one or more atoms or groups selected from group $\beta$, a phenyl group optionally having one or more atoms or groups selected from group $\gamma$, a 5- or 6-membered heterocyclic group optionally having one or more atoms or groups selected from group $\gamma$, $C(O)R^5$, $C(O)OR^5$, $C(O)NR^5R^6$, $OR^5$, $SR^5$, $S(O)_rR^{5x}$, $S(O)_2NR^5R^6$, $NR^6R^6$, $NR^5C(O)R^6$, $NR^5C(O)OR^6$, a nitro group, a cyano group, a halogen atom, or a hydrogen atom,
$R^5$ and $R^6$ independently represent a C1 to C6 chain hydrocarbon group optionally having one ox more atoms or groups selected from group $\alpha$, a C3 to C9 alicyclic hydrocarbon group optionally having one or more atoms or groups selected from group $\beta$, a phenyl group optionally having one or more atoms or groups selected from group $\gamma$, a 5- or 6-membered heterocyclic group optionally having one or more atoms or groups selected from group $\gamma$, or a hydrogen atom,
$R^{5x}$ represents a C1 to C6 chain hydrocarbon group optionally having one or more atoms or groups selected from group $\alpha$, a C3 to C9 alicyclic hydrocarbon group optionally having one or more atoms or groups selected from group $\beta$, a phenyl group optionally having one or more atoms or groups selected from group $\gamma$, or a 5- or 6-membered heterocyclic group optionally having one or more atoms or groups selected from group $\gamma$,
Het represents the following formula H1, H2, or H3:

wherein Q represents an oxygen atom or a sulfur atom,
Ar represents a phenyl group or a 5- or 6-membered aromatic heterocyclic group,
G represents a C1 to C6 chain hydrocarbon group optionally having one or more halogen atoms, a C3 to C6 alicyclic hydrocarbon group optionally having one or more halogen atoms, $OR^7$, $OS(O)_2R^7$, $S(O)_mR^7$, $NR^8S(O)_2R^7$, or a halogen atom (wherein $R^7$ represents a C1 to C6 chain hydrocarbon group optionally having one or more halogen atoms or a C3 to C6 alicyclic hydrocarbon group optionally having one or more halogen atoms, and $R^8$ represents a hydrogen atom, a C1 to C6 chain hydrocarbon group optionally having one or more halogen atoms, or a C3 to C6 alicyclic hydrocarbon group optionally having one or more halogen atoms), n represents 0, 1, or 2,
m represents 0, 1, or 2,
r represents 1 or 2,
p represents 0, 1, 2, or 3 (wherein, when p represents 2 or 3, each $R^2$ may be the same or different), and
q represents 0, 1, 2, 3, or 4 (wherein, when q represents 2, 3, or 4, each $R^3$ may be the same or different).

Group α: a group consisting of a C1 to C6 alkoxy group optionally having one or more halogen atoms, a C2 to C6 alkenyloxy group optionally having one or more halogen atoms, a C2 to C6 alkynyloxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a C2 to C6 alkylcarbonyl group optionally having one or more halogen atoms, a C2 to C6 alkoxycarbonyl group optionally having one or more halogen atoms, a C3 to C6 cycloalkyl group optionally having one or more halogen atoms or one or more C1 to C3 alkyl groups, a cyano group, a hydroxy group, and a halogen atom, Group β: a group consisting of a C1 to C6 chain hydrocarbon group optionally having one or more halogen atoms, a C1 to C6 alkoxy group optionally having one or more halogen atoms, a C2 to C6 alkenyloxy group optionally having one or more halogen atoms, a C2 to C6 alkynyloxy group optionally having one or more halogen atoms, and a halogen atom, and Group γ: a group consisting of a C1 to C6 chain hydrocarbon group optionally having one or more halogen atoms, a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a C2 to C6 alkylcarbonyl group optionally having one or more halogen atoms, a C2 to C6 alkoxycarbonyl group optionally having one or more halogen atoms, a C1 to C6 alkylamino group optionally having one or more halogen atoms, a C2 to C8 dialkylamino group optionally having one or more halogen atoms, a halogen atom, a cyano group, and a nitro group, or an N-oxide thereof (hereinafter, the diarylazole compound represented by the formula (1) and the N-oxide thereof are referred to as the present compound), and an inert carrier (hereinafter, the arthropod pest control agent is referred to as the control agent of the present invention).

[2] The arthropod pest control agent according to [1], wherein Het is a group represented by the formula H1.
[3] The arthropod pest control agent according to [1], wherein Het is a group represented by the formula H2.
[4] The arthropod pest control agent according to [1], wherein Het is a group represented by the formula H3.
[5] The arthropod pest control agent according to any one of [1] to [4], wherein Q is an oxygen atom.
[6] The arthropod pest control agent according to any one of [1] to [4], wherein Q is a sulfur atom.
[7] The arthropod pest control agent according to any one of [1] to [6], wherein X is a nitrogen atom.
[8] The arthropod pest control agent according to any one of [1] to [6], wherein X is $CR^4$.

[9] The arthropod pest control agent according to any one of [1] to [8], wherein Ar is a phenyl group or a pyridyl group.
[10] A method for controlling arthropod pests comprising applying an effective amount of the diaryl-azole compound represented by formula (1):

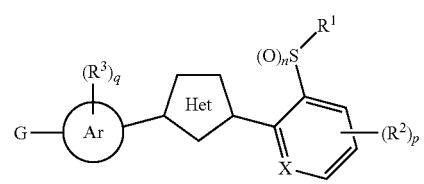

(1)

wherein
X represents a nitrogen atom or $CR^4$,
$R^1$ represents a C1 to C6 chain hydrocarbon group optionally having one or more atoms or groups selected from group α or a C3 to C9 alicyclic hydrocarbon group optionally having one or more atoms or groups selected from group β,
$R^2$ and $R^3$ independently represent a C1 to C6 chain hydrocarbon group optionally having one or more atoms or groups selected from group α, a C3 to C9 alicyclic hydrocarbon group optionally having one or more atoms or groups selected from group β, a phenyl group optionally having one or more atoms or groups selected from group γ, a 5- or 6-membered heterocyclic group optionally having one or more atoms or groups selected from group γ, $C(O)R^5$, $C(O)OR^5$, $C(O)NR^5R^6$, $OR^5$, $SR^5$, $S(O)_rR^{5x}$, $S(O)_2NR^5R^6$, $NR^5R^6$, $NR^5C(O)R^6$, $NR^5C(O)OR^6$, a nitro group, a cyano group, or a halogen atom,
$R^4$ represents a C1 to C6 chair hydrocarbon group optionally having one or more atoms or groups selected from group α, a C3 to C9 alicyclic hydrocarbon group optionally having one or more atoms or groups selected from group β, a phenyl group optionally having one or more atoms or groups selected from group γ, a 5- or 6-membered heterocyclic group optionally having one or more atoms or groups selected from group γ, $C(O)R^5$, $C(O)OR^6$, $C(O)NR^5R^6$, $OR^5$, $SR^5$, $S(O)_rR^{5x}$, $S(O)_2NR^5R^6$, $NR^5R^6$, $NR^5C(O)R^6$, $NR^5C(O)OR^6$, a nitro group, a cyano group, a halogen atom, ox a hydrogen atom,
$R^5$ and $R^6$ independently represent a C1 to C6 chain hydrocarbon group optionally having one or more atoms or groups selected from group α, a C3 to C9 alicyclic hydrocarbon group optionally having one or more atoms or groups selected from group β, a phenyl group optionally having one or more atoms or groups selected from group γ, a 5- or 6-membered heterocyclic group optionally having one or more atoms or groups selected from group γ, or a hydrogen atom,
$R^{5x}$ represents a C1 to C6 chain hydrocarbon group optionally having one or more atoms or groups selected from group α, a C3 to C9 alicyclic hydrocarbon group optionally having one or more atoms or groups selected from group β, a phenyl group optionally having one or more atoms or groups selected from group γ, or a 5- or 6-membered heterocyclic group optionally having one or more atoms or groups selected from group γ,
Het represents the following formula H1, H2, or H3:

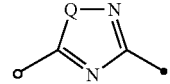

(H1)

-continued

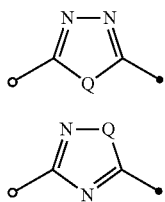
(H2)

(H3)

wherein Q represents an oxygen atom or a sulfur atom,
Ar represents a phenyl group or a 5- or 6-membered aromatic heterocyclic group,
G represents a C1 to C6 chain hydrocarbon group optionally having one or more halogen atoms, a C3 to C6 alicyclic hydrocarbon group optionally having one or more halogen atoms, $OR^7$, $OS(O)_2R^7$, $S(O)_mR^7$, $NR^8S(O)_2R^7$, or a halogen atom (wherein $R^7$ represents a C1 to C6 hydrocarbon group optionally having one or more halogen atoms or a C3 to C6 alicyclic hydrocarbon group optionally having one or more halogen atoms, and $R^8$ represents a hydrogen atom, a C1 to C6 chain hydrocarbon group optionally having one or more halogen atoms, or a C3 to C6 alicyclic hydrocarbon group optionally having one or more halogen atoms),
n represents 0, 1, or 2,
m represents 0, 1, or 2,
r represents 1 or 2,
p represents 0, 1, 2, or 3 (wherein, when p represents 2 or 3, each $R^2$ may be the same or different), and
q represents 0, 1, 2, 3, or 4 (wherein, when q represents 2, 3, or 4, each $R^3$ may be the same or different).
Group α: a group consisting of a C1 to C6 alkoxy group optionally having one or more halogen atoms, a C2 to C6 alkenyloxy group optionally having one or more halogen atoms, a C2 to C6 alkynyloxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a C2 to C6 alkylcarbonyl group optionally having one or more halogen atoms, a C2 to C6 alkoxycarbonyl group optionally having one or more halogen atoms, a C3 to C6 cycloalkyl group optionally having one or more halogen atoms or one or more C1 to C3 alkyl groups, a cyano group, a hydroxy group, and a halogen atom,
Group β: a group consisting of a C1 to C6 chain hydrocarbon group optionally having one or more halogen atoms, a C1 to C6 alkoxy group optionally having one or more halogen atoms, a C2 to C6 alkenyloxy group optionally having one or more halogen atoms, a C2 to C6 alkynyloxy group optionally having one or more halogen atoms, and a halogen atom, and
Group γ: a group consisting of a C1 to C6 chain hydrocarbon group optionally having one or more halogen atoms, a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a C2 to C6 alkylcarbonyl group optionally having one or more halogen atoms, a C2 to C6 alkoxycarbonyl group optionally having one or more halogen atoms, a C1 to C6 alkylamino group optionally having one or more halogen atoms, a C2 to C8 dialkylamino group optionally having one or more halogen atoms, a halogen atom, a cyano group, and a nitro group, or an N-oxide thereof to an arthropod pest or an arthropod pest-infested area.

[11] A diaryl-azole compound represented by formula (2):

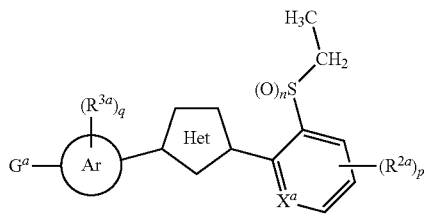
(2)

wherein
$X^a$ represents a nitrogen atom or $CR^{4a}$,
$R^{2a}$ and $R^{3a}$ independently represent a C1 to C6 chain hydrocarbon group optionally having one or more atoms or groups selected from group α, a C3 to C9 alicyclic hydrocarbon group optionally having one or more atoms or groups selected from group β, a phenyl group optionally having one or more atoms or groups selected from group γ, a 5- or 6-membered heterocyclic group optionally having one or more atoms or groups selected from group γ, $C(O)R^{5a}$, $C(O)OR^{5a}$, $C(O)NR^{5a}R^{6a}$, $OR^{5a}$, $SR^{5a}$, $S(O)_rR^{5y}$, $S(O)_2NR^{5a}R^{6a}$, $NR^{5a}R^{6a}$, $NR^{5a}C(O)R^{6a}$, $NR^{5a}C(O)OR^{6a}$, a nitro group, a cyano group, or a halogen atom,
$R^{4a}$ represents a C1 to C6 chain hydrocarbon group optionally having one or more atoms or groups selected from group α, a C3 to C9 alicyclic hydrocarbon group optionally having one or more atoms or groups selected from group β, a phenyl group optionally having one or more atoms or groups selected from group γ, a 5- or 6-membered heterocyclic group optionally having one or more atoms or groups selected from group γ, $C(O)R^{5a}$, $C(O)R^{5a}$, $C(O)NR^{5a}R^{6a}$, $OR^{5a}$, $SR^{5a}$, $S(O)_rR^{5y}$, $S(O)_2NR^{5a}R^{5b}$, $NR^{5a}R^{6a}$, $NR^{5a}C(O)R^{6a}$, $NR^{5a}C(O)OR^{6a}$, a nitro group, a cyano group, a halogen atom, or a hydrogen atom,
$R^{5a}$ and $R^{6a}$ independently represent a C1 to C6 chain hydrocarbon group optionally having one or more atoms or groups selected from group α, a C3 to C9 alicyclic hydrocarbon group optionally having one or more atoms or groups selected from group β, a phenyl group optionally having one or more atoms or groups selected from group γ, a 5- or 6-membered heterocyclic group optionally having one or more atoms or groups selected from group γ, or a hydrogen atom,
$R^{5y}$ represents a C1 to C6 chain hydrocarbon group optionally having one or more atoms or groups selected from group α, a C3 to C9 alicyclic hydrocarbon group optionally having one or more atoms or groups selected from group β, a phenyl group optionally having one or more atoms or groups selected from group γ, or a 5- or 6-membered heterocyclic group optionally having one or more atoms or groups selected from group γ,
Het represents the following formula H1, H2, or H3:

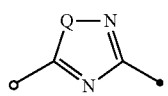
(H1)

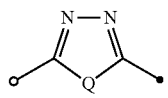
(H2)

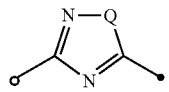 (H3)

wherein Q represents an oxygen atom or a sulfur atom,
Ar represents a phenyl group or a 5- or 6-membered aromatic heterocyclic group,
$G^a$ represents a C1 to C6 chain hydrocarbon group having one or more halogen atoms, a C3 to C6 alicyclic hydrocarbon group having one or more halogen atoms, $OR^{7a}$, $OS(O)_2R^{7a}$, $S(O)_mR^{7a}$, or $NR^{8a}S(O)_2R^{7a}$ (wherein $R^{7a}$ represents a C1 to C6 chain hydrocarbon group having one or more halogen atoms or a C3 to C6 alicyclic hydrocarbon group having one or more halogen atoms, and $R^{8a}$ represents a hydrogen atom, a C1 to C6 chain hydrocarbon group having one or more halogen atoms, or a C3 to C6 alicyclic hydrocarbon group having one or more halogen atoms),
n represents 0, 1, or 2,
m represents 0, 1, or 2,
r represents 1 or 2,
p represents 0, 1, 2, or 3 (wherein, when p represents 2 or 3, each $R^{2a}$ may be the same or different), and
q represents 0, 1, 2, 3, or 4 (wherein, when q represents 2, 3, or 4, each $R^{3a}$ may be the same or different).
Group α: a group consisting of a C1 to C6 alkoxy group optionally having one or more halogen atoms, a C2 to C6 alkenyloxy group optionally having one or more halogen atoms, a C2 to C6 alkynyloxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a C2 to C6 alkylcarbonyl group optionally having one or more halogen atoms, a C2 to C6 alkoxycarbonyl group optionally having one or more halogen atoms, a C3 to C6 cycloalkyl group optionally having one or more halogen atoms or one or more C1 to C3 alkyl groups, a cyano group, a hydroxy group, and a halogen atom,
Group β: a group consisting of a C1 to C6 chain hydrocarbon group optionally having one or more halogen atoms, a C1 to C6 alkoxy group optionally having one or more halogen atoms, a C2 to C6 alkenyloxy group optionally having one or more halogen atoms, a C2 to C6 alkynyloxy group optionally having one or more halogen atoms, and a halogen atom, and
Group γ: a group consisting of a C1 to C6 chain hydrocarbon group optionally having one or more halogen atoms, a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a C2 to C6 alkylcarbonyl group optionally having one or more halogen atoms, a C2 to C6 alkoxycarbonyl group optionally having one or more halogen atoms, a C1 to C6 alkylamino group optionally having one or more halogen atoms, a C2 to C8 dialkylamino group optionally having one or more halogen atoms, a halogen atom, a cyano group, and a nitro group, or an N-oxide thereof.

MODE FOR CARRYING OUT THE INVENTION

The groups used in the description of the present specification will be described below with examples.

In the phrase "optionally having one or more halogen atoms" in the present specification, when having two or more halogen atoms, those halogen atoms may be the same or different from each other.

For example, the notation of "C1 to C6" in the present specification means that the number of carbon atoms is 1 to 6.

The phrase "C1 to C6 chain hydrocarbon group" in the present specification represents a C1 to C6 alkyl group, a C2 to C6 alkenyl group, and a C2 to C6 alkynyl group.

The phrase "alicyclic hydrocarbon group" in the present specification represents, for example, a cycloalkyl group and a cycloalkenyl group.

The halogen atom refers to a fluorine atom, a chlorine atom, a bromine atom, and an iodine atom.

The heterocyclic group represents an aromatic or non-aromatic heterocyclic group containing one or more nitrogen atoms, oxygen atoms or sulfur atoms, other than carbon atoms, as ring-constituting atoms, and represents, for example, a 5-membered non-aromatic heterocyclic group such as a pyrrolidyl group, a tetrahydrofuryl group and a tetrahydrothienyl group, 5-membered aromatic heterocyclic groups such as a pyrrolyl group, a pyrazolyl group, an imidazolyl group, a furyl group, a thienyl group, an oxazolyl group and a thiazolyl group, a 6-membered non-aromatic heterocyclic group such as a piperidinyl group, a tetrahydropyranyl group, a tetrahydrothiopyranyl group, a piperazinyl group and a morpholinyl group, and a 6-membered aromatic heterocyclic group such as a pyridyl group, a pyrimidinyl group, a pyridazinyl group, and a pyrazinyl group.

The term "Het" in the present specification represents a 5-membered ring having two carbon atoms, two nitrogen atoms and one oxygen atom or sulfur group, as ring-constituting atoms, and specifically includes the following formula (H1-O) to formula (H3-S).

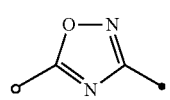 (H1-O)

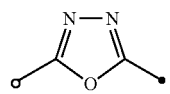 (H2-O)

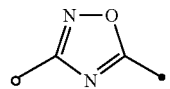 (H3-O)

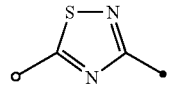 (H1-S)

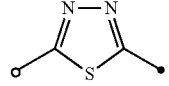 (H2-S)

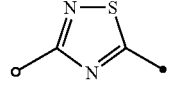 (H3-S)

In the formulae, "○" represents a position bound to Ar, and "●" represents a position bound to a formula (AA1).

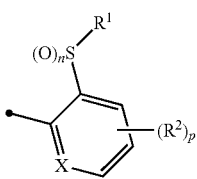
(AA1)

wherein symbols represent the same meaning as in the formula (1).

Examples of the 5- or 6-membered aromatic heterocyclic groups include a pyrrolyl group, a pyrazolyl group, an imidazolyl group, a furyl group, a thienyl group, an oxazolyl group, an isoxazolyl group, a thiazolyl group, an isothiazolyl group, a triazolyl group, a 1,2,4-oxadiazolyl group, a 1,3,4-oxadiazolyl group, a 1,2,4-thiadiazolyl group, a 1,3,4-thiadiazolyl group, a pyridyl group, a pyrimidinyl group, a pyridazinyl group, and a pyrazinyl group.

In the present specification, the structure represented by formula (ArX) is represented as "$(R^3)qGAr$-".

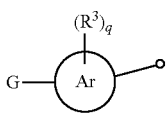
(ArX)

wherein symbols represent the same meaning as in the formula (1).

Examples of "$(R^3)qGAr$-" include the following formulae (Ar-A) to (Ar-F).

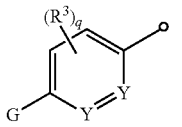
(Ar-A)

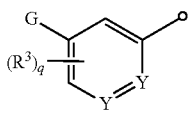
(Ar-B)

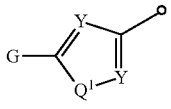
(Ar-C)

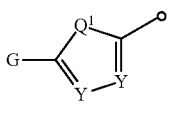
(Ar-D)

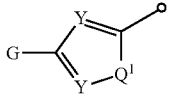
(Ar-E)

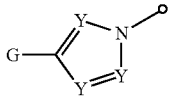
(Ar-F)

wherein Y independently represents a nitrogen atom, CH, or $CR^3$, $Q^1$ represents $NR^{3x}$, an oxygen atom, or a sulfur atom, $R^{3x}$ represents a hydrogen atom, a C1 to C6 chain hydrocarbon group optionally having one or more atoms or groups selected from group α, a C3 to C9 alicyclic hydrocarbon group optionally having one or more atoms or groups selected from group β, a phenyl group optionally having one or more atoms or groups selected from group γ, a 5- or 6-membered heterocyclic group optionally having one or more atoms or groups selected from group γ, $C(O)R^5$, $C(O)OR^5$, or $C(O)NR^5R^6$, and other symbols represent the same meaning as in the formula (1).

Further specifically, examples include the following formulae (Ar1) to (Ar 15).

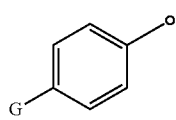
(Ar1)

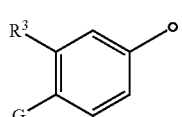
(Ar2)

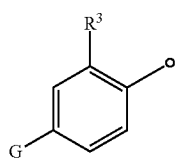
(Ar3)

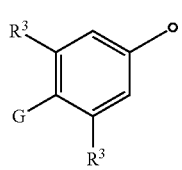
(Ar4)

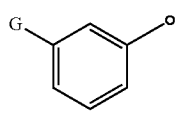
(Ar5)

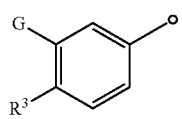
(Ar6)

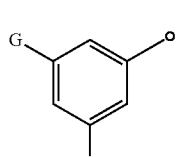
(Ar7)

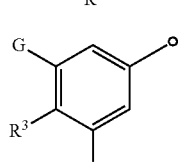
(Ar8)

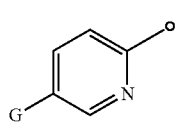
(Ar9)

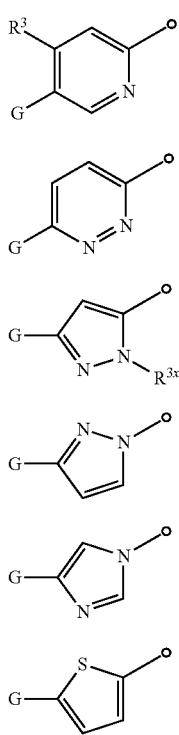

(Ar10)

(Ar11)

(Ar12)

(Ar13)

(Ar14)

(Ar15)

wherein symbols represent the same meaning as in the formula (1).

The N-oxide herein refers to a compound in which a nitrogen atom constituting a heterocyclic ring is oxidized. Examples of the heterocyclic ring that may form an N-oxide include a pyridine ring and a Fyridazine ring. Specifically, examples include the following formula (1-n2-X=N—N1).

Formula (1-n2-X=N-N1)

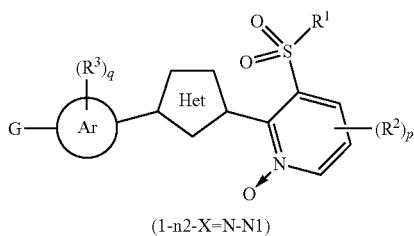

(1-n2-X=N-N1)

wherein symbols represent the same meaning as in the formula (1).

Examples of the control agent of the present invention include the following control agents.

Embodiment 1

In the formula (1), control agents of the present invention wherein $R^1$ is a C1 to C6 chain hydrocarbon group optionally having one or more atoms or groups selected from group α;

Embodiment 2

In Embodiment 1, control agents of the present invention wherein X is a nitrogen atom or CH, $R^2$ and $R^3$ independently are a C1 to C6 chain hydrocarbon group optionally having one or more atoms or groups selected from group α, or a halogen atom, G is a C1 to C6 chain hydrocarbon group optionally having one or more halogen atoms, $S(O)_m R^7$, or a halogen atom (wherein $R^7$ is a C1 to C6 chain hydrocarbon group optionally having one or more halogen atoms), p is 0 or 1, and q is 0 or 1;

Embodiment 3

In Embodiment 1 to Embodiment 2, control agents of the present invention wherein $R^1$ is a C1 to C6 alkyl group;

Embodiment 4

In Embodiment 1 to Embodiment 2, control agents of the present invention wherein $R^1$ is a C1 to C3 alkyl group;

Embodiment 5

In Embodiment 1 to Embodiment 2, control agents of the present invention wherein $R^1$ is an ethyl group;

Embodiment 6

In Embodiment 1 to Embodiment 5, control agents of the present invention wherein $R^2$, $R^3$ and G are independently a C1 to C6 chain hydrocarbon group optionally having one or more halogen atoms or a halogen atom;

Embodiment 7

In Embodiment 6, control agents of the present invention wherein $R^2$, $R^3$ and G are independently a C1 to C6 alkyl group optionally having one or more halogen atoms or a halogen atom;

Embodiment 8

In Embodiment 6, control agents of the present invention wherein $R^2$, $R^3$ and G are independently a C1 to C3 alkyl group optionally having one or more halogen atoms or a halogen atom;

Embodiment 9

In Embodiment 6, control agents of the present invention wherein $R^2$, $R^3$ and G are independently a trifluoromethyl group or a halogen atom;

Embodiment 10

In Embodiment 1 to Embodiment 9, control agents of the present invention wherein Ar is a pyrrolyl group;

Embodiment 11

In Embodiment 1 to Embodiment 9, control agents of the present invention wherein Ar is a pyrazolyl group;

Embodiment 12

In Embodiment 1 to Embodiment 9, control agents of the present invention wherein Ar is an imidazolyl group;

Embodiment 13

In Embodiment 1 to Embodiment 9, control agents of the present invention wherein Ar is a furyl group;

Embodiment 14

In Embodiment 1 to Embodiment 9, control agents of the present invention wherein Ar is a thienyl group;

Embodiment 15

In Embodiment 1 to Embodiment 9, control agents of the present invention wherein Ar is an oxazolyl group;

Embodiment 16

In Embodiment 1 to Embodiment 9, control agents of the present invention wherein Ar is an isoxazolyl group;

Embodiment 17

In Embodiment 1 to Embodiment 9, control agents of the present invention wherein Ar is a thiazolyl group;

Embodiment 18

In Embodiment 1 to Embodiment 9, control agents of the present invention wherein Ar is an isothiazolyl group;

Embodiment 19

In Embodiment 1 to Embodiment 9, control agents of the present invention wherein Ar is a triazolyl group;

Embodiment 20

In Embodiment 1 to Embodiment 9, control agents of the present invention wherein Ar is a 1,2,4-oxadiazolyl group;

Embodiment 21

In Embodiment 1 to Embodiment 9, control agents of the present invention wherein Ar is a 1,3,4-oxadiazolyl group;

Embodiment 22

In Embodiment 1 to Embodiment 9, control agents of the present invention wherein Ar is a 1,2,4-thiadiazolyl group;

Embodiment 23

In Embodiment 1 to Embodiment 9, control agents of the present invention wherein Ar is a 1,3,4-thiadiazolyl group;

Embodiment 24

In Embodiment 1 to Embodiment 9, control agents of the present invention wherein Ar is a pyridyl group;

Embodiment 25

In Embodiment 1 to Embodiment 9, control agents of the present invention wherein Ar is a pyrimidinyl group;

Embodiment 26

In Embodiment 1 to Embodiment 9, control agents of the present invention wherein Ar is a pyridazinyl group;

Embodiment 27

In Embodiment 1 to Embodiment 9, control agents of the present invention wherein Ar is a pyrazinyl group;

Embodiment 28

In Embodiment 1 to Embodiment 9, control agents of the present invention wherein Ar is a phenyl group;

Embodiment 29

In Embodiment 1 to Embodiment 28, control agents of the present invention wherein Het is H1;

Embodiment 30

In Embodiment 1 to Embodiment 28, control agents of the present invention wherein Het is H1-O;

Embodiment 31

In Embodiment 1 to Embodiment 28, control agents of the present invention wherein Het is H1-S;

Embodiment 32

In Embodiment 1 to Embodiment 28, control agents of the present invention wherein Het is H2;

Embodiment 33

In Embodiment 1 to Embodiment 28, control agents of the present invention wherein Het is H2-O;

Embodiment 34

In Embodiment 1 to Embodiment 28, control agents of the present invention wherein Het is H2-S;

Embodiment 35

In Embodiment 1 to Embodiment 28, control agents of the present invention wherein Het is H3;

Embodiment 36

In Embodiment 1 to Embodiment 28, control agents of the present invention wherein Het is H3-O;

Embodiment 37

In Embodiment 1 to Embodiment 28, control agents of the present invention wherein Met is H3-S;

Embodiment 38

In Embodiment 1 to Embodiment 37, control agents of the present invention wherein X is a nitrogen atom;

Embodiment 39

In Embodiment 1 to Embodiment 37, control agents of the present invention wherein X is CH;

Embodiment 40

In the formula (2), compounds wherein $X^a$ is a nitrogen atom or CH, $R^{2a}$ and $R^{3a}$ independently represent a C1 to C6 chain hydrocarbon group optionally having one or more halogen atoms or a halogen atom, and
$G^a$ is a C1 to C6 chain hydrocarbon group optionally having one or more halogen atoms;

Embodiment 41

In Embodiment 40, compounds wherein $R^{2a}$ and $R^{3a}$ are independently a C1 to C6 alkyl group optionally having one or more halogen atoms or a halogen atom;

Embodiment 42

In Embodiment 40, compounds wherein $R^{2a}$ and $R^{3a}$ are independently a C1 to C3 alkyl group optionally having one or more halogen atoms or a halogen atom;

Embodiment 43

In Embodiment 40, compounds wherein $R^{2a}$ and $R^{3a}$ are independently trifluoromethyl or a halogen atom;

Embodiment 44

In Embodiment 40 to Embodiment 43, compounds wherein $G^a$ is a C1 to C6 chain hydrocarbon group having one or more halogen atoms or $S(O)_m R^{7a}$;

Embodiment 45

In Embodiment 44, compounds wherein $G^a$ is a C1 to C6 alkyl group having one or more halogen atoms;

Embodiment 46

In Embodiment 44, compounds wherein $G^a$ is a C1 to C3 alkyl group having one or more halogen atoms;

Embodiment 47

In Embodiment 44, compounds wherein $G^a$ is a trifluoromethyl group;

Embodiment 48

In Embodiment 40 to Embodiment 46, compounds wherein Ar is a phenyl group, a pyridyl group, a thienyl group, a pyrazolyl group, an imidazolyl group, or a triazolyl group;

Embodiment 49

In Embodiment 48, compounds wherein Ar is a phenyl group;

Embodiment 50

In Embodiment 48, compounds wherein Ar is a pyridyl group;

Embodiment 51

In Embodiment 48, compounds wherein Ar is a thienyl group;

Embodiment 52

In Embodiment 48, compounds wherein Ar is a pyrazolyl group;

Embodiment 53

In Embodiment 48, compounds wherein Ar is an imidazolyl group;

Embodiment 54

In Embodiment 48, compounds wherein Ar is a triazolyl group;

Embodiment 57

In Embodiment 40 to Embodiment 43, compounds wherein "$(R^3)qGAr$-" is a 3-(trifluoromethyl)phenyl group;

Embodiment 58

In Embodiment 40 to Embodiment 43, compounds wherein "$(R^3)qGAr$-" is a 4-(trifluoromethyl)phenyl group;

Embodiment 59

In Embodiment 40 to Embodiment 43, compounds wherein "$(R^3)qGAr$-" is a 3, 5-bis(trifluoromethyl)phenyl group;

Embodiment 60

In Embodiment 40 to Embodiment 59, compounds wherein Het is H1;

Embodiment 61

In Embodiment 40 to Embodiment 59, compounds wherein Het is H1-O;

Embodiment 62

In Embodiment 40 to Embodiment 59, compounds wherein Net is H1-S;

Embodiment 63

In Embodiment 40 to Embodiment 59, compounds wherein Het is H2;

Embodiment 64

In Embodiment 40 to Embodiment 59, compounds wherein Het is H2-O;

Embodiment 65

In Embodiment 40 to Embodiment 59, compounds wherein Het is H2-S;

Embodiment 66

In Embodiment 40 to Embodiment 59, compounds wherein Net is H3;

Embodiment 67

In Embodiment 40 to Embodiment 59, compounds wherein Net is H3-O;

Embodiment 68

In Embodiment 40 to Embodiment 59, compounds wherein Het is H3-S;

Embodiment 69

In Embodiment 40 to Embodiment 68, compounds wherein $X^a$ is a nitrogen atom;

Embodiment 70

In Embodiment 40 to Embodiment 68, compounds wherein $X^a$ is CH.

Next, the method for producing the present compound will be described.

The present compound and the production intermediate compound can be produced, for example, according to the following (Production Method 1) to (Production Method 14).

(Production Method 1)

The present compound in which n is 1 (hereinafter referred to as the present compound (1-n1)) or the present compound in which n is 2 (hereinafter referred to as the present compound (1-n2)) in the formula (1) can be produced by oxidizing the present compound in which n is 0 (hereinafter referred to as the present compound (1-n0)).

After completion of the reaction, the reaction mixture is extracted with an organic solvent, and the organic layer is washed with an aqueous solution of a reducing agent (for example, sodium sulfite, sodium thiosulfate) and an aqueous solution of a base (for example, sodium bicarbonate) as necessary, and subjected to post-treatment operations such as drying and concentration, whereby the present compound (1-n1) can be isolated. The isolated present compound (1-n1) also can be further purified by chromatography, recrystallization, or the like.

The present compound (1-n2) can be produced by oxidizing the present compound (1-n1).

The reaction is usually carried out in the presence of a solvent.

Examples of the solvent used in the reaction include aliphatic halogenated hydrocarbons such as dichloromethane and chloroform, alcohols such as methanol and ethanol, esters such as ethyl acetate, acetic acid, water, and mixtures thereof.

Examples of the oxidizing agent used in the reaction include m-chloroperbenzoic acid, aqueous hydrogen peroxide and oxone (registered trademark).

The reaction also can be carried out in the presence of a catalyst, as necessary.

Examples of the catalyst used in the reaction include tungstic acid, sodium tungstate and potassium tungstate.

In the reaction, the oxidizing agent is usually used in a ratio of 1 to 4 mol, and the catalyst is usually used in a ratio of 0.01 to 0.5 mol, based on 1 mol of the present compound (1-n1). Preferably, the oxidizing agent is used in a ratio of 1 to 2 mol, and the catalyst is used in a ratio of 0.05 to 0.2 mol, based on 1 mol of the present compound (1-n1).

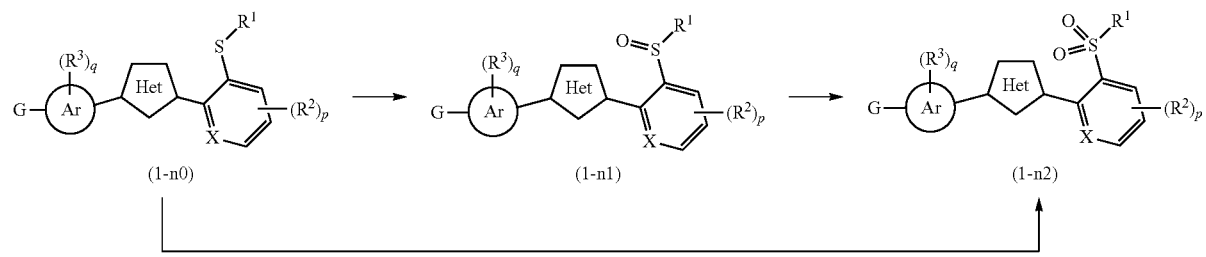

wherein symbols represent the same meaning as in the formula (1).

The present compound (1-n1) in the formula (1) can be produced by subjecting the present compound (1-n0) to an oxidation reaction.

The reaction is usually carried out in the presence of a solvent.

Examples of the solvent used in the reaction include aliphatic halogenated hydrocarbons such as dichloromethane and chloroform, alcohols such as methanol and ethanol, esters such as ethyl acetate, acetic acid, water, and mixtures thereof.

Examples of the oxidizing agent used in the reaction include sodium periodate and n-chloroperbenzoic acid.

In the reaction, the oxidizing agent is usually used in a ratio of 1 to 1.5 mol, based on 1 mol of the present compound (1-n0). Preferably, the oxidizing agent is used in a ratio of 1 to 1.2 mol, based on 1 mol of the present compound (1-n0).

The reaction temperature in the reaction is usually in the range of −50 to 50° C. The reaction time in the reaction is usually in the range of 0.1 to 12 hours.

The reaction temperature in the reaction is usually in the range of −50 to 100° C. The reaction time in the reaction is usually in the range of 0.1 to 12 hours.

After completion of the reaction, the reaction mixture is extracted with an organic solvent, and the organic layer is washed with an aqueous solution of a reducing agent (for example, sodium sulfite, sodium thiosulfate) and an aqueous solution of a base (for example, sodium bicarbonate) as necessary, and subjected to post-treatment operations such as drying and concentration, whereby the present compound (1-n2) can be isolated. The present compound (1-n2) also can be further purified by chromatography, recrystallization, or the like.

The present compound (1-n2) in which n is 2 in the formula (1) can be produced by a one step reaction (one pot) by oxidizing the present compound (1-n0) in which n is 0.

The reaction is usually carried out in the presence of a solvent.

Examples of the solvent used in the reaction include aliphatic halogenated hydrocarbons such as dichloromethane and chloroform, alcohols such as methanol and ethanol, esters such as ethyl acetate, acetic acid, water, and mixtures thereof.

Examples of the oxidizing agent used in the reaction include m-chloroperbenzoic acid, aqueous hydrogen peroxide and oxone (registered trademark).

The reaction also can be carried out in the presence of a catalyst, as necessary.

Examples of the catalyst used in the reaction include tungstic acid, sodium tungstate and potassium tungstate.

In the reaction, the oxidizing agent is usually used in a ratio of 2 to 5 mol, and the catalyst is usually used in a ratio of 0.01 to 0.5 mol, based on 1 mol of the present compound (1-n0). Preferably, the oxidizing agent is used in a ratio of 2 to 3 mol, and the catalyst is used in a ratio of 0.05 to 0.2 mol, based on 1 mol of the present compound (1-n0).

The reaction temperature in the reaction is usually in the range of 0 to 120° C. The reaction time in the reaction is usually in the range of 0.1 to 12 hours.

After completion of the reaction, the reaction mixture is extracted with an organic solvent, and the organic layer is washed with an aqueous solution of a reducing agent (for example, sodium sulfite, sodium thiosulfate) and an aqueous solution of a base (for example, sodium bicarbonate) as necessary, and subjected to post-treatment operations such as drying and concentration, whereby the present compound (1-n2) can be isolated. The isolated present compound (1-n2) also can be further purified by chromatography, recrystallization, or the like.

(Production Method 2)

The present compound (1-n0) can be produced by reacting a compound represented by formula (M1) (hereinafter, referred to as intermediate compound (M1)) with a compound represented by formula (M2) (hereinafter, referred to as compound (M2)) in the presence of a base.

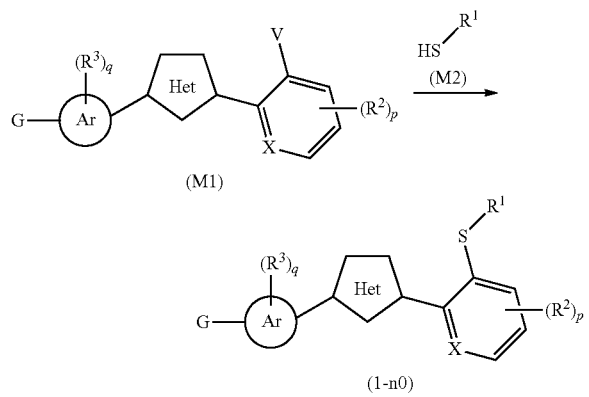

wherein V represents a halogen atom, and other symbols represent the same meaning as in the formula (1).

The reaction is usually carried out in the presence of a solvent.

Examples of the solvent used in the reaction include ethers such as tetrahydrofuran (hereinafter, referred to as THF), ethylene glycol dimethyl ether, tert-butyl methyl ether and 1,4-dioxane, aromatic hydrocarbons such as toluene and xylene, nitriles such as acetonitrile, aprotic polar solvents such as N, N-dimethylformamide (hereinafter, referred to as DMF), N-methyl pyrrolidone (hereinafter, referred to as NMP), 1,3-dimethyl-2-imidazolidinone and dimethyl sulfoxide (hereinafter, referred to as DMSO), water, and mixtures thereof.

Examples of the base used in the reaction include alkali metal carbonates such as sodium carbonate and potassium carbonate, and alkali metal hydrides such as sodium hydride.

In the reaction, the compound (M2) is usually used in a ratio of 1 to 10 mol, and the base is usually used in a ratio of 1 to 10 mol, based on 1 mol of the intermediate compound (M).

The reaction temperature in the reaction is usually in the range of −50 to 100° C. The reaction time in the reaction is usually in the range of 0.1 to 12 hours.

After completion of the reaction, water was added to the reaction mixture, then the mixture is extracted with an organic solvent, and the organic layer is subjected to post-treatment operations such as drying and concentration, whereby the present compound (1-n0) can be isolated. The isolated present compound (1-n0) also can be further purified by chromatography, recrystallization, or the like.

In the reaction, V is preferably a fluorine atom or a chlorine atom.

(Production Method 3)

A compound in which Het is H1 and Q is an oxygen atom in the formula (1) (hereinafter, referred to as present compound (1-H1-Q=O)) can be produced by reacting a compound represented by formula (M4) (hereinafter, referred to as intermediate compound (M4)) with a compound represented by formula (M5) (hereinafter, referred to as intermediate compound (M5)).

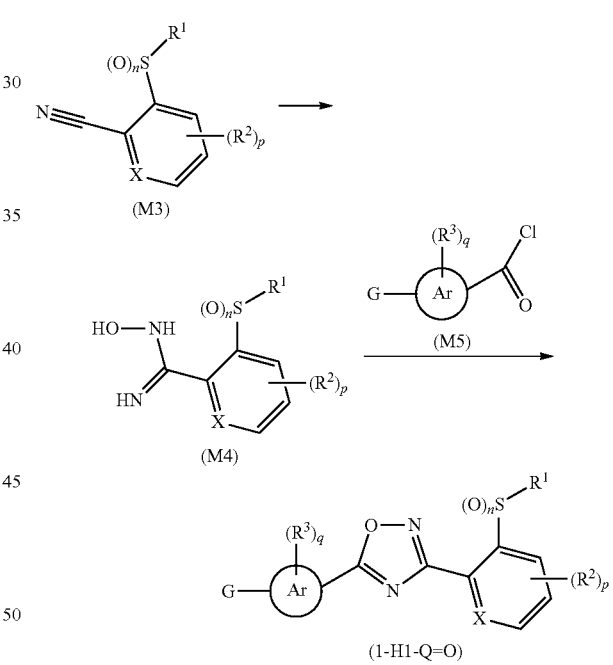

wherein symbols represent the same meaning as in the formula (1).

The intermediate compound (M4) can be produced by reacting a compound represented by formula (M3) (hereinafter, referred to as intermediate compound (M3)) with hydroxylamine, in the presence of a base.

The reaction is usually carried out in the presence of a solvent.

Examples of the solvent used in the reaction include alcohols such as methanol and ethanol, ethers such as THF, ethylene glycol dimethyl ether, tert-butyl methyl ether and 1,4-dioxane, aromatic hydrocarbons such as toluene and xylene, nitriles such as acetonitzile, aprotic polar solvents such as DMF, NMP and DMSO, water, and mixtures thereof.

Examples of the base used in the reaction include alkali metal carbonates such as sodium carbonate and potassium carbonate, and alkali metal hydrides such as sodium hydride.

In the reaction, hydroxylamine is usually used in a ratio of 1 to 10 mol, and the base is usually used in a ratio of 1 to 10 mol, based on 1 mol of the intermediate compound (M3).

The reaction temperature in the reaction is usually in the range of 0 to 150° C. The reaction time in the reaction is usually in the range of 0.1 to 24 hours.

After completion of the reaction, water was added to the reaction mixture, then the mixture is extracted with an organic solvent, and the organic layer is subjected to post-treatment operations such as drying and concentration, whereby the intermediate compound (M4) can be isolated. The isolated intermediate compound (M4) also can be further purified by chromatography, recrystallization, or the like.

The present compound (1-H1-Q=O) can be produced by reacting the intermediate compound (M4) with the intermediate compound (M5), in the presence of a base.

The reaction is usually carried out in the presence of a solvent.

Examples of the solvent used in the reaction include alcohols such as methanol and ethanol, ethers such as THF, ethylene glycol dimethyl ether, tert-butyl methyl ether and 1,4-dioxane, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile, aprotic polar solvents such as DMF, NMP and DMSO, nitrogen-containing aromatic compounds such as pyridine and quinoline, and mixtures thereof.

The base used in the reaction includes alkali metal carbonates such as sodium carbonate and potassium carbonate, tertiary amines such as triethylamine and N,N-diisopropylethylamine, nitrogen-containing aromatic compounds such as pyridine and 4-dimethylaminopyridine, and the like.

In the reaction, the intermediate compound (M5) is usually used in a ratio of 1 to 3 mol, and the base is usually used in a ratio of 1 to 5 mol, based on 1 mol of the intermediate compound (M4).

The reaction temperature in the reaction is usually in the range of 0 to 200° C. The reaction time in the reaction is usually in the range of 0.1 to 24 hours.

After completion of the reaction, water was added to the reaction mixture, then the mixture is extracted with an organic solvent, and the organic layer is subjected to post-treatment operations such as drying and concentration, whereby the present compound (1-H1-Q=O) can be isolated. The isolated present compound (1-H1-Q=O) also can be further purified by chromatography, recrystallization, or the like.

(Production Method 4)

A compound in which Het is H1 and 0 is a sulfur atom in the formula (1) (hereinafter, referred to as present compound (1-H1-Q=S)) can be produced by reacting a compound represented by formula (M7) (hereinafter, referred to as intermediate compound (M7)) with an oxidizing agent.

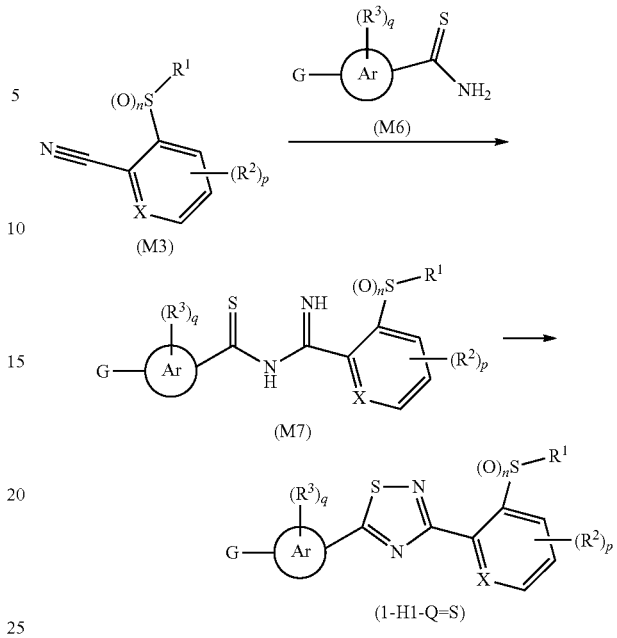

wherein symbols represent the same meaning as in the formula (1).

The intermediate compound (M7) can be produced by reacting the intermediate compound (M3) with a compound represented by formula (M6) (hereinafter, referred to as intermediate compound (M6)), in the presence of an acid.

The reaction is usually carried out in the presence of a solvent.

Examples of the solvent used in the reaction include ethers such as THF, ethylene glycol dimethyl ether, tert-butyl methyl ether and 1,4-dioxane, water, and mixtures thereof.

Examples of the acid used in the reaction include mineral acids such as hydrochloric acid, nitric acid, phosphoric acid, and sulfuric acid.

In the reaction, the intermediate compound (M6) is usually used in a ratio of 1 to 3 mol, and the acid is usually used in a ratio of 0.1 to 10 mol, based on 1 mol of the intermediate compound (M3).

The reaction temperature in the reaction is usually in the range of 0 to 200° C. The reaction time in the reaction is usually in the range of 0.1 to 24 hours.

After completion of the reaction, water was added to the reaction mixture, then the mixture is extracted with an organic solvent, and the organic layer is subjected to post-treatment operations such as drying and concentration, whereby the intermediate compound (M7) can be isolated. The isolated intermediate compound (M7) also can be further purified by chromatography, recrystallization, or the like.

The present compound (1-H1-Q=S) can be produced by reacting a compound represented by formula (M7) (hereinafter, referred to as intermediate compound (M7)) with an oxidizing agent.

The reaction is usually carried out in the presence of a solvent.

Examples of the solvent used in the reaction include alcohols such as methanol and ethanol, ethers such as THF, ethylene glycol dimethyl ether, tert-butyl methyl ether and 1,4-dioxane, acetic acid, water, and mixtures thereof.

Examples of the oxidizing agent used in the reaction include bromine, iodine, nitric acid, aqueous hydrogen peroxide, perchloric acid, and mixtures thereof.

In the reaction, the oxidizing agent is usually used in a ratio of 1 to 10 mol, based on 1 mol of the intermediate compound (M7).

The reaction temperature in the reaction is usually in the range of 0 to 150° C. The reaction time in the reaction is usually in the range of 0.1 to 24 hours.

After completion of the reaction, water was added to the reaction mixture, then the mixture is extracted with an organic solvent, and the organic layer is subjected to post-treatment operations such as drying and concentration, whereby the present compound (1-H1-Q=S) can be isolated. The isolated present compound (1-H1-Q=S) also can be further purified by chromatography, recrystallization, or the like.

(Production Method 5)

A compound in which Het is H2 and Q is an oxygen atom in the formula (1) (hereinafter, referred to as present compound (1-H2-Q=O)) can be produced by reacting a compound represented by formula (M9) (hereinafter, referred to as intermediate compound (M9)) with a dehydrating agent.

acetonitrile, aprotic polar solvents such as DMF, NMP and DMSO, and mixtures thereof.

The reaction can be also carried out by adding a base, as necessary. The base includes alkali metal carbonates such as sodium carbonate and potassium carbonate, tertiary amines such as triethylamine and N,N-diisopropylethylamine, and nitrogen-containing aromatic compounds such as pyridine and 4-dimethylaminopyridine, and the like.

In the reaction, the intermediate compound (M8) is usually used in a ratio of 0.8 to 1.2 mol, and the base is usually used in a ratio of 1 to 2 mol, based on 1 mol of the intermediate compound (M5).

The reaction temperature is usually in the range of −20 to 200° C. The reaction time is usually in the range of 0.1 to 24 hours.

After completion of the reaction, water was added to the reaction mixture, then the mixture is extracted with an organic solvent, and the organic layer is subjected to post-treatment operations such as drying and concentration, whereby the intermediate compound (M9) can be isolated. The isolated intermediate compound (M9) also can be further purified by chromatography, recrystallization, or the like.

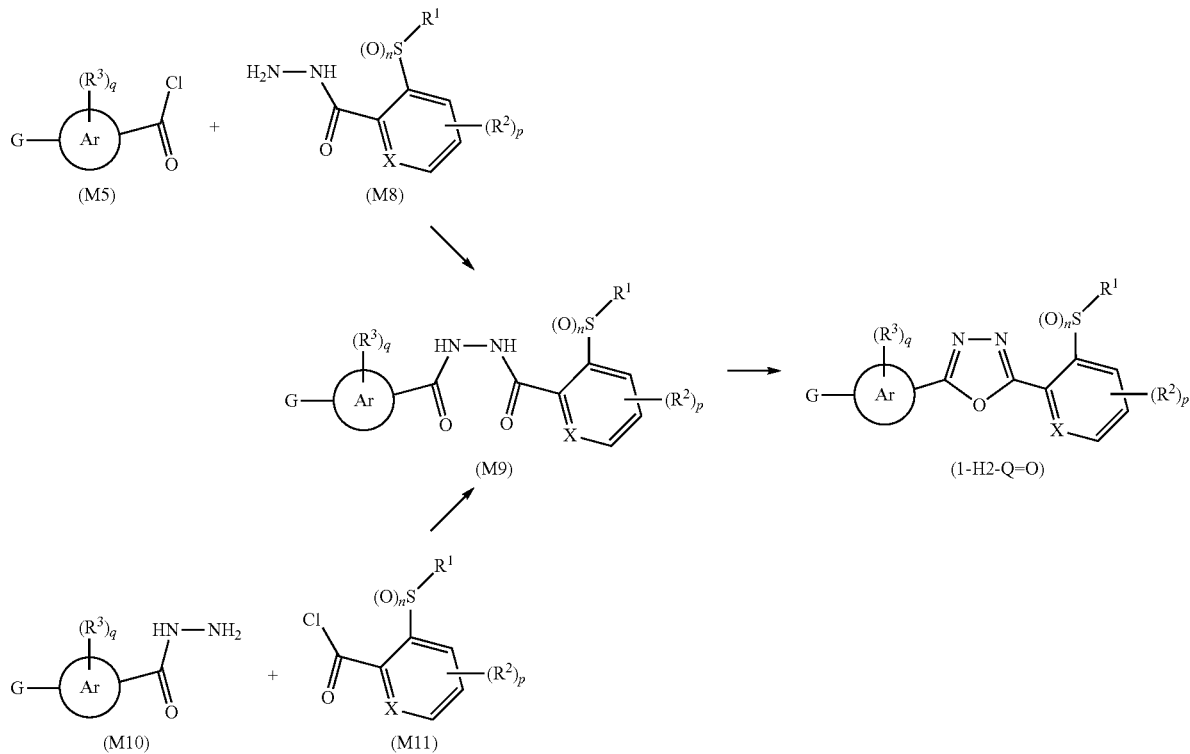

wherein symbols represent the same meaning as in the formula (1).

The intermediate compound (M9) can be produced by reacting the intermediate compound (M5) with the intermediate compound (M8).

The reaction is usually carried out in the presence of a solvent. Examples of the solvent include ethers such as THF, ethylene glycol dimethyl ether, tert-butyl methyl ether and 1,4-dioxane, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as Also, the intermediate compound (M9) can be produced, using a compound represented by formula (M11) (hereinafter, referred to as intermediate compound (M11)), in place of the intermediate compound (M5), and using a compound represented by formula (M10) (hereinafter, referred to as intermediate compound (M10)), in place of the intermediate compound (M8), in accordance with the method described above.

The present compound (1-H2-Q=O) can be produced by reacting the intermediate compound (M9) with a dehydrating agent.

The reaction is usually carried out in the presence of a solvent. Examples of the solvent include ethers such as THF, ethylene glycol dimethyl ether, tert-butyl methyl ether and 1,4-dioxane, aliphatic hydrocarbons such as hexane, heptane and octane, aromatic hydrocarbons such as toluene and xylene, halogenated hydrocarbons such as chlorobenzene, nitriles such as acetonitrile, aprotic polar solvents such as DMF, NMP and DMSO, and mixtures thereof.

Examples of the dehydrating agent include chlorinating agents such as thionyl chloride, phosphorus oxychloride and phosphorus pentachloride, and acid anhydrides such as acetic anhydride and trifluoromethanesulfonic anhydride.

In the reaction, the dehydrating agent is usually used in a ratio of 1 to 10 mol, based on 1 mol of the intermediate compound (M9).

The reaction temperature is usually in the range of 0° C. to 200° C. The reaction time is usually in the range of 0.1 to 24 hours.

After completion of the reaction, water was added to the reaction mixture, then the mixture is extracted with an organic solvent, and the organic layer is subjected to post-treatment operations such as drying and concentration, whereby the present compound (1-H2-Q=O) can be isolated. The isolated present compound (1-H2-Q=O) also can be further purified by chromatography, recrystallization, or the like.

(Production Method 6)

A compound in which Het is H2 and Q is a sulfur atom in the formula (1) (hereinafter, referred to as present compound (1-H2-Q=S)) can be produced by cyclizing the intermediate compound (M9) in the presence of a sulfurizing agent.

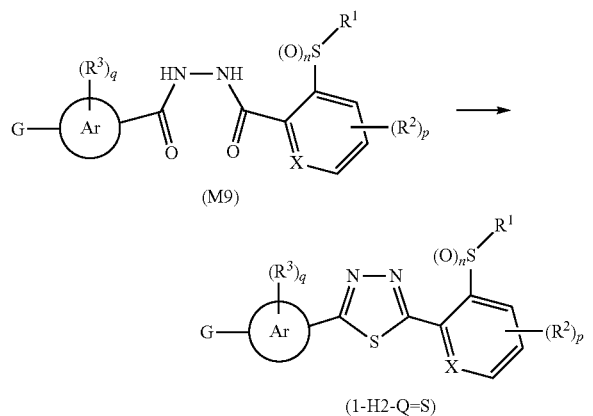

wherein symbols represent the same meaning as in the formula (1).

The reaction is usually carried out in the presence of a solvent. Examples of the solvent include ethers such as THF, ethylene glycol dimethyl ether, tert-butyl methyl ether and 1,4-dioxane, aliphatic hydrocarbons such as hexane, heptane and octane, aromatic hydrocarbons such as toluene and xylene, halogenated hydrocarbons such as chlorobenzene, and mixtures thereof.

Examples of the sulfurizing agent used in the reaction include diphosphorus pentasulfide, 2,4-bis(4-methoxyphenyl)-1,3,2,4-dithiadiphosphetane-2,4-disulfide (hereinafter referred to as Lawesson's reagent), and the like.

In the reaction, the sulfurizing agent is usually used in a ratio of 1 to 10 mol, based on 1 mol of the intermediate compound (M9).

The reaction temperature is usually in the range of 0° C. to 200° C. The reaction time is usually in the range of 0.1 to 24 hours.

After completion of the reaction, water was added to the reaction mixture, then the mixture is extracted with an organic solvent, and the organic layer is subjected to post-treatment operations such as drying and concentration, whereby the present compound (1-H2-Q=O) can be isolated. The isolated present compound (1-H2-Q=O) also can be further purified by chromatography, recrystallization, or the like.

(Production Method 7)

A compound in which Het is H3 and Q is an oxygen atom in the formula (1) (hereinafter, referred to as present compound (1-H3-Q=O)) can be produced by reacting a compound represented by formula (M13) (hereinafter, referred to as intermediate compound (M13)) with a compound represented by formula (M11) (hereinafter, referred to as intermediate compound (M11)).

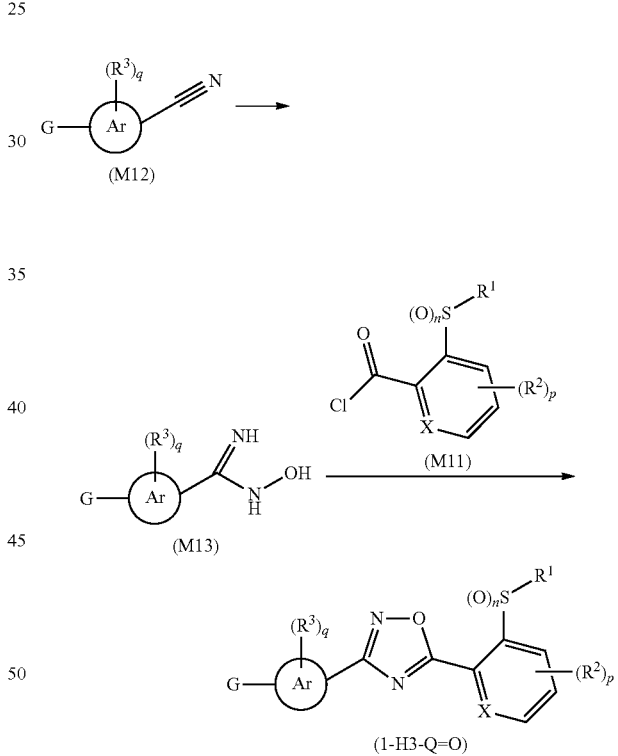

wherein symbols represent the same meaning as in the formula (1).

The reaction can be carried out according to the method described in Production Method 3.

(Production Method 8)

A compound in which Het is H3 and Q is a sulfur atom in the formula (1) (hereinafter, referred to as present compound (1-H3-Q=S)) can be produced by reacting a compound represented by formula (M15) (hereinafter, referred to as intermediate compound (M15)) with an oxidizing agent.

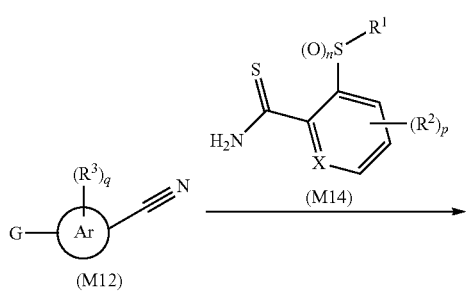

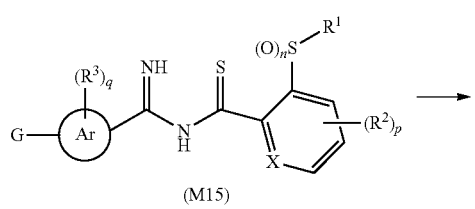

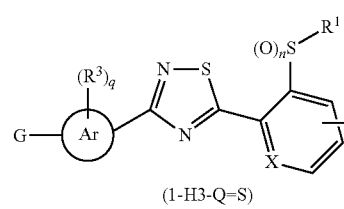

wherein symbols represent the same meaning as in the formula (1).

The reaction can be carried out in accordance with the method described in Production Method 4.

(Production Method 9)

A compound in which Het is H1 and Q is an oxygen atom in the intermediate compound (M1) (hereinafter, referred to as intermediate compound (M1-H1-Q=O)) can be produced by reacting a compound represented by formula (M17) (hereinafter, referred to as intermediate compound (M17)) with the intermediate compound (M5).

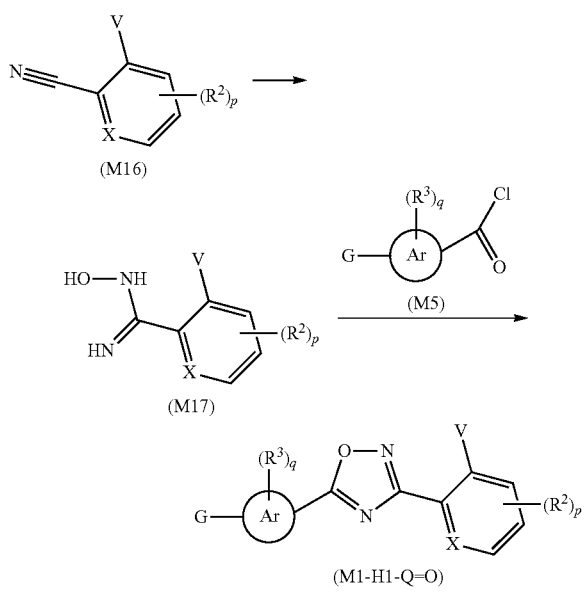

wherein symbols represent the same meaning as described above.

The intermediate compound (M17) can be produced, using a compound represented by formula (M16) (hereinafter, referred to as intermediate compound (M16)) in place of the intermediate compound (M3), in accordance with the method of Production Method 3.

The intermediate compound (M1-H1-Q=O) can be produced, using the intermediate compound (M17) in place of the intermediate compound (M4), in accordance with the method described in Production Method 3.

(Production Method 10)

A compound in which Het is H1 and Q is a sulfur atom in the intermediate compound (M1) (hereinafter, referred to as intermediate compound (M1-H1-Q=S)) can be produced by reacting a compound represented by formula (M18) (hereinafter, referred to as intermediate compound (M18)) with an oxidizing agent.

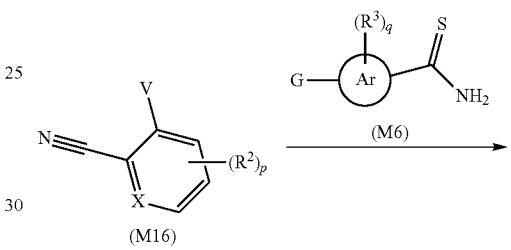

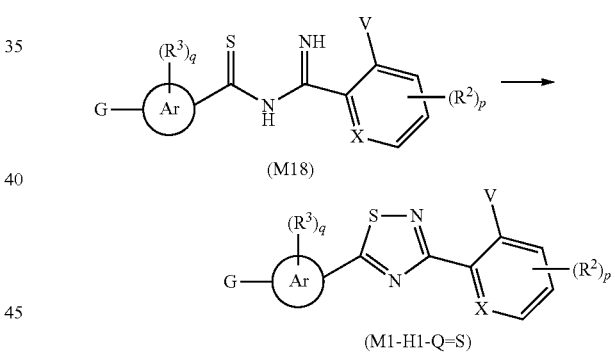

wherein symbols represent the same meaning as described above.

The intermediate compound (M18) can be produced, using the intermediate compound (M16) in place of the intermediate compound (M3), in accordance with the method described in Production Method 4.

The intermediate compound (M1-H1-Q=S) can be produced, using the intermediate compound (M18) in place of the intermediate compound (M7), in accordance with the method described in Production Method 4.

(Production Method 11)

A compound in which Het is H2 and Q is an oxygen atom in the intermediate compound (M1) (hereinafter, referred to as intermediate compound (M1-H2-Q=O)) can be produced by reacting a compound represented by formula (M20) (hereinafter, referred to as intermediate compound (M20)) with a dehydrating agent.

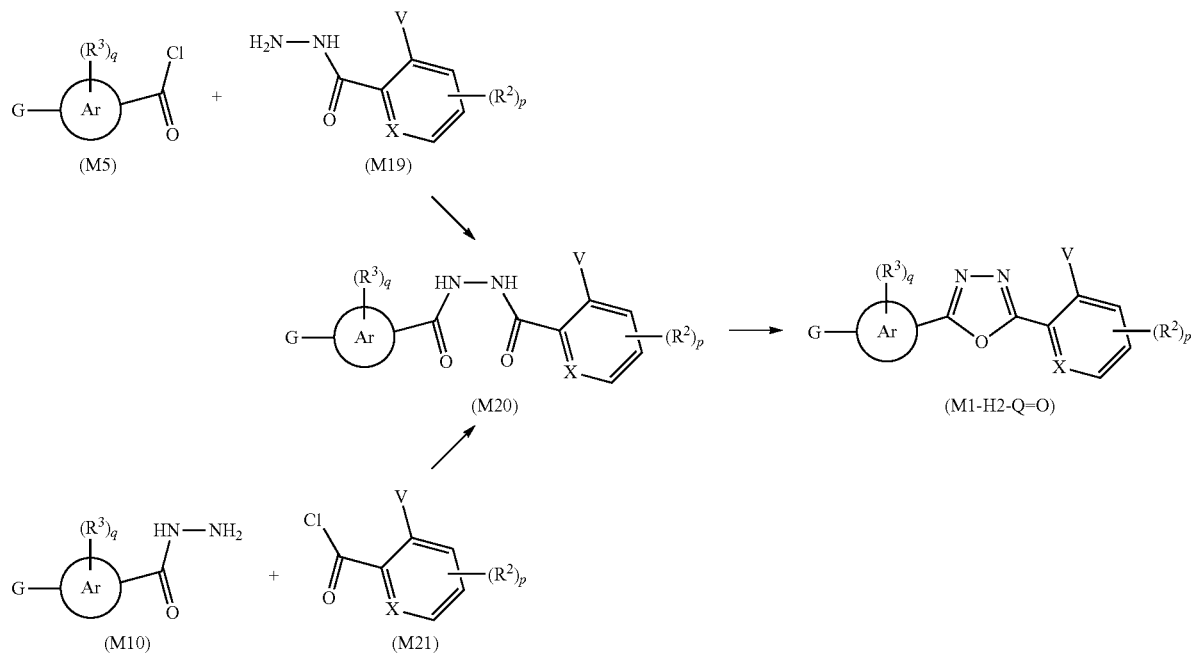

wherein symbols represent the same meaning as described above.

The intermediate compound (M20) can be produced, using a compound represented by formula (M19) (hereinafter, referred to as intermediate compound (M19)) in place of the intermediate compound (M8), in accordance with the method described in Production Method 5.

The intermediate compound (M20) can be produced, using a compound represented by formula (M21) (hereinafter, referred to as intermediate compound (M21)) in place of the intermediate compound (M11), in accordance with the method described in Production Method 5.

The intermediate compound (M1-H2-Q=O) can be produced, using the intermediate compound (M20) in place of the intermediate compound (M9), in accordance with the method described in Production Method 5.

(Production Method 12)

A compound in which Het is H2 and Q is a sulfur atom in the intermediate compound (M1) (hereinafter, referred to as intermediate compound (M1-H2-Q=S)) can be produced by cyclizing the intermediate compound (M20) in the presence of a sulfurizing agent.

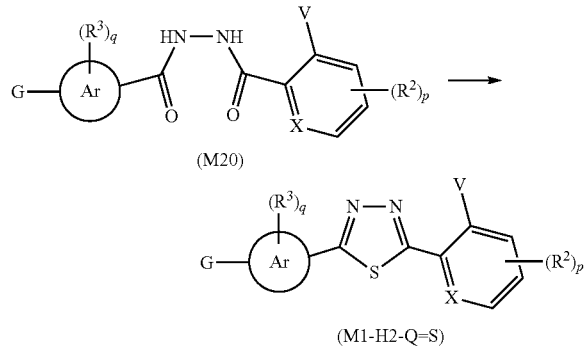

wherein symbols represent the same meaning as described above.

The intermediate compound (M1-H2-Q=S) can be produced, using the intermediate compound (M20) in place of the intermediate compound (M9), in accordance with the method described in Production Method 6.

(Production Method 13)

A compound in which Het is H3 and Q is an oxygen atom in the intermediate compound (M1) (hereinafter, referred to as intermediate compound (M1-H3-Q=O)) can be produced by reacting the intermediate compound (M13) with the intermediate compound (M21).

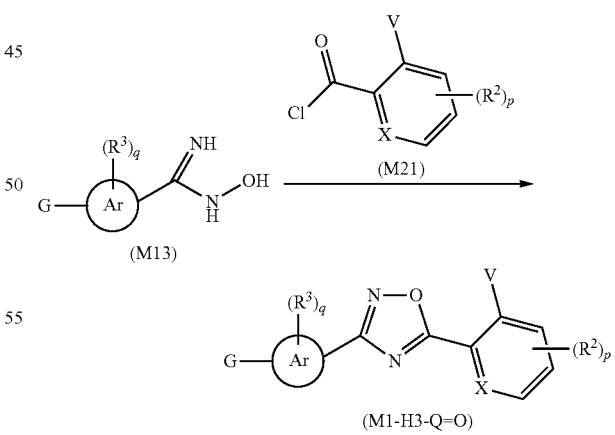

wherein symbols represent the same meaning as described above.

The intermediate compound (M1-H3-Q=O) can be produced, using the intermediate compound (M21) in place of the intermediate compound (M11), in accordance with the method described in Production Method 7.

(Production Method 14)

A compound in which Het is H3 and Q is a sulfur atom in the intermediate compound (M1) (hereinafter, referred to as intermediate compound (M1-H3-Q=S)) can be produced by reacting a compound represented by formula (M23) (hereinafter, referred to as intermediate compound (M23)) with an oxidizing agent.

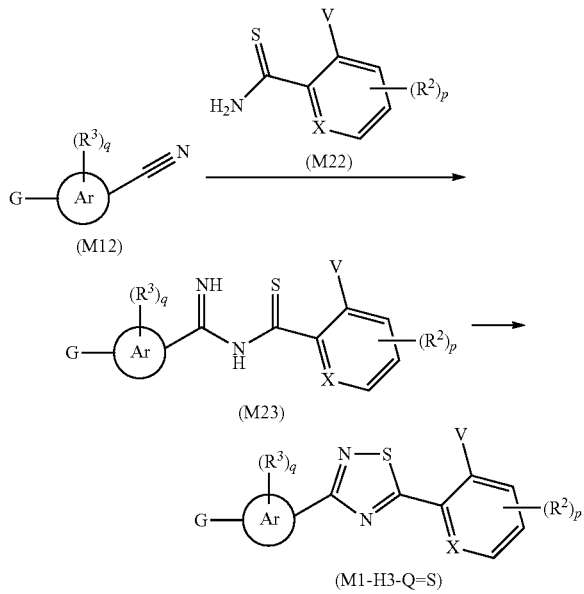

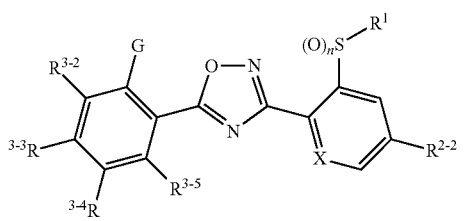

(M1-H3-Q=S)

wherein symbols represent the same meaning as described above.

The intermediate compound (M23) can be produced, using a compound represented by formula (M23) (hereinafter, referred to as intermediate compound (M22)) in place of the intermediate compound (M14), in accordance with the method described in Production Method 8.

The intermediate compound (M1-H3-Q=S) can be produced, using the intermediate compound (M23) in place of the intermediate compound (M15), in accordance with the method described in Production Method 8.

Next, specific examples of the compound of the present invention are shown below.

In compounds represented by formula (3-1), (3-1)

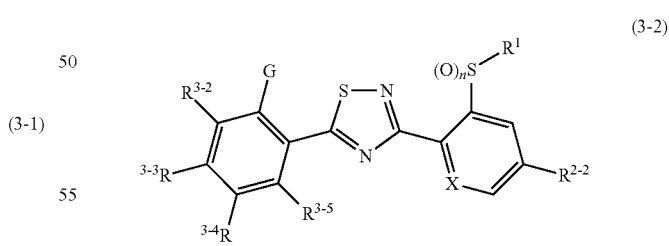

the compounds of the present invention wherein X is N, $R^{2-2}$ is H, and $R^1$, n, X, G, $R^{3-2}$, $R^{3-3}$, $R^{3-4}$ and $R^{3-5}$ are any of the combinations shown in [Table A] [in the table, Pr represents propyl, Bu represents butyl, Pen represents pentyl, and cPr represents cyclopropyl.].

TABLE A

| $R^1$ | n | G | $R^{3-2}$ | $R^{3-3}$ | $R^{3-4}$ | $R^{3-5}$ |
|---|---|---|---|---|---|---|
| $CH_2CH_3$ | 0 | $CF_3$ | H | H | H | H |
| $CH_2CH_3$ | 1 | $CF_3$ | H | H | H | H |
| $CH_2CH_3$ | 2 | $CF_3$ | H | H | H | H |
| $CH_2CH_3$ | 2 | $SCF_3$ | H | H | H | H |
| $CH_2CH_3$ | 2 | $S(O)CF_3$ | H | H | H | H |
| $CH_2CH_3$ | 2 | $S(O)_2CF_3$ | H | H | H | H |
| $CH_2CH_3$ | 2 | $OS(O)_2CF_3$ | H | H | H | H |
| $CH_2CH_3$ | 2 | $CF_3$ | F | H | H | H |
| $CH_2CH_3$ | 2 | $CF_3$ | Cl | H | H | H |
| $CH_2CH_3$ | 2 | $CF_3$ | H | F | H | H |
| $CH_2CH_3$ | 2 | $CF_3$ | H | Cl | H | H |
| $CH_2CH_3$ | 2 | $CF_3$ | H | Br | H | H |
| $CH_2CH_3$ | 2 | $CF_3$ | H | $CF_3$ | H | H |
| $CH_2CH_3$ | 2 | $CF_3$ | H | $CH_3$ | H | H |
| $CH_2CH_3$ | 2 | $CF_3$ | H | $OCH_3$ | H | H |
| $CH_2CH_3$ | 2 | $CF_3$ | H | $NH_2$ | H | H |
| $CH_2CH_3$ | 2 | $CF_3$ | H | CN | H | H |
| $CH_2CH_3$ | 2 | $CF_3$ | H | $NO_2$ | H | H |
| $CH_2CH_3$ | 2 | $CF_3$ | H | H | F | H |
| $CH_2CH_3$ | 2 | $CF_3$ | H | H | Cl | H |
| $CH_2CH_3$ | 2 | $CF_3$ | H | H | Br | H |
| $CH_2CH_3$ | 2 | $CF_3$ | H | H | $CF_3$ | H |
| $CH_2CH_3$ | 2 | $CF_3$ | H | H | $CH_3$ | H |
| $CH_2CH_3$ | 2 | $CF_3$ | H | H | $OCH_3$ | H |
| $CH_2CH_3$ | 2 | $CF_3$ | H | H | H | F |
| $CH_2CH_3$ | 2 | $CF_3$ | H | H | H | Cl |
| $CH_2CH_3$ | 2 | $CF_3$ | H | H | H | Br |
| $CH_2CH_3$ | 2 | $CF_3$ | H | H | H | $CF_3$ |
| $CH_3$ | 2 | $OCF_3$ | H | H | H | H |
| Pr | 2 | cPr | H | H | H | H |
| Bu | 2 | Cl | H | $SCH_3$ | H | H |
| Pen | 2 | $NHSO_2CH_3$ | H | H | H | H |
| $CH_2CH=CH_2$ | 2 | $CF_2CF_3$ | H | H | H | H |
| cPr | 2 | $CF_2CF_2CF_3$ | H | H | H | H |

In the compounds represented by the formula (3-1), the compounds of the present invention wherein X is N, $R^{2-2}$ is $CF_3$, and $R^1$, n, X, G, $R^{3-2}$, $R^{3-3}$, $R^{3-4}$ and $R^{3-5}$ are any of the combinations shown in [Table A].

In the compounds represented by the formula (3-1), the compounds of the present invention wherein X is CH, $R^{2-2}$ is H, and $R^1$, n, X, G, $R^{3-2}$, $R^{3-3}$, $R^{3-4}$ and $R^{3-5}$ are any of the combinations shown in [Table A].

In the compounds represented by the formula (3-1), the compounds of the present invention wherein X is CH, $R^{2-2}$ is $CF_3$, and $R^1$, n, X, G, $R^{3-2}$, $R^{3-3}$, $R^{3-4}$ and $R^{3-5}$ are any of the combinations shown in [Table A].

In compounds represented by formula (3-2), (3-2)

the compounds of the present invention wherein X is N, $R^{2-2}$ is H, and $R^1$, n, X, G, $R^{3-2}$, $R^{3-3}$, $R^{3-4}$ and $R^{3-5}$ are any of the combinations shown in [Table A].

In the compounds represented by the formula (3-2), the compounds of the present invention wherein X is N, $R^{2-2}$ is $CF_3$, and $R^1$, n, X, G, $R^{3-2}$, $R^{3-3}$, $R^{3-4}$ and $R^{3-5}$ are any of the combinations shown in [Table A].

In the compounds represented by the formula (3-2), the compounds of the present invention wherein X is CH, $R^{2-2}$ is H, and $R^1$, n, X, G, $R^{3-2}$, $R^{3-3}$, $R^{3-4}$ and $R^{3-5}$ are any of the combinations shown in [Table A].

In the compounds represented by the formula (3-2), the compounds of the present invention wherein X is CH, $R^{2-2}$ is $CF_3$, and $R^1$, n, X, G, $R^{3-2}$, $R^{3-3}$, $R^{3-4}$ and $R^{3-5}$ are any of the combinations shown in [Table A].

In compounds represented by formula (3-3),

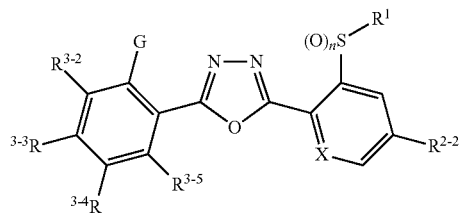

(3-3)

the compounds of the present invention wherein X is N, $R^{2-2}$ is H, and $R^1$, n, X, G, $R^{3-2}$, $R^{3-3}$, $R^{3-4}$ and $R^{3-5}$ are any of the combinations shown in [Table A].

In the compounds represented by the formula (3-3), the compounds of the present invention wherein X is N, $R^{2-2}$ is $CF_3$, and $R^1$, n, X, G, $R^{3-2}$, $R^{3-3}$, $R^{3-4}$ and $R^{3-5}$ are any of the combinations shown in [Table A].

In the compounds represented by the formula (3-3), the compounds of the present invention wherein X is CH, $R^{2-2}$ is H, and $R^1$, n, X, G, $R^{3-2}$, $R^{3-3}$, $R^{3-4}$ and $R^{3-5}$ are any of the combinations shown in [Table A].

In the compounds represented by the formula (3-3), the compounds of the present invention wherein X is CH, $R^{2-2}$ is $CF_3$, and $R^1$, n, X, G, $R^{3-2}$, $R^{3-3}$, R and $R^{3-4}$ and $R^{3-5}$ any of the combinations shown in [Table A].

In compounds represented by formula (3-4),

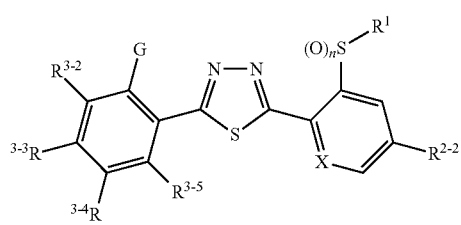

(3-4)

the compounds of the present invention wherein X is N, $R^{2-2}$ is H, and $R^1$, n, X, G, $R^{3-2}$, $R^{3-3}$, $R^{3-4}$ and $R^{3-5}$ are any of the combinations shown in [Table A].

In the compounds represented by the formula (3-4), the compounds of the present invention wherein X is N, $R^{2-2}$ is $CF_3$, and $R^1$, n, X, G, $R^{3-2}$, $R^{3-3}$, $R^{3-4}$ and $R^{3-5}$ axe any of the combinations shown in [Table A].

In the compounds represented by the formula (3-4), the compounds of the present invention wherein X is CH, $R^{2-2}$ is H, and $R^1$, n, X, G, $R^{3-2}$, $R^{3-3}$, $R^{3-4}$ and $R^{3-5}$ are any of the combinations shown in [Table A].

In the compounds represented by the formula (3-4), the compounds of the present invention wherein X is CH, $R^{2-2}$ is $CF_3$, and $R^1$, n, X, G, $R^{3-2}$, $R^{3-3}$, $R^{3-4}$ and $R^{3-5}$ are any of the combinations shown in [Table A].

In compounds represented by formula (3-5),

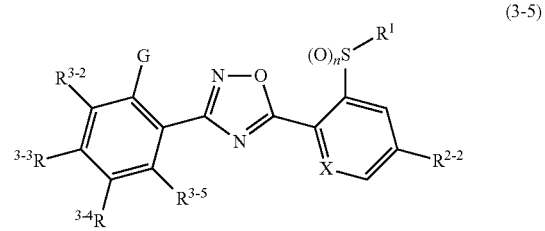

(3-5)

the compounds of the present invention wherein X is N, $R^{2-2}$ is H, and $R^1$, n, X, G, $R^{3-2}$, $R^{3-3}$, $R^{3-4}$ and $R^{3-5}$ are any of the combinations shown in [Table A].

In the compounds represented by the formula (3-5), the compounds of the present invention wherein X is N, $R^{2-2}$ is $CF_3$, and $R^1$, n, X, G, $R^{3-2}$, $R^{3-3}$, $R^{3-4}$ and $R^{3-5}$ are any of the combinations shown in [Table A].

In the compounds represented by the formula (3-5), the compounds of the present invention wherein X is CH, $R^{2-2}$ is H, and $R^1$, n, X, G, $R^{3-2}$, $R^{3-3}$, $R^{3-4}$ and $R^{3-5}$ axe any of the combinations shown in [Table A].

In the compounds represented by the formula (3-5), the compounds of the present invention wherein X is CH, $R^{2-2}$ is $CF_3$, and $R^1$, n, X, G, $R^{3-2}$, $R^{3-3}$, $R^{3-4}$ and $R^{3-5}$ are any of the combinations shown in [Table A].

In compounds represented by formula (3-6),

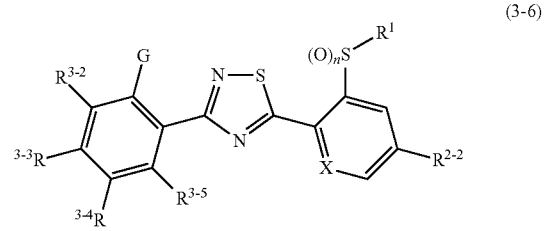

(3-6)

the compounds of the present invention wherein X is N, $R^{2-2}$ is H, and $R^1$, n, X, G, $R^{3-2}$, $R^{3-3}$, $R^{3-4}$ and $R^{3-5}$ are any of the combinations shown in [Table A].

In the compounds represented by the formula (3-6), the compounds of the present invention wherein X is N, $R^{2-2}$ is $CF_3$, and $R^1$, n, X, G, $R^{3-2}$, $R^{3-3}$, $R^{3-4}$ and $R^{3-5}$ are any of the combinations shown in [Table A].

In the compounds represented by the formula (3-6), the compounds of the present invention wherein X is CH, $R^{2-2}$ is H, and $R^1$, n, X, G, $R^{3-2}$, $R^{3-3}$, $R^{3-4}$ and $R^{3-5}$ are any of the combinations shown in [Table A].

In the compounds represented by the formula (3-6), the compounds of the present invention wherein X is CH, $R^{2-2}$ is $CF_3$, and $R^1$, n, X, G, $R^{3-2}$, $R^{3-3}$, $R^{3-4}$ and $R^{3-5}$ axe any of the combinations shown in [Table A].

In compounds represented by formula (4-1),

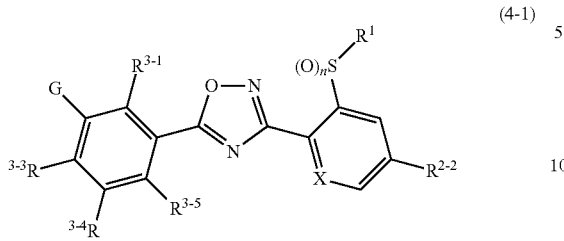
(4-1)

the compounds of the present invention wherein X is N, $R^{2-2}$ is H, and $R^1$, n, G, $R^{3-1}$, $R^{3-3}$, $R^{3-4}$ and $R^{3-5}$ are any of the combinations shown in [Table B].

TABLE B

| $R^1$ | n | $G^2$ | $R^{3-1}$ | $R^{3-3}$ | $R^{3-4}$ | $R^{3-5}$ |
|---|---|---|---|---|---|---|
| $CH_2CH_3$ | 0 | $CF_3$ | H | H | H | H |
| $CH_2CH_3$ | 1 | $CF_3$ | H | H | H | H |
| $CH_2CH_3$ | 2 | $CF_3$ | H | H | H | H |
| $CH_2CH_3$ | 2 | $SCF_3$ | H | H | H | H |
| $CH_2CH_3$ | 2 | $S(O)CF_3$ | H | H | H | H |
| $CH_2CH_3$ | 2 | $S(O)_2CF_3$ | H | H | H | H |
| $CH_2CH_3$ | 2 | $OS(O)_2CF_3$ | H | H | H | H |
| $CH_2CH_3$ | 2 | $CF_3$ | F | H | H | H |
| $CH_2CH_3$ | 2 | $CF_3$ | Cl | H | H | H |
| $CH_2CH_3$ | 2 | $CF_3$ | Br | H | H | H |
| $CH_2CH_3$ | 2 | $CF_3$ | H | F | H | H |
| $CH_2CH_3$ | 2 | $CF_3$ | H | Cl | H | H |
| $CH_2CH_3$ | 2 | $CF_3$ | H | Br | H | H |
| $CH_2CH_3$ | 2 | $CF_3$ | H | $CF_3$ | H | H |
| $CH_2CH_3$ | 2 | $CF_3$ | H | $CH_3$ | H | H |
| $CH_2CH_3$ | 2 | $CF_3$ | H | $OCH_3$ | H | H |
| $CH_2CH_3$ | 2 | $CF_3$ | H | $NO_2$ | H | H |
| $CH_2CH_3$ | 2 | $CF_3$ | H | H | F | H |
| $CH_2CH_3$ | 2 | $CF_3$ | H | H | Cl | H |
| $CH_2CH_3$ | 2 | $CF_3$ | H | H | Br | H |
| $CH_2CH_3$ | 0 | $CF_3$ | H | H | $CF_3$ | H |
| $CH_2CH_3$ | 1 | $CF_3$ | H | H | $CF_3$ | H |
| $CH_2CH_3$ | 2 | $CF_3$ | H | H | $CF_3$ | H |
| $CH_2CH_3$ | 2 | $CF_3$ | H | H | $CH_3$ | H |
| $CH_2CH_3$ | 2 | $CF_3$ | H | H | $OCH_3$ | H |
| $CH_2CH_3$ | 2 | $CF_3$ | H | H | CN | H |
| $CH_2CH_3$ | 2 | $CF_3$ | H | H | $NO_2$ | H |
| $CH_2CH_3$ | 2 | $CF_3$ | H | H | $NH_2$ | H |
| $CH_2CH_3$ | 2 | $CF_3$ | H | H | $C_6H_5$ | H |
| $CH_2CH_3$ | 2 | $CF_3$ | H | H | H | F |
| $CH_2CH_3$ | 2 | $CF_3$ | H | H | H | Cl |
| $CH_2CH_3$ | 2 | $CF_3$ | H | H | H | Br |
| $CH_2CH_3$ | 2 | $CF_3$ | H | F | F | H |
| $CH_2CH_3$ | 2 | $CF_3$ | H | F | Cl | H |
| $CH_2CH_3$ | 2 | $CF_2CF_3$ | H | H | H | H |
| $CH_2CH_3$ | 2 | $CF_2CF_2CF_3$ | H | H | H | H |
| $CH_2CH_3$ | 2 | $CF_3$ | H | H | $CF_2CF_3$ | H |
| $CH_2CH_3$ | 2 | $CF_3$ | H | H | $CF_2CF_2CF_3$ | H |

In the compounds represented by the formula (4-1), the compounds of the present invention wherein X is N, $R^{2-2}$ is $CF_3$, and $R^1$, n, G, $R^{3-1}$, $R^{3-3}$, $R^{3-4}$ and $R^{3-5}$ are any of the combinations shown in [Table B].

In the compounds represented by the formula (4-1), the compounds of the present invention wherein X is CH, $R^{2-2}$ is H, and $R^1$, n, G, $R^{3-1}$, $R^{3-3}$, $R^{3-4}$ and $R^{3-5}$ are any of the combinations shown in [Table B].

In the compounds represented by the formula (4-1), the compounds of the present invention wherein X is CH, $R^{2-2}$ is $CF_3$, and $R^1$, n, G, $R^{3-1}$, $R^{3-3}$, $R^{3-4}$ and $R^{3-5}$ are any of the combinations shown in [Table B].

In compounds represented by formula (4-2),

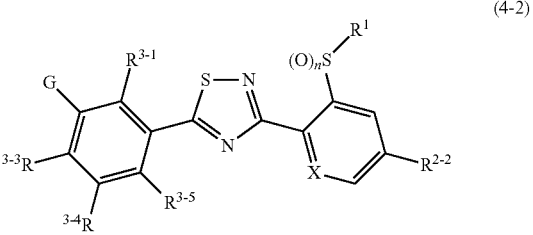
(4-2)

the compounds of the present invention wherein X is N, $R^{2-2}$ is H, and $R^1$, n, G, $R^{3-1}$, $R^{3-3}$, $R^{3-4}$ and $R^{3-5}$ axe any of the combinations shown in [Table B].

In the compounds represented by the formula (4-2), the compounds of the present invention wherein X is N, $R^{2-2}$ is $CF_3$, and $R^1$, n, G, $R^{3-1}$, $R^{3-3}$, $R^{3-4}$ and $R^{3-5}$ are any of the combinations shown in [Table B].

In the compounds represented by the formula (4-2), the compounds of the present invention wherein X is CH, $R^{2-2}$ is H, and $R^1$, n, G, $R^{3-1}$, $R^{3-3}$, $R^{3-4}$ and $R^{3-5}$ are any of the combinations shown in [Table B].

In the compounds represented by the formula (4-2), the compounds of the present invention wherein X is CH, $R^{2-2}$ is $CF_3$, and $R^1$, n, G, $R^{3-1}$, $R^{3-3}$, $R^{3-4}$ and $R^{3-5}$ are any of the combinations shown in [Table B].

In compounds represented by formula (4-3),

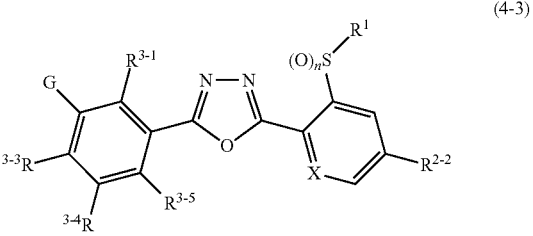
(4-3)

the compounds of the present invention wherein X is N, $R^{2-2}$ is H, and $R^1$, n, G, $R^{3-1}$, $R^{3-3}$, $R^{3-4}$ and $R^{3-5}$ are any of the combinations shown in [Table B].

In the compounds represented by the formula (4-3), the compounds of the present invention wherein X is N, $R^{2-2}$ is $CF_3$, and $R^1$, n, G, $R^{3-1}$, $R^{3-3}$, $R^{3-4}$ and $R^{3-5}$ are any of the combinations shown in [Table B].

In the compounds represented by the formula (4-3), the compounds of the present invention wherein X is CH, $R^{2-2}$ is H, and $R^1$, n, G, $R^{3-1}$, $R^{3-3}$, $R^{3-4}$ and $R^{3-5}$ are any of the combinations shown in [Table B].

In the compounds represented by the formula (4-3), the compounds of the present invention wherein X is CH, $R^{2-2}$ is $CF_3$, and $R^1$, n, G, $R^{3-1}$, $R^{3-3}$, $R^{3-4}$ and $R^{3-5}$ are any of the combinations shown in [Table B].

In compounds represented by formula (4-4),

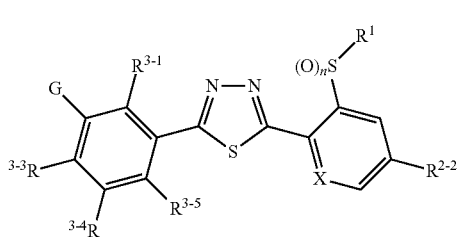

(4-4)

the compounds of the present invention wherein X is N, $R^{2-2}$ is H, and $R^1$, n, G, $R^{3-1}$, $R^{3-3}$, $R^{3-4}$ and $R^{3-5}$ are any of the combinations shown in [Table B].

In the compounds represented by the formula (4-4), the compounds of the present invention wherein X is N, $R^{2-2}$ is $CF_3$, and $R^1$, n, G, $R^{3-1}$, $R^{3-3}$, $R^{3-4}$ and $R^{3-5}$ are any of the combinations shown in [Table 8].

In the compounds represented by the formula (4-4), the compounds of the present invention wherein X is CH, $R^{2-2}$ is H, and $R^1$, n, G, $R^{3-1}$, $R^{3-3}$, $R^{3-4}$ and $R^{3-5}$ are any of the combinations shown in [Table B].

In the compounds represented by the formula (4-4), the compounds of the present invention wherein X is CH, $R^{2-2}$ is $CF_3$, and $R^1$, n, G, $R^{3-1}$, $R^{3-3}$, $R^{3-4}$ and $R^{3-5}$ are any of the combinations shown in [Table B].

In compounds represented by formula (4-5),

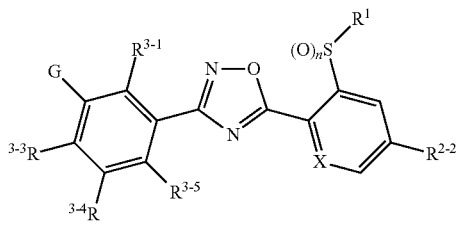

(4-5)

the compounds of the present invention wherein X is N, $R^{2-2}$ is H, and $R^1$, n, G, $R^{3-1}$, $R^{3-3}$, $R^{3-4}$ and $R^{3-5}$ are any of the combinations shown in [Table B].

In the compounds represented by the formula (4-5), the compounds of the present invention wherein X is N, $R^{2-2}$ is $CF_3$, and $R^1$, n, G, $R^{3-1}$, $R^{3-3}$, $R^{3-4}$ and $R^{3-5}$ are any of the combinations shown in [Table B].

In the compounds represented by the formula (4-5), the compounds of the present invention wherein X is CH, $R^{2-2}$ is H, and $R^1$, n, G, $R^{3-1}$, $R^{3-3}$, $R^{3-4}$ and $R^{3-5}$ are any of the combinations shown in [Table B].

In the compounds represented by the formula (4-5), the compounds of the present invention wherein X is CH, $R^{2-2}$ is $CF_3$, and $R^1$, n, G, $R^{3-1}$, $R^{3-3}$, $R^{3-4}$ and $R^{3-5}$ are any of the combinations shown in [Table B].

In compounds represented by formula (4-6),

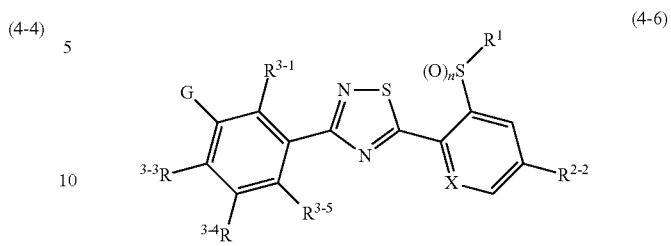

(4-6)

the compounds of the present invention wherein X is N, $R^{2-2}$ is H, and $R^1$, n, G, $R^{3-1}$, $R^{3-3}$, $R^{3-4}$ and $R^{3-5}$ are any of the combinations shown in [Table B].

In the compounds represented by the formula (4-6), the compounds of the present invention wherein X is N, $R^{2-2}$ is $CF_3$, $R^1$, n, G, $R^{3-1}$, $R^{3-3}$, $R^{3-4}$ and $R^{3-5}$ are any of the combinations shown in [Table B].

In the compounds represented by the formula (4-6), the compounds of the present invention wherein X is CH, $R^{2-2}$ is H, and $R^1$, n, G, $R^{3-1}$, $R^{3-3}$, $R^{3-4}$ and $R^{3-5}$ are any of the combinations shown in [Table B].

In the compounds represented by the formula (4-6), the compounds of the present invention wherein X is CH, $R^{2-2}$ is $CF_3$, and $R^1$, n, G, $R^{3-1}$, $R^{3-3}$, $R^{3-4}$ and $R^{3-5}$ are any of the combinations shown in [Table B].

In compounds represented by formula (5-1),

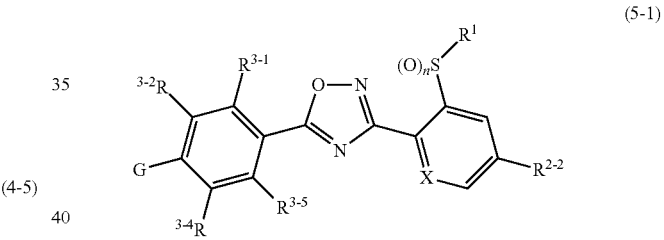

(5-1)

the compounds of the present invention wherein X is N, $R^{2-2}$ is H, and $R^1$, n, G, $R^{3-1}$, $R^{3-2}$, $R^{3-4}$ and $R^{3-5}$ are any of the combinations shown in [Table C].

TABLE C

| $R^1$ | n | G | $R^{3-1}$ | $R^{3-2}$ | $R^{3-4}$ | $R^{3-5}$ |
|---|---|---|---|---|---|---|
| $CH_2CH_3$ | 0 | $CF_3$ | H | H | H | H |
| $CH_2CH_3$ | 1 | $CF_3$ | H | H | H | H |
| $CH_2CH_3$ | 2 | $CF_3$ | H | H | H | H |
| $CH_2CH_3$ | 2 | $SCF_3$ | H | H | H | H |
| $CH_2CH_3$ | 2 | $S(O)CF_3$ | H | H | H | H |
| $CH_2CH_3$ | 2 | $S(O)_2CF_3$ | H | H | H | H |
| $CH_2CH_3$ | 2 | $OS(O)_2CF_3$ | H | H | H | H |
| $CH_2CH_3$ | 2 | $CF_3$ | F | H | H | H |
| $CH_2CH_3$ | 2 | $CF_3$ | Cl | H | H | H |
| $CH_2CH_3$ | 2 | $CF_3$ | Br | H | H | H |
| $CH_2CH_3$ | 2 | $CF_3$ | $CH_3$ | H | H | H |
| $CH_2CH_3$ | 2 | $CF_3$ | $OCH_3$ | H | H | H |
| $CH_2CH_3$ | 2 | $CF_3$ | CN | H | H | H |
| $CH_2CH_3$ | 2 | $CF_3$ | $NO_2$ | H | H | H |
| $CH_2CH_3$ | 2 | $CF_3$ | H | F | H | H |
| $CH_2CH_3$ | 2 | $CF_3$ | H | Cl | H | H |
| $CH_2CH_3$ | 2 | $CF_3$ | H | Br | H | H |
| $CH_2CH_3$ | 2 | $CF_3$ | H | $CH_3$ | H | H |
| $CH_2CH_3$ | 2 | $CF_3$ | H | $OCH_3$ | H | H |
| $CH_2CH_3$ | 2 | $CF_3$ | H | CN | H | H |
| $CH_2CH_3$ | 2 | $CF_3$ | H | $NO_2$ | H | H |

TABLE C-continued

| $R^1$ | n | G | $R^{3-1}$ | $R^{3-2}$ | $R^{3-4}$ | $R^{3-5}$ |
|---|---|---|---|---|---|---|
| $CH_2CH_3$ | 2 | $CF_3$ | H | H | F | H |
| $CH_2CH_3$ | 2 | $CF_3$ | H | H | Cl | H |
| $CH_2CH_3$ | 2 | $CF_3$ | H | H | Br | H |
| $CH_2CH_3$ | 2 | $CF_2CF_3$ | H | H | H | H |
| $CH_2CH_3$ | 2 | $CF_2CF_2CF_3$ | H | H | H | H |

In the compounds represented by the formula (5-1), the compounds of the present invention wherein X is N, $R^{2-2}$ is $CF_3$, and $R^1$, n, G, $R^{3-1}$, $R^{3-2}$, $R^{3-4}$ and $R^{3-5}$ are any of the combinations shown in [Table C].

In the compounds represented by the formula (5-1), the compounds of the present invention wherein X is CH, $R^{2-2}$ is H, and $R^1$, n, G, $R^{3-1}$, $R^{3-2}$, $R^{3-4}$ and $R^{3-5}$ are any of the combinations shown in [Table C].

In the compounds represented by the formula (5-1), the compounds of the present invention wherein X is CH, $R^{2-2}$ is $CF_3$, and $R^1$, n, G, $R^{3-1}$, $R^{3-2}$, $R^{3-4}$ and $R^{3-5}$ are any of the combinations shown in [Table C].

In compounds represented by formula (5-2), (5-2)

the compounds of the present invention wherein X is N, $R^{2-2}$ is H, and $R^1$, n, G, $R^{3-1}$, $R^{3-2}$, $R^{3-4}$ and $R^{3-5}$ are any of the combinations shown in [Table C].

In the compounds represented by the formula (5-2), the compounds of the present invention wherein X is N, $R^{2-2}$ is $CF_3$, and $R^1$, n, G, $R^{3-1}$, $R^{3-2}$, $R^{3-4}$ and $R^{3-5}$ are any of the combinations shown in [Table C].

In the compounds represented by the formula (5-2), the compounds of the present invention wherein X is CH, $R^{2-2}$ is H, and $R^1$, n, G, $R^{3-1}$, $R^{3-2}$, $R^{3-4}$ and $R^{3-5}$ are any of the combinations shown in [Table C].

In the compounds represented by the formula (5-2), the compounds of the present invention wherein X is CH, $R^{2-2}$ is $CF_3$, and $R^1$, n, G, $R^{3-1}$, $R^{3-2}$, $R^{3-4}$ and $R^{3-5}$ are any of the combinations shown in [Table C].

In compounds represented by formula (5-3), (5-3)

the compounds of the present invention wherein X is N, $R^{2-2}$ is H, and $R^1$, n, G, $R^{3-1}$, $R^{3-2}$, $R^{3-4}$ and $R^{3-5}$ are any of the combinations shown in [Table C].

In the compounds represented by the formula (5-3), the compounds of the present invention wherein X is N, $R^{2-2}$ is $CF_3$, and $R^1$, n, G, $R^{3-1}$, $R^{3-2}$, $R^{3-4}$ and $R^{3-5}$ are any of the combinations shown in [Table C].

In the compounds represented by the formula (5-3), the compounds of the present invention wherein X is CH, $R^{2-2}$ is H, and $R^1$, n, G, $R^{3-1}$, $R^{3-2}$, $R^{3-4}$ and $R^{3-5}$ are any of the combinations shown in [Table C].

In the compounds represented by the formula (5-3), the compounds of the present invention wherein X is CH, $R^{2-2}$ is $CF_3$, and $R^1$, n, G, $R^{3-1}$, $R^{3-2}$, $R^{3-4}$ and $R^{3-5}$ are any of the combinations shown in [Table C].

In compounds represented by formula (5-4), (5-4)

the compounds of the present invention wherein X is N, $R^{2-2}$ is H, and $R^1$, n, G, $R^{3-1}$, $R^{3-2}$, $R^{3-4}$ and $R^{3-5}$ are any of the combinations shown in [Table C].

In the compounds represented by the formula (5-4), the compounds of the present invention wherein X is N, $R^{2-2}$ is $CF_3$, and $R^1$, n, G, $R^{3-1}$, $R^{3-2}$, $R^{3-4}$ and $R^{3-5}$ are any of the combinations shown in [Table C].

In the compounds represented by the formula (5-4), the compounds of the present invention wherein X is H, $R^{2-2}$ is CH, and $R^1$, n, G, $R^{3-1}$, $R^{3-2}$, $R^{3-4}$ and $R^{3-5}$ are any of the combinations shown in [Table C].

In the compounds represented by the formula (5-4), the compounds of the present invention wherein X is CH, $R^{2-2}$ is $CF_3$, and $R^1$, n, G, $R^{3-1}$, $R^{3-2}$, $R^{3-4}$ and $R^{3-5}$ are any of the combinations shown in [Table C].

In compounds represented by formula (5-5), (5-5)

the compounds of the present invention wherein X is N, $R^{2-2}$ is H, and $R^1$, n, G, $R^{3-1}$, $R^{3-2}$, $R^{3-4}$ and $R^{3-5}$ are any of the combinations shown in [Table C].

In the compounds represented by the formula (5-5), the compounds of the present invention wherein X is N, $R^{2-2}$ is $CF_3$, and $R^1$, n, G, $R^{3-1}$, $R^{3-2}$, $R^{3-4}$ and $R^{3-5}$ are any of the combinations shown in [Table C].

In the compounds represented by the formula (5-5), the compounds of the present invention wherein X is CH, $R^{2-2}$ is H, and $R^1$, n, G, $R^{3-1}$, $R^{3-2}$, $R^{3-4}$ and $R^{3-5}$ are any of the combinations shown in [Table C].

In the compounds represented by the formula (5-5), the compounds of the present invention wherein X is CH, $R^{2-2}$ is $CF_3$, and $R^1$, n, G, $R^{3-1}$, $R^{3-2}$, $R^{3-4}$ and $R^{3-5}$ are any of the combinations shown in [Table C].

In compounds represented by formula (5-6),

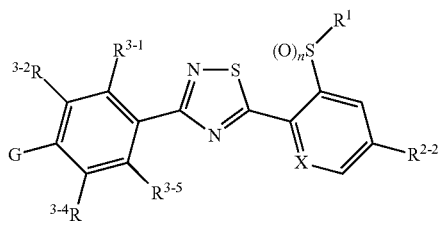

(5-6)

the compounds of the present invention wherein X is N, $R^{2-2}$ is H, and $R^1$, n, G, $R^{3-1}$, $R^{3-2}$, $R^{3-4}$ and $R^{3-5}$ are any of the combinations shown in [Table C].

In the compounds represented by the formula (5-6), the compounds of the present invention wherein X is N, $R^{2-2}$ is $CF_3$, and $R^1$, n, G, $R^{3-1}$, $R^{3-2}$, $R^{3-4}$ and $R^{3-5}$ are any of the combinations shown in [Table C].

In the compounds represented by the formula (5-6), the compounds of the present invention wherein X is CH, $R^{2-2}$ is H, and $R^1$, n, G, $R^{3-1}$, $R^{3-2}$, $R^{3-4}$ and $R^{3-5}$ are any of the combinations shown in [Table C].

In the compounds represented by the formula (5-6), the compounds of the present invention wherein X is CH, $R^{2-2}$ is $CF_3$, and $R^1$, n, G, $R^{3-1}$, $R^{3-2}$, $R^{3-4}$ and $R^{3-5}$ are any of the combinations shown in [Table C].

In compounds represented by formula (6-1),

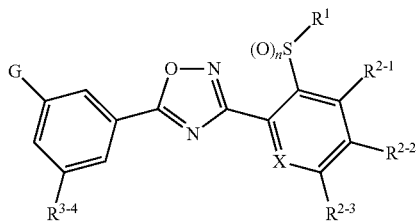

(6-1)

the compounds of the present invention wherein X is N, and $R^1$, n, $R^{2-1}$, $R^{2-2}$, $R^{2-3}$, G and $R^{3-4}$ are any of the combinations shown in [Table D].

TABLE D

| $R^1$ | n | $R^{2-1}$ | $R^{2-2}$ | $R^{2-3}$ | G | $R^{3-4}$ |
|---|---|---|---|---|---|---|
| $CH_2CH_3$ | 2 | $CH_3$ | H | H | $CF_3$ | $CF_3$ |
| $CH_2CH_3$ | 2 | $CH_3$ | H | H | $CF_3$ | H |
| $CH_2CH_3$ | 2 | $OCH_3$ | H | H | $CF_3$ | $CF_3$ |
| $CH_2CH_3$ | 2 | $OCH_3$ | H | H | $CF_3$ | H |
| $CH_2CH_3$ | 2 | Cl | H | H | $CF_3$ | $CF_3$ |
| $CH_2CH_3$ | 2 | Cl | H | H | $CF_3$ | H |
| $CH_2CH_3$ | 2 | H | $CH_3$ | H | $CF_3$ | $CF_3$ |
| $CH_2CH_3$ | 2 | H | $CH_3$ | H | $CF_3$ | H |
| $CH_2CH_3$ | 2 | H | $OCH_3$ | H | $CF_3$ | $CF_3$ |
| $CH_2CH_3$ | 2 | H | $OCH_3$ | H | $CF_3$ | H |
| $CH_2CH_3$ | 2 | H | Cl | H | $CF_3$ | $CF_3$ |
| $CH_2CH_3$ | 2 | H | Cl | H | $CF_3$ | H |
| $CH_2CH_3$ | 2 | H | H | $CH_3$ | $CF_3$ | $CF_3$ |
| $CH_2CH_3$ | 2 | H | H | $CH_3$ | $CF_3$ | H |
| $CH_2CH_3$ | 2 | H | H | $OCH_3$ | $CF_3$ | $CF_3$ |
| $CH_2CH_3$ | 2 | H | H | $OCH_3$ | $CF_3$ | H |
| $CH_2CH_3$ | 2 | H | H | Cl | $CF_3$ | $CF_3$ |
| $CH_2CH_3$ | 2 | H | H | Cl | $CF_3$ | H |

TABLE D-continued

| $R^1$ | n | $R^{2-1}$ | $R^{2-2}$ | $R^{2-3}$ | G | $R^{3-4}$ |
|---|---|---|---|---|---|---|
| $CH_2CH_3$ | 2 | H | $CF_2CF_3$ | H | $CF_3$ | H |
| $CH_2CH_3$ | 2 | H | $CF_2CF_2CF_3$ | H | $CF_3$ | H |

In compounds represented by formula (7-1),

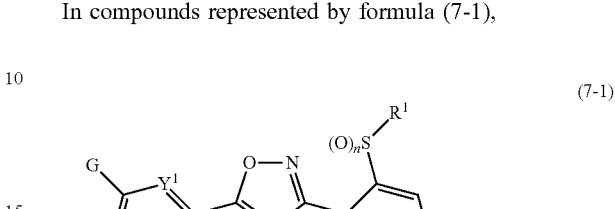

(7-1)

the compounds of the present invention wherein X is N, $R^{2-2}$ is H, and $R^1$, n, $Y^1$, $Y^3$, $Y^4$, $Y^5$ and G are any of the combinations shown in [Table E].

TABLE E

| $R^1$ | n | $Y^1$ | $Y^3$ | $Y^4$ | $Y^5$ | G |
|---|---|---|---|---|---|---|
| $CH_2CH_3$ | 2 | N | CH | CH | CH | $CF_3$ |
| $CH_2CH_3$ | 2 | CH | N | CH | CH | $CF_3$ |
| $CH_2CH_3$ | 2 | CH | CH | N | CH | $CF_3$ |
| $CH_2CH_3$ | 2 | CH | CH | CH | N | $CF_3$ |
| $CH_2CH_3$ | 2 | CH | CH | N | N | $CF_3$ |
| $CH_2CH_3$ | 2 | N | CH | CH | N | $CF_3$ |
| $CH_2CH_3$ | 2 | N | CH | N | CH | $CF_3$ |

In the compounds represented by the formula (7-1), the compounds of the present invention wherein X is N, $R^{2-2}$ is $CF_3$, and $R^1$, n, $Y^1$, $Y^3$, $Y^4$, $Y^5$ and G are any of the combinations shown in [Table E].

In the compounds represented by the formula (7-1), the compounds of the present invention wherein X is CH, $R^{2-2}$ is H, and $R^1$, n, $Y^1$, $Y^3$, $Y^4$, $Y^5$ and G are any of the combinations shown in [Table E].

In the compounds represented by the formula (7-1), the compounds of the present invention wherein X is CH, $R^{2-2}$ is $CF_3$, and $R^1$, n, $Y^1$, $Y^3$, $Y^4$, $Y^5$ and G are any of the combinations shown in [Table E].

In compounds represented by formula (7-2),

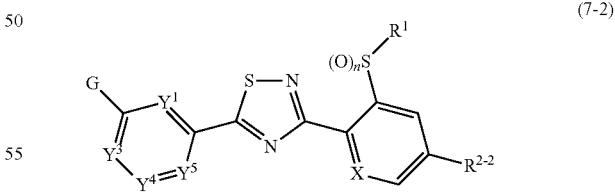

(7-2)

the compounds of the present invention wherein X is N, $R^{2-2}$ is H, and $R^1$, n, $Y^1$, $Y^3$, $Y^4$, $Y^5$ and G are any of the combinations shown in [Table E].

In the compounds represented by the formula (7-2), the compounds of the present invention wherein X is N, $R^{2-2}$ is $CF_3$, and $R^1$, n, $Y^1$, $Y^3$, $Y^4$, $Y^5$ and G axe any of the combinations shown in [Table E].

In the compounds represented by the formula (7-2), the compounds of the present invention wherein X is CH, $R^{2-2}$ is H, and $R^1$, n, $Y^1$, $Y^3$, $Y^4$, $Y^5$ and G are any of the combinations shown in [Table E].

In the compounds represented by the formula (7-2), the compounds of the present invention wherein X is CH, $R^{2-2}$ is $CF_3$, and $R^1$, n, $Y^1$, $Y^3$, $Y^4$, $Y^5$ and G are any of the combinations shown in [Table E].

In compounds represented by formula (7-3), (7-3)

the compounds of the present invention wherein X is N, $R^{2-2}$ is H, and $R^1$, n, $Y^1$, $Y^3$, $Y^4$, $Y^5$ and G are any of the combinations shown in [Table E].

In the compounds represented by the formula (7-3), the compounds of the present invention wherein X is N, $R^{2-2}$ is $CF_3$, and $R^1$, n, $Y^1$, $Y^3$, $Y^4$, $Y^5$ and G are any of the combinations shown in [Table E].

In the compounds represented by the formula (7-3), the compounds of the present invention wherein X is CH, $R^{2-2}$ is H, and $R^1$, n, $Y^1$, $Y^3$, $Y^4$, $Y^5$ and G axe any of the combinations shown in [Table E].

In the compounds represented by the formula (7-3), the compounds of the present invention wherein X is CH, $R^{2-2}$ is $CF_3$, and $R^1$, n, $Y^1$, $Y^3$, $Y^4$, $Y^5$ and G are any of the combinations shown in [Table E].

In compounds represented by formula (7-4), (7-4)

the compounds of the present invention wherein X is N, $R^{2-2}$ is H, and $R^1$, n, $Y^1$, $Y^3$, $Y^4$, $Y^5$ and G are any of the combinations shown in [Table E].

In the compounds represented by the formula (7-4), the compounds of the present invention wherein X is N, $R^{2-2}$ is $CF_3$, and $R^1$, n, $Y^1$, $Y^3$, $Y^4$, $Y^5$ and G are any of the combinations shown in [Table E].

In the compounds represented by the formula (7-4), the compounds of the present invention wherein X is CH, $R^{2-2}$ is H, and $R^1$, n, $Y^1$, $Y^3$, $Y^4$, $Y^5$ and G are any of the combinations shown in [Table E].

In the compounds represented by the formula (7-4), the compounds of the present invention wherein X is CH, $R^{2-2}$ is $CF_3$, and $R^1$, n, $Y^1$, $Y^3$, $Y^4$, $Y^5$ and G axe any of the combinations shown in [Table E].

In compounds represented by formula (7-5), (7-5)

the compounds of the present invention wherein X is N, $R^{2-2}$ is H, and $R^1$, n, $Y^1$, $Y^3$, $Y^4$, $Y^5$ and G are any of the combinations shown in [Table E].

In the compounds represented by the formula (7-5), the compounds of the present invention wherein X is N, $R^{2-2}$ is $CF_3$, and $R^1$, n, $Y^1$, $Y^3$, $Y^4$, $Y^5$ and G are any of the combinations shown in [Table E].

In the compounds represented by the formula (7-5), the compounds of the present invention wherein X is CH, $R^{2-2}$ is H, and $R^1$, n, $Y^1$, $Y^3$, $Y^4$, $Y^5$ and G are any of the combinations shown in [Table E].

In the compounds represented by the formula (7-5), the compounds of the present invention wherein X is CH, $R^{2-2}$ is $CF_3$, and $R^1$, n, $Y^1$, $Y^3$, $Y^4$, $Y^5$ and G are any of the combinations shown in [Table E].

In compounds represented by formula (7-6), (7-6)

the compounds of the present invention wherein X is N, $R^{2-2}$ is H, and $R^1$, n, $Y^1$, $Y^3$, $Y^4$, $Y^5$ and G are any of the combinations shown in [Table E].

In the compounds represented by the formula (7-6), the compounds of the present invention wherein X is N, $R^{2-2}$ is $CF_3$, and $R^1$, n, $Y^1$, $Y^3$, $Y^4$, $Y^5$ and G are any of the combinations shown in [Table E].

In the compounds represented by the formula (7-6), the compounds of the present invention wherein X is CH, $R^{2-2}$ is H, and $R^1$, n, $Y^1$, $Y^3$, $Y^4$, $Y^5$ and G are any of the combinations shown in [Table E].

In the compounds represented by the formula (7-6), the compounds of the present invention wherein X is CH, $R^{2-2}$ is $CF_3$, and $R^1$, n, $Y^1$, $Y^3$, $Y^4$, $Y^5$ and G are any of the combinations shown in [Table E].

In compounds represented by formula (8-1), (8-1)

the compounds of the present invention wherein X is N, $R^{2-2}$ is H, and $R^1$, n, $Y^1$, $Y^2$, $Y^4$, $Y^5$ and G are any of the combinations shown in [Table F].

TABLE F

| $R^1$ | n | $Y^1$ | $Y^2$ | $Y^4$ | $Y^5$ | G |
|---|---|---|---|---|---|---|
| $CH_2CH_3$ | 2 | N | CH | CH | CH | $CF_3$ |
| $CH_2CH_3$ | 2 | CH | N | CH | CH | $CF_3$ |
| $CH_2CH_3$ | 2 | N | N | CH | CH | $CF_3$ |
| $CH_2CH_3$ | 2 | N | CH | N | CH | $CF_3$ |
| $CH_2CH_3$ | 2 | CH | N | N | CH | $CF_3$ |
| $CH_2CH_3$ | 2 | N | CH | CH | N | $CF_3$ |

In the compounds represented by the formula (8-1), the compounds of the present invention wherein X is N, $R^{2-2}$ is $CF_3$, and $R^1$, n, $Y^1$, $Y^2$, $Y^4$, $Y^5$ and G are any of the combinations shown in [Table F].

In the compounds represented by the formula (8-1), the compounds of the present invention wherein X is CH, $R^{2-2}$ is H, and $R^1$, n, $Y^1$, $Y^2$, $Y^4$, $Y^5$ and G are any of the combinations shown in [Table F].

In the compounds represented by the formula (8-1), the compounds of the present invention wherein X is CH, $R^{2-2}$ is $CF_3$, and $R^1$, n, $Y^1$, $Y^2$, $Y^4$, $Y^5$ and G are any of the combinations shown in [Table F].

In compounds represented by formula (8-2), (8-2)

the compounds of the present invention wherein X is N, $R^{2-2}$ is H, and $R^1$, n, $Y^1$, $Y^2$, $Y^4$, $Y^5$ and G are any of the combinations shown in [Table F].

In the compounds represented by the formula (8-2), the compounds of the present invention wherein X is N, $R^{2-2}$ is $CF_3$, and $R^1$, n, $Y^1$, $Y^2$, $Y^4$, $Y^5$ and G are any of the combinations shown in [Table F].

In the compounds represented by the formula (8-2), the compounds of the present invention wherein X is CH, $R^{2-2}$ is H, and $R^1$, n, $Y^1$, $Y^2$, $Y^4$, $Y^5$ and G are any of the combinations shown in [Table F].

In the compounds represented by the formula (8-2), the compounds of the present invention wherein X is CH, $R^{2-2}$ is $CF_3$, and $R^1$, n, $Y^1$, $Y^2$, $Y^4$, $Y^5$ and G are any of the combinations shown in [Table F].

In compounds represented by formula (8-3), (8-3)

the compounds of the present invention wherein X is N, $R^{2-2}$ is H, and $R^1$, n, $Y^1$, $Y^2$, $Y^4$, $Y^5$ and G are any of the combinations shown in [Table F].

In the compounds represented by the formula (8-3), the compounds of the present invention wherein X is N, $R^{2-2}$ is $CF_3$, and $R^1$, n, $Y^1$, $Y^2$, $Y^4$, $Y^5$ and G are any of the combinations shown in [Table F].

In the compounds represented by the formula (8-3), the compounds of the present invention wherein X is CH, $R^{2-2}$ is H, and $R^1$, n, $Y^1$, $Y^2$, $Y^4$, $Y^5$ and G are any of the combinations shown in [Table F].

In the compounds represented by the formula (8-3), the compounds of the present invention wherein X is CH, $R^{2-2}$ is $CF_3$, and $R^1$, n, $Y^1$, $Y^2$, $Y^4$, $Y^5$ and G are any of the combinations shown in [Table F].

In compounds represented by formula (8-4), (8-4)

the compounds of the present invention wherein X is N, $R^{2-2}$ is H, and $R^1$, n, $Y^1$, $Y^2$, $Y^4$, $Y^5$ and G are any of the combinations shown in [Table F].

In the compounds represented by the formula (8-4), the compounds of the present invention wherein X is N, $R^{2-2}$ is $CF_3$, and $R^1$, n, $Y^1$, $Y^2$, $Y^4$, $Y^5$ and G are any of the combinations shown in [Table F].

In the compounds represented by the formula (8-4), the compounds of the present invention wherein X is CH, $R^{2-2}$ is H, and $R^1$, n, $Y^1$, $Y^2$, $Y^4$, $Y^5$ and G are any of the combinations shown in [Table F].

In the compounds represented by the formula (8-4), the compounds of the present invention wherein X is CH, $R^{2-2}$ is $CF_3$, and $R^1$, n, $Y^1$, $Y^2$, $Y^4$, $Y^5$ and G are any of the combinations shown in [Table F].

In compounds represented by formula (8-5), (8-5)

the compounds of the present invention wherein X is N, $R^{2-2}$ is H, and $R^1$, n, $Y^1$, $Y^2$, $Y^4$, $Y^5$ and G are any of the combinations shown in [Table F].

In the compounds represented by the formula (8-5), the compounds of the present invention wherein X is N, $R^{2-2}$ is $CF_3$, and $R^1$, n, $Y^1$, $Y^2$, $Y^4$, $Y^5$ and G are any of the combinations shown in [Table F].

In the compounds represented by the formula (8-5), the compounds of the present invention wherein X is CH, $R^{2-2}$ is H, and $R^1$, n, $Y^1$, $Y^2$, $Y^4$, $Y^5$ and G are any of the combinations shown in [Table F].

In the compounds represented by the formula (8-5), the compounds of the present invention wherein X is CH, $R^{2-2}$ is $CF_3$, and $R^1$, n, $Y^1$, $Y^2$, $Y^4$, $Y^5$ and G are any of the combinations shown in [Table F].

In compounds represented by formula (8-6),

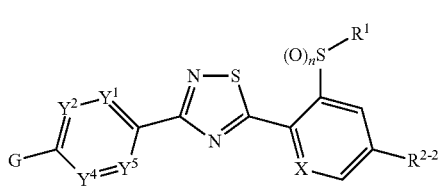
(8-6)

the compounds of the present invention wherein X is N, $R^{2-2}$ is H, and $R^1$, n, $Y^1$, $Y^2$, $Y^4$, $Y^5$ and G are any of the combinations shown in [Table F].

In the compounds represented by the formula (8-6), the compounds of the present invention wherein X is N, $R^{2-2}$ is $CF_3$, and $R^1$, n, $Y^1$, $Y^2$, $Y^4$, $Y^5$ and G are any of the combinations shown in [Table F].

In the compounds represented by the formula (8-6), the compounds of the present invention wherein X is CH, $R^{2-2}$ is H, and $R^1$, n, $Y^1$, $Y^2$, $Y^4$, $Y^5$ and G are any of the combinations shown in [Table F].

In the compounds represented by the formula (8-6), the compounds of the present invention wherein X is CH, $R^{2-2}$ is $CF_3$, and $R^1$, n, $Y^1$, $Y^2$, $Y^4$, $Y^5$ and G are any of the combinations shown in [Table F].

In compounds represented by formula (9-1),

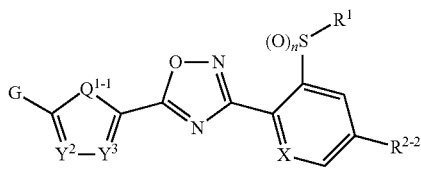
(9-1)

the compounds of the present invention wherein X is N, $R^{2-2}$ is H, and $R^1$, n, $Q^{1-1}$, $Y^2$, $Y^3$ and G are any of the combinations shown in [Table G].

TABLE G

| $R^1$ | n | $Q^{1-1}$ | $Y^2$ | $Y^3$ | G |
|---|---|---|---|---|---|
| $CH_2CH_3$ | 2 | O | CH | CH | $CF_3$ |
| $CH_2CH_3$ | 2 | S | CH | CH | $CF_3$ |
| $CH_2CH_3$ | 2 | $NCH_3$ | CH | CH | $CF_3$ |

In the compounds represented by the formula (9-1), the compounds of the present invention wherein X is N, $R^{2-2}$ is $CF_3$, and $R^1$, n, $Q^{1-1}$, $Y^2$, $Y^3$ and G are any of the combinations shown in [Table G].

In the compounds represented by the formula (9-1), the compounds of the present invention wherein X is CH, $R^{2-2}$ is H, and $R^1$, n, $Q^{1-1}$, $Y^2$, $Y^3$ and G are any of the combinations shown in [Table G].

In the compounds represented by the formula (9-1), the compounds of the present invention wherein X is CH, $R^{2-2}$ is $CF_3$, and $R^1$, n, $Q^{1-1}$, $Y^2$, $Y^3$ and G are any of the combinations shown in [Table G].

In compounds represented by formula (9-2),

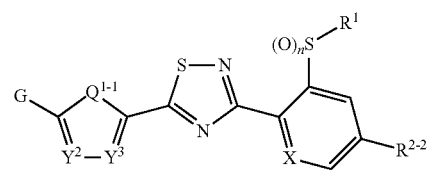
(9-2)

the compounds of the present invention wherein X is N, $R^{2-2}$ is H, and $R^1$, n, $Q^{1-1}$, $Y^2$, $Y^3$ and G are any of the combinations shown in [Table G].

In the compounds represented by the formula (9-2), the compounds of the present invention wherein X is N, $R^{2-2}$ is $CF_3$, and $R^1$, n, $Q^{1-1}$, $Y^2$, $Y^3$ and G are any of the combinations shown in [Table G].

In the compounds represented by the formula (9-2), the compounds of the present invention wherein X is CH, $R^{2-2}$ is H, and $R^1$, n, $Q^{1-1}$, $Y^2$, $Y^3$ and G are any of the combinations shown in [Table G].

In the compounds represented by the formula (9-2), the compounds of the present invention wherein X is CH, $R^{2-2}$ is $CF_3$, and $R^1$, n, $Q^{1-1}$, $Y^2$, $Y^3$ and G are any of the combinations shown in [Table G].

In compounds represented by formula (9-3),

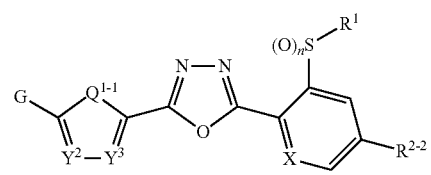
(9-3)

the compounds of the present invention wherein X is N, $R^{2-2}$ is H, and $R^1$, n, $Q^{1-1}$, $Y^2$, $Y^3$ and G are any of the combinations shown in [Table G].

In the compounds represented by the formula (9-3), the compounds of the present invention wherein X is N, $R^{2-2}$ is $CF_3$, and $R^1$, n, $Q^{1-1}$, $Y^2$, $Y^3$ and G are any of the combinations shown in [Table G].

In the compounds represented by the formula (9-3), the compounds of the present invention wherein X is CH, $R^{2-2}$ is H, and $R^1$, n, $Q^{1-1}$, $Y^2$, $Y^3$ and G are any of the combinations shown in [Table G].

In the compounds represented by the formula (9-3), the compounds of the present invention wherein X is CH, $R^{2-2}$ is $CF_3$, and $R^1$, n, $Q^{1-1}$, $Y^2$, $Y^3$ and G are any of the combinations shown in [Table G].

In compounds represented by formula (9-4),

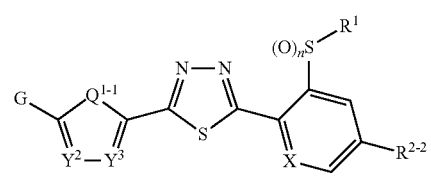
(9-4)

the compounds of the present invention wherein X is N, $R^{2-2}$ is H, and $R^1$, n, $Q^{1-1}$, $Y^2$, $Y^3$ and G are any of the combinations shown in [Table G].

In the compounds represented by the formula (9-4), the compounds of the present invention wherein X is N, $R^{2-2}$ is $CF_3$, and $R^1$, n, $Q^{1-1}$, $Y^2$, $Y^3$ and G are any of the combinations shown in [Table G].

In the compounds represented by the formula (9-4), the compounds of the present invention wherein X is CH, $R^{2-2}$ is H, and $R^1$, n, $Q^{1-1}$, $Y^2$, $Y^3$ and G are any of the combinations shown in [Table G].

In the compounds represented by the formula (9-4), the compounds of the present invention wherein X is CH, $R^{2-2}$ is $CF_3$, and $R^1$, n, $Q^{1-1}$, $Y^2$, $Y^3$ and G are any of the combinations shown in [Table G].

In compounds represented by formula (9-5),

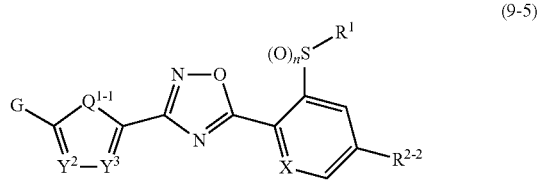

(9-5)

the compounds of the present invention wherein X is N, $R^{2-2}$ is H, and $R^1$, n, $Q^{1-1}$, $Y^2$, $Y^3$ and G are any of the combinations shown in [Table G].

In the compounds represented by the formula (9-5), the compounds of the present invention wherein X is N, $R^{2-2}$ is $CF_3$, and $R^1$, n, $Q^{1-1}$, $Y^2$, $Y^3$ and G are any of the combinations shown in [Table G].

In the compounds represented by the formula (9-5), the compounds of the present invention wherein X is CH, $R^{2-2}$ is H, and $R^1$, n, $Q^{1-1}$, $Y^2$, $Y^3$ and G are any of the combinations shown in [Table G].

In the compounds represented by the formula (9-5), the compounds of the present invention wherein X is CH, $R^{2-2}$ is $CF_3$, and $R^1$, n, $Q^{1-1}$, $Y^2$, $Y^3$ and G are any of the combinations shown in [Table G].

In compounds represented by formula (9-6),

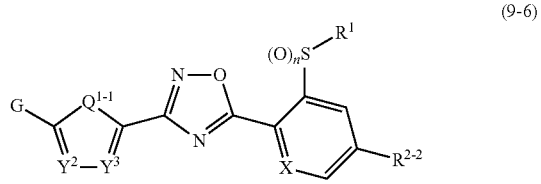

(9-6)

the compounds of the present invention wherein X is N, $R^{2-2}$ is H, and $R^1$, n, $Q^{1-1}$, $Y^2$, $Y^3$ and G are any of the combinations shown in [Table G].

In the compounds represented by the formula (9-6), the compounds of the present invention wherein X is N, $R^{2-2}$ is $CF_3$, and $R^1$, n, $Q^{1-1}$, $Y^2$, $Y^3$ and G are any of the combinations shown in [Table G].

In the compounds represented by the formula (9-6), the compounds of the present invention wherein X is CH, $R^{2-2}$ is H, and $R^1$, n, $Q^{1-1}$, $Y^2$, $Y^3$ and G are any of the combinations shown in [Table G].

In the compounds represented by the formula (9-6), the compounds of the present invention wherein X is CH, $R^{2-2}$ is $CF_3$, and $R^1$, n, $Q^{1-1}$, $Y^2$, $Y^3$ and G are any of the combinations shown in [Table G].

In compounds represented by formula (10-1),

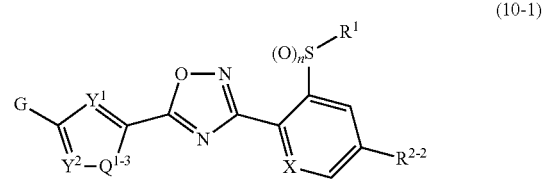

(10-1)

the compounds of the present invention wherein X is N, $R^{2-2}$ is H, and $R^1$, n, $Q^{1-3}$, $Y^1$, $Y^2$ and G axe any of the combinations shown in [Table H].

TABLE H

| $R^1$ | n | $Q^{1-3}$ | $Y^1$ | $Y^2$ | G |
|---|---|---|---|---|---|
| $CH_2CH_3$ | 2 | S | N | H | $CF_3$ |
| $CH_2CH_3$ | 2 | O | N | H | $CF_3$ |
| $CH_2CH_3$ | 2 | $NCH_3$ | N | H | $CF_3$ |
| $CH_2CH_3$ | 2 | $NCH_3$ | CH | N | $CF_3$ |

In the compounds represented by the formula (10-1), the compounds of the present invention wherein X is N, $R^{2-2}$ is $CF_3$, and $R^1$, n, $Q^{1-3}$, $Y^1$, $Y^2$ and G are any of the combinations shown in [Table H].

In the compounds represented by the formula (10-1), the compounds of the present invention wherein X is CH, $R^{2-2}$ is H, and $R^1$, n, $Q^{1-3}$, $Y^1$, $Y^2$ and G are any of the combinations shown in [Table H].

In the compounds represented by the formula (10-1), the compounds of the present invention wherein X is CH, $R^{2-2}$ is $CF_3$, and $R^1$, n, $Q^{1-3}$, $Y^1$, $Y^2$ and G are any of the combinations shown in [Table H].

In compounds represented by formula (10-2),

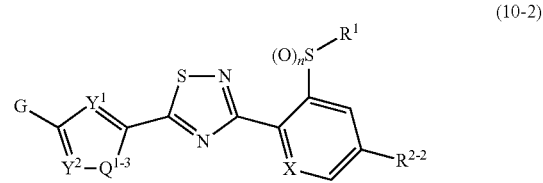

(10-2)

the compounds of the present invention wherein X is N, $R^{2-2}$ is H, and $R^1$, n, $Q^{1-3}$, $Y^1$, $Y^2$ and G are any of the combinations shown in [Table H].

In the compounds represented by the formula (10-2), the compounds of the present invention wherein X is N, $R^{2-2}$ is $CF_3$, and $R^1$, n, $Q^{1-3}$, $Y^1$, $Y^2$ and G are any of the combinations shown in [Table H].

In the compounds represented by the formula (10-2), the compounds of the present invention wherein X is CH, $R^{2-2}$ is H, and $R^1$, n, $Q^{1-3}$, $Y^1$, $Y^2$ and G are any of the combinations shown in [Table H].

In the compounds represented by the formula (10-2), the compounds of the present invention wherein X is CH, $R^{2-2}$ is $CF_3$, and $R^1$, n, $Q^{1-3}$, $Y^1$, $Y^2$ and G are any of the combinations shown in [Table H].

In compounds represented by formula (10-3), (10-3)

the compounds of the present invention wherein X is N, $R^{2-2}$ is H, and $R^1$, n, $Q^{1-3}$, $Y^1$, $Y^2$ and G are any of the combinations shown in [Table H].

In the compounds represented by the formula (10-3), the compounds of the present invention wherein X is N, $R^{2-2}$ is $CF_3$, and $R^1$, n, $Q^{1-3}$, $Y^1$, $Y^2$ and G are any of the combinations shown in [Table H].

In the compounds represented by the formula (10-3), the compounds of the present invention wherein X is CH, $R^{2-2}$ is H, and $R^1$, n, $Q^{1-3}$, $Y^1$, $Y^2$ and G are any of the combinations shown in [Table H].

In the compounds represented by the formula (10-3), the compounds of the present invention wherein X is CH, $R^{2-2}$ is $CF_3$, and $R^1$, n, $Q^{1-3}$, $Y^1$, $Y^2$ and G are any of the combinations shown in [Table H].

In compounds represented by formula (10-4), (10-4)

the compounds of the present invention wherein X is N, $R^{2-2}$ is H, and $R^1$, n, $Q^{1-3}$, $Y^1$, $Y^2$ and G are any of the combinations shown in [Table H].

In the compounds represented by the formula (10-4), the compounds of the present invention wherein X is N, $R^{2-2}$ is $CF_3$, and $R^1$, n, $Q^{1-3}$, $Y^1$, $Y^2$ and G are any of the combinations shown in [Table H].

In the compounds represented by the formula (10-4), the compounds of the present invention wherein X is CH, $R^{2-2}$ is H, and $R^1$, n, $Q^{1-3}$, $Y^1$, $Y^2$ and G are any of the combinations shown in [Table H].

In the compounds represented by the formula (10-4), the compounds of the present invention wherein X is CH, $R^{2-2}$ is $CF_3$, and $R^1$, n, $Q^{1-3}$, $Y^1$, $Y^2$ and G are any of the combinations shown in [Table H].

In compounds represented by formula (10-5), (10-5)

the compounds of the present invention wherein X is N, $R^{2-2}$ is H, and $R^1$, n, $Q^{1-3}$, $Y^1$, $Y^2$ and G are any of the combinations shown in [Table H].

In the compounds represented by the formula (10-5), the compounds of the present invention wherein X is N, $R^{2-2}$ is $CF_3$, and $R^1$, n, $Q^{1-3}$, $Y^1$, $Y^2$ and G are any of the combinations shown in [Table H].

In the compounds represented by the formula (10-5), the compounds of the present invention wherein X is CH, $R^{2-2}$ is H, and $R^1$, n, $Q^{1-3}$, $Y^1$, $Y^2$ and G are any of the combinations shown in [Table H].

In the compounds represented by the formula (10-5), the compounds of the present invention wherein X is CH, $R^{2-2}$ is $CF_3$, and $R^1$, n, $Q^{1-3}$, $Y^1$, $Y^2$ and G are any of the combinations shown in [Table H].

In compounds represented by formula (10-6), (10-6)

the compounds of the present invention wherein X is N, $R^{2-2}$ is H, and $R^1$, n, $Q^{1-3}$, $Y^1$, $Y^2$ and G are any of the combinations shown in [Table H].

In the compounds represented by the formula (10-6), the compounds of the present invention wherein X is N, $R^{2-2}$ is $CF_3$, and $R^1$, n, $Q^{1-3}$, $Y^1$, $Y^2$ and G are any of the combinations shown in [Table H].

In the compounds represented by the formula (10-6), the compounds of the present invention wherein X is CH, $R^{2-2}$ is H, and $R^1$, n, $Q^{1-3}$, $Y^1$, $Y^2$ and G are any of the combinations shown in [Table H].

In the compounds represented by the formula (10-6), the compounds of the present invention wherein X is CH, $R^{2-2}$ is $CF_3$, and $R^1$, n, $Q^{1-3}$, $Y^1$, $Y^2$ and G are any of the combinations shown in [Table H].

In compounds represented by formula (11-1), (11-1)

the compounds of the present invention wherein X is N, $R^{2-2}$ is H, and $R^1$, n, $Y^1$, $Y^2$, $Y^3$ and G are any of the combinations shown in [Table I].

TABLE I

| $R^1$ | n | $Y^1$ | $Y^2$ | $Y^3$ | G |
|---|---|---|---|---|---|
| $CH_2CH_3$ | 2 | CH | CH | CH | $CF_3$ |
| $CH_2CH_3$ | 2 | N | CH | CH | $CF_3$ |
| $CH_2CH_3$ | 2 | N | CH | CH | $CF_3CF_2$ |
| $CH_2CH_3$ | 2 | N | CCl | CH | $CF_3$ |
| $CH_2CH_3$ | 2 | N | CBr | CH | $CF_3$ |
| $CH_2CH_3$ | 2 | CH | N | CH | $CF_3$ |
| $CH_2CH_3$ | 2 | N | N | CH | $CF_3$ |
| $CH_2CH_3$ | 2 | N | CH | N | $CF_3$ |
| $CH_2CH_3$ | 2 | CH | N | N | $CF_3$ |

In the compounds represented by the formula (11-1), the compounds of the present invention wherein X is N, $R^{2-2}$ is $CF_3$, and $R^1$, n, $Y^1$, $Y^2$, $Y^3$ and G are any of the combinations shown in [Table I].

In the compounds represented by the formula (11-1), the compounds of the present invention wherein X is CH, $R^{2-2}$ is H, and $R^1$, n, $Y^1$, $Y^2$, $Y^3$ and G are any of the combinations shown in [Table I].

In the compounds represented by the formula (11-1), the compounds of the present invention wherein X is CH, $R^{2-2}$ is $CF_3$, and $R^1$, n, $Y^1$, $Y^2$, $Y^3$ and G are any of the combinations shown in [Table I].

In compounds represented by formula (11-2), (11-2)

the compounds of the present invention wherein X is N, $R^{2-2}$ is H, and $R^1$, n, $Y^1$, $Y^2$, $Y^3$ and G are any of the combinations shown in [Table I].

In the compounds represented by the formula (11-2), the compounds of the present invention wherein X is N, $R^{2-2}$ is $CF_3$, and $R^1$, n, $Y^1$, $Y^2$, $Y^3$ and G are any of the combinations shown in [Table I].

In the compounds represented by the formula (11-2), the compounds of the present invention wherein X is CH, $R^{2-2}$ is H, and $R^1$, n, $Y^1$, $Y^2$, $Y^3$ and G are any of the combinations shown in [Table I].

In the compounds represented by the formula (11-2), the compounds of the present invention wherein X is CH, $R^{2-2}$ is $CF_3$, and $R^1$, n, $Y^1$, $Y^2$, $Y^3$ and G are any of the combinations shown in [Table I], In compounds represented by formula (11-3), (11-3)

the compounds of the present invention wherein X is N, $R^{2-2}$ is H, and $R^1$, n, $Y^1$, $Y^2$, $Y^3$ and G are any of the combinations shown in [Table I].

In the compounds represented by the formula (11-3), the compounds of the present invention wherein X is N, $R^{2-2}$ is $CF_3$, and $R^1$, n, $Y^1$, $Y^2$, $Y^3$ and G are any of the combinations shown in [Table I].

In the compounds represented by the formula (11-3), the compounds of the present invention wherein X is CH, $R^{2-2}$ is H, and $R^1$, n, $Y^1$, $Y^2$, $Y^3$ and G are any of the combinations shown in [Table I].

In the compounds represented by the formula (11-3), the compounds of the present invention wherein X is CH, $R^{2-2}$ is $CF_3$, and $R^1$, n, $Y^1$, $Y^2$, $Y^3$ and G are any of the combinations shown in [Table I].

In compounds represented by formula (11-4), (11-4)

the compounds of the present invention wherein X is N, $R^{2-2}$ is H, and $R^1$, n, $Y^1$, $Y^2$, $Y^3$ and G are any of the combinations shown in [Table I].

In the compounds represented by the formula (11-4), the compounds of the present invention wherein X is N, $R^{2-2}$ is $CF_3$, and $R^1$, n, $Y^1$, $Y^2$, $Y^3$ and G are any of the combinations shown in [Table I].

In the compounds represented by the formula (11-4), the compounds of the present invention wherein X is CH, $R^{2-2}$ is H, and $R^1$, n, $Y^1$, $Y^2$, $Y^3$ and G are any of the combinations shown in [Table I].

In the compounds represented by the formula (11-4), the compounds of the present invention wherein X is CH, $R^{2-2}$ is $CF_3$, and $R^1$, n, $Y^1$, $Y^2$, $Y^3$ and G are any of the combinations shown in [Table I].

In compounds represented by formula (11-5), (11-5)

the compounds of the present invention wherein X is N, $R^{2-2}$ is H, and $R^1$, n, $Y^1$, $Y^2$, $Y^3$ and G are any of the combinations shown in [Table I], In the compounds represented by the formula (11-5), the compounds of the present invention wherein X is N, $R^{2-2}$ is $CF_3$, and $R^1$, n, $Y^1$, $Y^2$, $Y^3$ and G are any of the combinations shown in [Table I].

In the compounds represented by the formula (11-5), the compounds of the present invention wherein X is CH, $R^{2-2}$ is H, and $R^1$, n, $Y^1$, $Y^2$, $Y^3$ and G are any of the combinations shown in [Table I].

In the compounds represented by the formula (11-5), the compounds of the present invention wherein X is CH, $R^{2-2}$ is $CF_3$, and $R^1$, n, $Y^1$, $Y^2$, $Y^3$ and G are any of the combinations shown in [Table I].

In compounds represented by formula (11-6), (11-6)

the compounds of the present invention wherein X is N, $R^{2-2}$ is H, and $R^1$, n, $Y^1$, $Y^2$, $Y^3$ and G are any of the combinations shown in [Table I].

In the compounds represented by the formula (11-6), the compounds of the present invention wherein X is N, $R^{2-2}$ is $CF_3$, and $R^1$, n, $Y^1$, $Y^2$, $Y^3$ and G are any of the combinations shown in [Table I].

In the compounds represented by the formula (11-6), the compounds of the present invention wherein X is CH, $R^{2-2}$ is H, and $R^1$, n, $Y^1$, $Y^2$, $Y^3$ and G are any of the combinations shown in [Table I].

In the compounds represented by the formula (11-6), the compounds of the present invention wherein X is CH, $R^{2-2}$ is $CF_3$, and $R^1$, n, $Y^1$, $Y^2$, $Y^3$ and G are any of the combinations shown in [Table I].

Examples of the arthropod pest on which the control agent of the present invention has an effect include Insecta, Arachnida, Chilopoda, Diplopoda, Isopoda, Gastropoda, and the like. Examples of the pest Insecta include Hemiptera pests, Lepidoptera pests, Thysanoptera pests, Diptera pests, Coleoptera pests, Orthoptera pests, Siphonaptera pests, Anoplura pests, Mallophaga pests, Hymenoptera pests, Blattodea pests, Isoptera ests, and the like. Examples of Arachnida include Araneae pests, Acarina pests, and the like. Specifically, examples of the arthropod pests include those shown below.

Hemiptera pests: Delphacidae such as *Laodelphax striatella*, *Nilaparvata lugens*, and *Sogatella furcifera*, Deitocephalidae such as *Nephotettix cincticeps*, *Nephotettix virescens*, and *Emipoasca onukii*, Aphididae such as *Aphis gossypii*, *Myzus persicae*, *Brevicoryne brassicae*, *Aphis spiraecola*, *Macrosiphum*, *euphorbiae*, *Aulacorthumi solani*, *Rhopalosiphum padi*, *Toxoptera citricidus*, and *Hyalopterus pruni*, Pentatomidae such as *Nezara antennata*, *Riptortus clavetus*, *Leptocorisa chinensis*, *Eysazcoris parvus*, and *Halyomorpha mista*, Aleyrodidae such as *Trialeurodes vaporariorum*, *Bemisia tabaci*, *Dialeurodes citri*, and *Aleurocanthus spiniferus*, Coccidae such as *Aonidieila aurantii*, *Comstockaspis perniciosa*, *Unaspis citri*, *Ceroplastes rubens*, *Icerya purchasi*, *Planococcus kraunhiae*, *Pseudococcus longispinis*, and *Pseudaulacaspis pentagona*, Tingidae, Cimicoidea such as *Cimex lectularius*, and Psyliidae.

Lepidoptera pests: Pyralidae such as *Chilo suppressalis*, *Tryporyza inlcertulas*, *Cnaphalocrocis medinalis*, *Notarcha derogata*, *Plodia interpunctelia*, *Oztrinia furnacalis*, *Hellula undalis*, and *Pediasia teterrellus*, Noctuidae such as *Spodoptera litura*, *Spodoptera exigua*, *Pseudaletia separata*, *Mamestra brassicae*, *Agrotis ipsilon*, *Plusia nigrisigna*, *Trichoplusia* spp., *Heliothis* spp., and *Helicoverpa* spp., Pieridae such as *Pieris rapae*, *Adoxophyes* spp., Tortricidae such as *Grapholita molesta*, *Leguminivora glycinivorella*, *Matsumuraeses azukivora*, *Adoxophyes orana fasciata*, *Adoxophyes honmai.*, *Homona magnanima*, *Archips fuscocupreanus*, and *Cydia pomonella*, Graciliariidae such as *Caloptilia theivora* and *Phyllonorycter ringoneella*, Carposinidae such as *Carposina niponensis*, Lyonetiidae such as *Lyonetia* spp., Lymantriidae such as *Lymantria* spp. and *Euproctis* spp., Yponomeutidae such as *Plutella xylostella*, Gelechildae such as *Pectinophora gossypiella* and *Phthorimaea operculella*, Arctiidae such as *Hyphantria cunea*, and Tineidae such as *Tinea translucens* and *Tineola bisselliella*.

Thysanoptera pests: Thripidae such as *Frankliniella occidentalis*, *Thrips parmi*, *Scirtothrips dorsalis*, *Thrips tabaci*, and *Frankliniella intonsa*.

Diptera pests: Culex such as *Culex pipiens pallens*, *Culex tritaeniorhynchus*, and *Culex quinquefasciatus*, *Aedes* spp. such as *Aedes aegypti* and *Aedes albopictus*, *Anopheles* spp. such as *Anopheles sinensis*, Chironomidae, Muscidae such as *Musca domestica* and *Muscina stabulans*, Calliphoridae, Sarcophagidae, Fanniidae, Anthomyiidae such as *Delia platura* and *Delia antiqua*, Agromyzidae such as *Agromyza oryzae*, *Hydrellia griseola*, *Liriomyza sativae*, *Liriomiyza trifolii*, and *Chromatornyia horticola*, Chioropidae such as *Chlorops oryzae*, Tephritidae such as *Dacus cucurbitae* and *Ceratitis capitata*, Doesophilidae, Phoridae such as *Megaselia spiracularis*, Psychodidae such as *Clogmia albipunctata*, Sciaridae, Simuliidae, Tabanidae such as *Tabanus trigonus*, *Stomoxys*, and Stomnoxyidae.

Coleoptera pests: Corn rootworm such as *Diabrotica virgifera virgifera* and *Diabrotica undecimpunctata howardi*, Scarabaeidae such as *Anomala cuprea Anomala rufocuprea*, and *Popillia japonica*, Curculionidae such as *Sitophilus zeamais*, *Lissorhoptrus oryzophilus*, and *Callosobruchuys chienensis*, *Echinocnemus squameus*, *Anthonoznus grandis*, and *Sphenophorus venatus*, Tenebrionidae such as *Tenebrio molitor* and *Tribolium castaneum*, Chrysomelidae such as *Oulema oryzae*, *Aulacophora femnoralis*, *Phyllotreta striolata*, and *Leptinotarsa decemlineata*, Dermestidae such as *Anthrenus verbasci* and *Dermestes maculates*, Anobiidae such as *Lasiodexma serricorne*, Epilachna such as *Epilachna vigintioctopunctata*, Scolytidae such as *Lyctus brunneus* and *Tonicus piniperda*, Boetrychidae, Ptinidaie, Cerambycidae such as *Anoplophora malasiaca*, Elateridae such as *Agriotes* spp, and *Paederus fuscipes*.

Orthoptera pests: *Locusta migratoria*, *Gryllotalpa africana*, *Oxya yexoensis*, *Oxya japonica*, and Grylloidea.

Siphonaptera pests: *Ctenocephaiides felis*, *Ctenocephalides canis*, *Pulex irritans*, *Xenopsylla cheopis*, and the like.

Anoplura pests: *Pediculus humanus corporis*, *Pediculus humanus humanus*, *Phthirus pubis*, *Haemiatopinus eurysternius*, *Dalmalinia ovis*, *Haemiatopinus suis*, *Liniognathus setosus*, and the like.

Mallophaga pests: *Dalmalinia ovis*, *Dalmalinia bovis*, *Menopon gallinae*, *Trichodectes canis*, *Felicola subrostrata*, and the like Hymenoptera pests: Formicidae such as *Monomorium pharaosis*, *Formica fusca japonica*, *Ochetellus glaber*, *Pristomnyrmex pungens*, *Pheidole noda*, *Acromyrmiex* spp., *Solenopsis* spp., and *Linepithema humile*, Vespidae, Bethylidae, and Tenthredinidae such as *Athalia rosae* and *Athalia japonica*.

Blattodea pests: *Blattella germanica*, *Periplaneta fuliginoesa*, *Periplanieta americana*, *Periplaneta brunneca*, and *Blatta orienitalis*.

Isoptera pests: *Reticulitermes speratus*, *Coptotermes formosanus*, *Incisitermes minor*, *Cryptotermes domesticus*, *Odontotermes formosanus*, *Neotermes koshunensis*, *Glyptotermes satsumensis*, *Glyptotermes nakajimai*, *Glyptotermes fuscus*, *Glyptotermes kodiimai*, *Glyptotermes kushimensis*, *Hodotermopsis japonicai*, *Coptotermes guangzhoensis*, *Reticulitermes miyatakei*, *Reticulitermes flaviceps amamianus*, *Reticulitermes* sp., *Nasutitermes takasagoenisis*, *Pericapritermes nitobei*, *Sinocapritermes mushae*, and the like.

Acarina pests: Tetranychidae such as *Tetranychus urticae*, *Tetranychus kanzawai*, *Panonychus citri*, *Panonychus ulmi*, and *Oligonychus* spp., Eriophyidae such as *Aculops pelekassi*, *Phyllocoptruta citri*, *Aculops lycopersici*, *Calacarus carinatus*, *Acaphylla theavagrans*, *Eriophyes chibaensis*, and *Aculus schlechtendali*, Tarsonemridae such as *Polyphagotarsonemus latus*, Teruipalpidae such as *Brevipalpus phoenicis*, Tuckerellidae, Metastigmrata such as *Haemaphysalis longicornis*, *Haemaphysalis flava*, *Dermacentor taiwanicus*, *Dermacentor variabilis*, *Ixodes ova-

*tus, Ixodes persulcatus, Ixodes scapularis, Amblyomma americanum, Boophilus microplus,* and *Rhipicephalus sanguineus*, Acaridae such as *Tyrophagus putrescentiae* and *Tyrophagus similis*, Pyroglyphidae such as *Dermatophagoides farinae* and *Dermatophagoides ptrenyssnus*, Cheyletidae such as *Cheyletus eruditus, Cheyletus malaccensis, Cheyletus muoorei*, and *Cheyletiella yasguri*, Sarcoptidae such as *Octodectes cynotis* and *Sacroptes scabiei*, Demodicidae such as *Demodex canis*, Listrophoridae, Oribatei, Dermanyessidae such as *Ornithonyssus bacoti, Ornithonyssus sylvairum*, and *Dermanyssus gallinae*, Trombiculidae such as *Leptotrombidium akamushi*, and the like.

Acarina pests: *Chiracanthium japonicum, Latrodectus hasseltii*, and the like.

Chilopoda, Scutigeromorpha pests: *Thereuonema hilgendorfi*, and the like. Scolopendromorpha pests:

*Scolopendra subspinipes*, and the like.

Diplopoda, Polydesmoidea pests: *Oxidus gracilis, Nedyopus tambanus*, and the like.

Malacostraca, Isopoda pests: *Armadillidium vulgare*, and the like.

Gastropoda, Stylommatophora pests: *Limax marginatus, Limax flavus*, and the like.

The control agent of the present invention contains the present compound and an inert carrier.

In the present invention, the inert carrier means a solid carrier, a liquid carrier, and a gaseous carrier.

The control agent of the present invention is usually obtained by mixing the present compound and an inert carrier, and adding a surfactant or other auxiliaries for formulation as necessary, to be formulated into emulsifiable concentrates, oil formulations, powder formulations, granules, wettable powders, flowables, microcapsule formulations, aerosols, fumigants, poisonous baits, resin formulations, shampoo agent, paste formulation, foam agent, carbon dioxide preparation, tablet, and the like. These formulations may be processed into mosquito repellent coil, electric mosquito repellent mat, mosquito repellent liquid formulation, smoking agent, fumigant, sheet formulation, spot-on agent, or oral treatment agent, and used.

The control agent of the present invention usually contains the present compound in an amount of 0.01 to 95% by weight.

Examples of the solid carrier which is used in the formulation include fine powder and granulated substances of clays (kaolin clay, diatomaceous earth, bentonite, Fubasami clay, acid clay, etc.), synthetic hydrated silicon oxide, talc, ceramics, other inorganic minerals (sericite, quartz, sulfur, activated carbon, calcium carbonate, hydrated silica, etc.), chemical fertilizers (ammonium sulfate, ammonium phosphate, ammonium nitrate, urea, ammonium chloride, etc.) and the like, polyester resins such as synthetic resins (polyester resins such as polypropylene, polyacrylonitrile, polymethyl methacrylate and polyethylene terephthalate, nylon resins such as nylon-6, nylon-11 and nylon-66, polyamide resin, polyvinyl chloride, polyvinylidene chloride, vinyl chloride-propylene copolymer, and the like).

Examples of the liquid carrier include water, alcohols (methanol, ethanol, isopropyl alcohol, butanol, hexanol, benzyl alcohol, ethylene glycol, propylene glycol, phenoxyethanol, etc.), ketones (acetone, methyl ethyl ketone, cyclohexanone, etc.), aromatic hydrocarbons (toluene, xylene, ethylbenzene, dodecylbenzene, phenylxylylethane, methylnaphthalene, etc.), aliphatic hydrocarbons (hexane, cyclohexane, kerosene, light oil, etc.), esters (ethyl acetate, butyl acetate, isopropyl myristate, ethyl oleate, diisopropyl adipate, diisobutyl adipate, propylene glycol monomethyl ether acetate, etc.), nitriles (acetonitrile, isobutyronitrile, etc.), ethers (diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, 3-methoxy-3-methyl-1-butanol, etc.), acid amides (N,N-dimethylformamide, N,N-dimethylacetamide, etc.), halogenated hydrocarbons (dichloromethane, trichloroethane, carbon tetrachloride, etc.), sulfoxides (dimethyl sulfoxide, etc.), and propylene carbonate and vegetable oils (soybean oil, cottonseed oil, etc.).

Examples of the gaseous carrier include fluorocarbon, butane gas, LPG (liquefied petroleum gas), dimethyl ether, and carbon dioxide.

Examples of the surfactant include nonionic surfactants such as polyoxyethylene alkyl ether, polyoxyethylene alkylaryl ether and polyethylene glycol fatty acid ester, and anionic surfactants such as alkyl sulfonates, alkylbenzene sulfonates and alkylsulfates.

The other auxiliaries for formulation include such as fixing agents, dispersants, colorants and stabilizers, specifically, for example, casein, gelatin, saccharides (starch, arabic gum, cellulose derivatives, alginic acid, etc.), lignin derivatives, bentonite, synthetic water-soluble polymers (polyvinyl alcohol, polyvinyl pyrrolidone, polyacrylic acids, etc.), PAP (isopropyl acid phosphate), BHT (2,6-di-tert-butyl-4-methylphenol) and BHA (mixtures of 2-tert-butyl-4-methoxyphenol and 3-tert-butyl-4-methoxyphenol).

Examples of a base material of the resin formulation include vinyl chloride polymer, polyurethane and the like, and a plasticizer such as ester phthalates (dimethyl phthalate, dioctyl phthalate, etc.), ester adipates or stearic acid may be added to these base materials as necessary. The resin formulation is obtained by kneading a compound into the base material using an ordinary kneading apparatus, then molding it by injection molding, extrusion molding, press molding or the like, and can be processed into a plate, film, taped, reticular or string resin formulation by further undergoing molding or cutting step as necessary. These resin formulation is processed into, for example, a collar for animal, an ear tag for animal, a sheet formulation, an induction cord, and a gardening pole.

Examples of a base material of the poisonous bait include grain powder, vegetable oil, sugar, crystalline cellulose and the like, and further, an antioxidant such as dibutylhydroxytoluene and nordihydroguaiaretic acid, a preservative such as dehydroacetic acid, a substance for preventing accidental ingestion by children and pets such as red pepper powder, a pest attractant such as cheese flavor, onion flavor and peanut oil or the like are added as necessary.

The method for controlling arthropod pests of the present invention is carried out by applying an effective amount of the present compound to an arthropod pest directly and/or an arthropod pest-infested area (plants, soil, in-house, animal body, etc.). In the method for controlling arthropod pests of the present invention, the compound is usually used in the form of the control agent of the present invention.

When the control agent of the present invention is used in the control of arthropod pests in the agricultural field, the application amount thereof is usually 1 to 10000 g per the amount of the present compound per 10000 $m^2$. When the control agent of the present invention is formulated into an emulsifiable concentrate, a wettable powder, a flowable or the like, the pest control agent is usually diluted with water for an application so as to have a concentration of the active ingredient of 0.01 to 10000 ppm, and granules, powder formulations and the like are usually applied as they are.

These formulations and formulation solutions diluted with water may be directly treated by being sprayed on an arthropod pest or a plant such as crops which should be protected from arthropod pests, and also may be treated on a soil in order to control an arthropod pest that inhabits in the soil of cultivated land.

Also, the resin formulation processed into a sheet or string can be also treated by a method such as winding it around crops, spreading it in the vicinity of crops, or spreading it to the soil around crop roots.

When the control agent of the present invention is used in the control of the arthropod pests that inhabit in the house, the application amount thereof is usually 0.01 to 1000 mg in an amount of the present compound per 1 $m^2$ of an area to be treated, in the case of using it on a planar area, and is usually 0.01 to 500 mg in an amount of the present compound per 1 $m^3$ of a space to be treated, in the case of using it in a space. When the control agent of the present invention is formulated into an emulsifiable concentrate, a wettable powder, a flowable or the like, the pest control agent is usually diluted with water for an application so as to have a concentration of the active ingredient of 0.1 to 10000 ppm, and oil formulations, aerosols, fumigants, poisonous baits and the like are applied as they are.

When the arthropod pest control agent of the present invention is used in the control of external parasites on livestock such as cows, horses, pigs, sheep, goats and chickens, and small animals such as dogs, cats, rats and mice, veterinary known methods can be applied to the animals. As specific methods, the formulation is administered, for example, by way of a tablet, mixing in feed, a suppository and injection (intramuscular, subcutaneous, intravenous, intraperitoneal injections, etc.), when systemic control is intended, and the formulation is used, for example, by way of spraying an oil formulation or aqueous solution, pour-on or spot-on treatment, washing an animal with a shampoo formulation, or putting a collar or ear tag made of a resin formulation on to an animal, when non-systemic control is intended. The amount of the present compound when administered to an animal body is usually in the range from 0.1 to 1000 mg per 1 kg of the weight of an animal.

The control agent of the present invention can be used in the farmland where the following "crops" are grown.

Crops: corn, rice, wheat, barley, rye, oat, sorghum, cotton, soybean, peanut, sarrazin, sugar beet, rapeseed, sunflower, sugar cane, tobacco, etc.

Vegetables: Solanaceae vegetables (eggplant, tomato, green pepper, hot pepper, potato, etc.), Cucurbitaceae vegetables (cucumber, pumpkin, zucchini, watermelon, melon, etc.), Cruciferae vegetables (Japanese radish, turnip, horseradish, kohlrabi, Chinese cabbage, cabbage, brown mustard, broccoli, cauliflower, etc.), Compositae vegetables (burdock, garland chrysanthemum, artichoke, lettuce, etc.), Liliaceae vegetables (Welsh onion, onion, garlic, asparagus, etc.), Umbelliferae vegetables (carrot, parsley, celery, parsnip, etc.), Chenopodiaceae vegetables (spinach, Swiss chard, etc.), Labiatae vegetables (Japanese mint, mint, basil, etc.), strawberry, sweat potato, yam, aroid, etc.

Fruit trees: pomaceous fruits (apple, common pear, Japanese pear, Chinese quince, quince, etc.), stone fleshy fruits (peach, plum, nectarine, Japanese plum, cherry, apricot, prune, etc.), citrus plants (Satsuma mandarin, orange, lemon, lime, grapefruits, etc.), nuts (chestnut, walnut, hazel nut, almond, pistachio, cashew nut, macadamia nut, etc.), berry fruits (blueberry, cranberry, blackberry, raspberry, etc.), grape, persimmon, olive, loquat, banana, coffee, date, coconut, oil palm, etc.

Trees other than fruit trees: tea, mulberry, flowering trees and shrubs (azalea, camellia, hydrangea, sasanqua, Illicium religiosum, cherry tree, tulip tree, crape myrtle, fragrant olive, etc.), street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew, elm, horse-chestnut, etc.), sweet viburnum, Podocarpus macrophyllus, Japanese cedar, Japanese cypress, croton, spindle tree, Chainese howthorn, etc.

Lawn: zoysia (Japanese lawn grass, mascarene grass, etc.), Bermuda grass (Cynodon dactylcn, etc.), bent grass (creeping bent grass, Agrostis stolonifera, Agrostis tenuis, etc.), bluegrass (Kentucky bluegrass, rough bluegrass, etc.), fescue (tall fescue, chewing fescue, creeping fescue, etc.), ryegrass (darnel, perennial ryegrass, etc.), cocksfoot, timothy grass, etc.

Others: flowers (rose, carnation, chrysanthemum, Eustoma grandiflorum Shinners (prairie gentian), gypsophila, gerbera, pot marigold, salvia, petunia, verbena, tulip, aster, gentian, lily, pansy, cyclamen, orchid, lily of the valley, lavender, stock, ornamental kale, primula, poinsttia, gladiolus, cattleya, daisy, cymbidium, begonia, etc.), biofuel plants (Jatropha, curcas, safflower, Camelina alyssum, switchgrass, miscanthus, reed canary grass, Arundo donax, kenaf, cassava, willow, algae, etc.), foliage plants, etc.

The "crops" also contains genetically modified crops.

The control agent of the present invention can be used as a mixture with or in combination with other insecticide, miticide, nematicide, fungicide, plant growth regulator, herbicide or synergist. Examples of the active ingredient of said insecticide, miticide, nematicide, fungicide, herbicide and synergist are shown below.

Active Ingredients of Insecticide (1) Organic Phosphorus Compounds acephate, Aluminium phosphide, butathiofos, cadusafos, chlorethoxyfos, chlorfenvinphos, chlorpyrifos, chlorpyrifos-methyl, cyanophos: CYAP, diazinon, DCIP (dichlorodiisopropyl ether), dichlofenthion: ECP, dichlorvos: DDVP, dimethoate, dimethylvinphos, disulfoton, EPN, ethion, ethoprophos, etrimfos, fenthion: MPP, fenitrothion: MEP, fosthiazate, formothion, Hydrogen phosphide, isofenphos, isoxathion, malathion, mesulfenfos, methidathion: DMTP, monocrotophos, naled: BRP, oxydeprofos: ESP, parathion, phosalone, phosmet: PMP, pirimiphos-methyl, pyridafenthion, quinalphos, phenthoate, profenofos, propaphos, prothiofos, pyraclorfos, salithion, oulprofos, tebupirimfos, temephos, tetrachlorvinphos, terbufos, thiometon, trichlorphon: DEP, vamidothion, phorate, and cadusafos.

(2) Carbamate Compounds alanycarb, bendiocarb, benfuracarb, BPMC, carbaryl, carbofuran, carbasuifan, cloethocarb, ethiofencarb, fenobucarb, fenothiocarb, fenoxycarb, furathiocarb, isoprocarb: MIPC, muetolcarb, methomuyl, methiocarb, NAC, oxamyl, pirimicarb, propoxur: PHIC, XMC, thiodicarb, xylylcarb, and aldicarb.

(3) Pyrethroid Compounds acrinathrin, allethrin, benfluthrin, beta-cyfluthrin, bifenthrin, cycloprothrin, cyfluthrin, cyhalothrin, cypermethrin, deltamtethrin, esfenvalerate, ethofenprox, fenpropathrin, fenvalezate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramuethrin, phenothxrin, cyphtenothrin, alpha-cypermethrin, zeta-cypermethrin, lambda-cyhalothrin, gamma-cyhalothrin, furamethrin, tau-fluvalinate, metofluthrin, profluthrin, dimefluthrin, 2,3,5,6- tetrafluoro-4-(methoxymethyl)benzyl (EZ)-(1RS,3RS; 1RS, 3SR)-2,2-dimethyl-3-prop-1-enylcyclopropanecarboxylate, 2,3,5,6-tetrafluoro-4-methylbenzyl (EZ)-(1RS,3RS; 1RS, 3SR)-2,2-dimethyl-3-prop-1-enylcyclopropanecarboxylate, and 2,3,5,6-tetrafluoro-4-(methoxymethyl)benzyl (1RS, 3RS; 1RS, 3SR)-2,2-dimethyl-3-(2-methyl-1-propenyl)cyclopropanecarboxylate, 2,3,5,6-tetrefluoro-4-(methoxymethyl)benzyl (EZ)-(1RS, 3RS; 1RS, 3SR)-2,2-dimethyl-3-(2-cyano-1-propenyl)cyclopropanecarboxylate.

(4) Nereistoxin Compounds cartap, bensultap, thiocyclam, monosultap, and bisultap.

(5) Neosnicotinoid Compounds imidacloprid, nitenpyram, acetamiprid, thiamuethoxam, thiacloprid, dinotefuran, and clothianidin.

(6) Benzoyl Urea Compounds chlorfluazuron, bistrifluron, diafenthiuron, diflubenzuron, fluazuron, flucycloxuron, flufenoxuron, hexaflumuron, lufenuron, novaluron, noviflumuron, teflubenzuron, trifumuron, and triazuron.

(7) Phenylpyrazole Compounds acetoprole, ethiprole, fipronil, vaniliprole, pyriprole, and pyrafluprole.

(8) Bt Toxins

Living spores derived from *Bacillus thurirngiensis* and produced crystalline toxins and mixtures thereof;

(9) Hydrazine Compounds chromafenozide, halofenozide, methoxyfenozide, and tebufenozide.

(10) Organic Chlorine Compounds aldrin, dieldrin, dienochlor, endosulfan, and methoxychlor.

(11) Other Active Ingredients of Insecticide machine oil, nicotine-sulfate; avermectin-B, bromopropylate, buprofezin, chlorphenapyr, cyantraniliprole, cyromazine, D-D(1,3-Dichloropropene), emamectin-benzoate, fertazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, Arsenicacid, benclothiaz, Calciumcyanamide, Calcium polysulfide, chlordane, DDT, DSP, flufenerim, flonicamid, flurinfen, formetanate, metamammonium, metam-sodium, Methyl bromide, Potassium oleate, protrifenbute, spiromiesifen, sulfoxaflor, Sulfur, metaflumizone, spirotetramat, pyrifluquinazone, spinetoram, chlorantraniliprole, tralopyril, cyantraniliprole, compounds represented by the following formula (K)

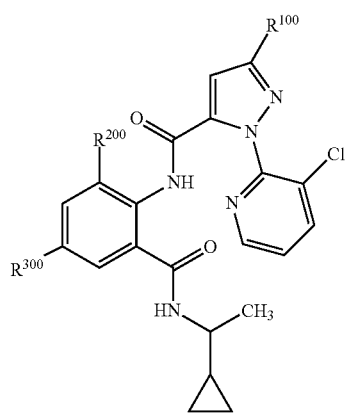

wherein $R^{100}$ represents chlorine, bromine or a trifluoromethyl group, $R^{200}$ represents chlorine, bromine or a methyl group, and $R^{300}$ represents chlorine, bromine or a cyano group, and compounds represented by the following formula (L)

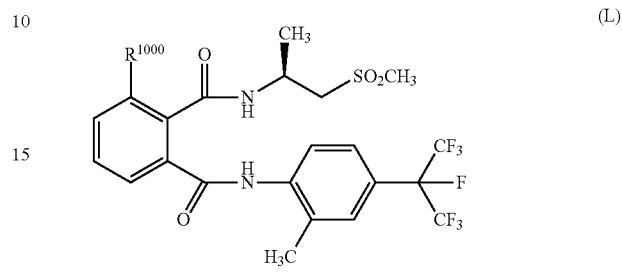

wherein $R^{1000}$ represents chlorine, bromine or iodine.

Active Ingredients of Miticide acequinocyl, amitraz, benzoximate, bifenaate, bromopropylate, chinomethionat, chlorobenzilate, CPCBS (chlorfenson), clofentezine, cyflumetofen, kelthane (dicofol), etoxazole, fenbutatin oxide, fenothiocarb, fenpyroximate, fluacrypyrim, fluproxyfen, hexythiazox, propargite: BPPS, polynactins, pyridaben, Pyrimidifen, tebufenpyrad, tetradifon, spirodiclofen, spiromesifen, spirotetramat, amidoflumet, and cyenopyrafen.

Active Ingredients of Nematicide

DCIP, fosthiazate, levamisol, methyisothiocyanate, morantel tartarate, and imicyafos.

Active Ingredients of Fungicide azole fungicidal compounds such as propiconazole, prothioconazole, triadimeriol, prochloraz, penconazole, tebuconxazole, fluhsilazole, diniiconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, and flutriafol;

Cyclic amine fungicidal compounds such as fenpropimorph, tridemorph, and fenpropidin;

Benzimidazole fungicidal compounds such as carbendezim, benomyl, thiabendazole, and thiophanate-methyl;

procymidone; cyprodinil; pyrimethanil; diethofencarb; thiuram; fluazinam; mancozeb; iprodione; vinclozolin; chlorothalonil; captan; mepanipyrim; fenpiclonil; fludioxonil; dichiofluanid; folpet; kresoxim-methyl; azoxystrobin; trifloxystrobin; fluoxastrobin; picoxystrobin; pyraclostrobin; dimoxystrobin; pyribencarb; spiroxamine; quinoxyfen; fenhexamid; famoxadone; fenamidone; zoxamide; ethaboxam; amisulbrom; iprovalicarb; benthiavalicarb; cyazofamid; mandipropamid; boscaid; penthiopyrad; metrafenone; fluopiran; bixafen; cyflufenamid; proquinazid; isotianil and tiadinil.

Active Ingredients of Herbicide (1) Phenoxy Fatty Acid Hexbicidal Compounds 2,4-PA, MCP, MCPB, phenothiol, mecoprop, fluroxypyr, triclopyr, clomeprop, and naproanilide.

(2) Benzoate Herbicidal Compounds 2,3,6-TBA, dicamba, clopyralid, picloram, aminopyralid, (3) Urea Herbicidal Compounds
diuron, linuron, chlortoluron, isoproturon, fluometuron, isouron, tebuthiuron, methabenzthiazuron, cumyluron, daimuron, and methyl-daimuron.
(4) Triazine Herbicidal Compounds
atrazine, ametoryn, cyanazine, simazine, propazine, simetryn, dimethametryn, prometryn, metribuzin, triaziflan, and indaziflam.
(5) Bipyridinium Herbicidal Compounds
paraquat, and diquat.
(6) Hydroxybenzonitrile Herbicidal Compounds
bromoxynil, and ioxynil.
(7) Dinitroraniline Herbicidal Compounds
pendimethalin, prodiamine, and trifluralin.
(8) Organophosphorus Herbicidal Compounds
amiprofos-methyl, butamifos, bensulide, piperophos, anilofos, glyphosate, glufosinate, glufosinate-P, and bialaphos.
(9) Carbamate Herbicidal Compounds
di-allate, tri-allate, EPTC, butylate, benthiocarb, esprocarb, molinate, dimepiperate, swep, chlorpropham, phenmedipham, phenisopham, pyributicarb, and asulam.
(10) Acid Amide Herbicidal Compounds
propanil, propyzamide, bromiobutide, and etobenzanid.
(11) Chloroacetanilide Herbicidal Compounds
acetochlor, alachlor, butachlor, dimethenamid, propachlor, metazachlor, metolachlor, pretilachlor, thenylchlor, and pethoxamid.
(12) Diphenyl Ether Herbicidal Compounds
acifluorfen-sodium, bifenox, oxyfluorfen, lactofen, fomesafen, chlomethoxynil, and aclonifen.
(13) Cyclic Imide Herbicidal Compounds
oxadiazon, cinidon-ethyl, carfentrazone-ethyl, surfentrazone, flumiclorac-pentyl, flumioxazin, pyraflufen-ethyl, oxadiargyl, pentoxazono, flutiacet-methyl, butafenacil, benzfendizone, bencarbazone, and saflufenacil.
(14) Pyrazole Herbicidal Compounds
benzofenap, pyrazolate, pyrazoxyfen, topramezone, and pyrasulfotole.
(15) Triketone Herbicidal Compounds
isoxaflutole, benzobicyclon, sulcotrione, mesotrione, tembotrione, and tefuryltrione.
(16) Aryloxyphenoxypropionate Herbicidal Compounds
clodiniafop-propargyl, cyhalofop-butyl, diclofop-methyl, fenoxaprop-ethyl, fluazifop-butyl, haloxyfop-methyl, and quizalofop-ethyl, metamifop.
(17) Trione Oxime Herbicidal Compounds
alloxydim-sodium, sethoxydim, butroxydim, clethodim, cloproxydim, cycloxydim, tepraloxydim, tralkoxydim, and profoxydim.
(18) Sulfonyl Urea Herbicidal Compounds
chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, and propyrisulfuron.
(19) Imidazolinone Herbicidal Compounds
imazamethabenz-methyl, imazamethapyr, imazamox, imazapyr, imazaquin, and imazethapyr.
(20) Sulfonamide Herbicidal Compounds
flumetsulam, metosulam, diclosulam, florasulam, cloransulam-methyl, penoxsulan, and pyroxsulam.

(21) Pyrimidinyloxybenzoate Herbicidal Compounds
pyrithiobac-sodium, bispyribac-sodium, pyriminobac-methyl, pyribenzoxim, pyriftalid, and pyrimisulfan.
(22) Other Herbicidal Compounds
berttazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrote, indanofan, oxaziclomefone, benfuresate, ACN, pyridate, chloridazon, norflurazon, flurtamone, diflufenican, picolinafen, beflubutamuid, clomazone, amicarbazone, pinoxaden, pyraclonil, pyroxasulfone, thiencarbazone-methyl, aminocyclopyrachlor, ipfencarbazone, and methiozolin.

Active Ingredients of Synergist piperonyl butoxide, sesamex, sulfoxide, N-(2-ethylhexyl)-8,9,10-trinorborn-5-ene-2,3-dicarboximide (MCK 264), N-declyimidazole), WARF-antiresistant, Tribufos (TBPT), triphenyl phosphite (TPP), iprobenfos (IHP), (methyl iodide) $CH_3I$, t-phenylbutenone, diethylmaleate, bis(p-chlorophenyl)methyl carbinol (DMC), and bis(p-chlorophenyl)trifluoromethyl carbinol (FDMC).

EXAMPLES

Hereinbelow, the compound of the control agent of the present invention will be further described in detail by production examples, formulation examples, test examples, and the like. However, the present invention is not limited to these examples.

First, the production examples for the production of the present compounds will be shown.

Production Example 1 (1)

A mixture of 0.40 g of 3-(ethylsulfanyl)pyridine-2-carbonyl chloride and 5 mL of THF was added to a mixture of 0.37 g of 5-(trifluoromethyl)pyridine-2-carbohydrazide and 20 mL of THF under ice cooling, subsequently, 0.27 g of pyridine was added thereto under ice cooling, and the mixture was stirred at room temperature for 2 hours. A saturated aqueous sodium bicarbonate solution was added to the reaction mixture, and the mixture was extracted with ethyl acetate. The organic layer was dried over anhydrous sodium sulfate and concentrated under reduced pressure to obtain 0.55 g of an intermediate (1) shown below.

Intermediate (1)

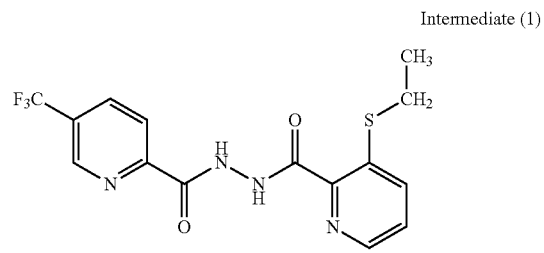 [SMILES: CCSc1cccnc1C(=O)NNC(=O)c1ccc(C(F)(F)F)cn1]

$^1$H-NMR (CDCl$_3$) δ: 10.46 (2H, brs), 8.88 (1H, s), 8.36-8.31 (2H, m), 8.14 (1H, d), 7.70 (1H, d), 7.41 (1H, dd), 2.95 (2H, q), 1.42 (3H, t)

Production Example 1 (2)

0.41 g of the intermediate (1) was added to 10 g of phosphorus oxychloride, and the mixture was stirred under heat-reflux for 1 hour. The reaction mixture cooled to room temperature was concentrated under reduced pressure, and a saturated aqueous sodium bicarbonate solution was added to the resulting residue, then the mixture was extracted with ethyl acetate. The organic layer was dried over anhydrous sodium sulfate and concentrated under reduced pressure. The resulting residue was applied to a silica gel column chromatography to obtain 0.12 g of a compound shown below (hereinafter, referred to as present compound 1-1).

Present Compound 1-1

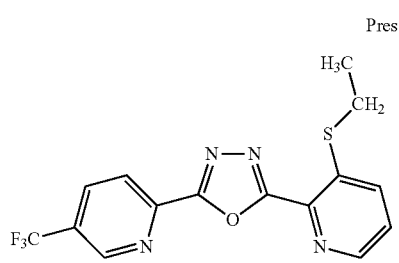

$^1$H-NMR (CDCl$_3$) δ: 9.08 (1H, s), 3.59 (1H, d), 8.49 (1H, d), 8.16 (1H, d), 7.80 (1H, d), 7.42 (1H, dd), 3.07 (2H, q), 1.45 (3H, t)

Production Example 2

0.23 g of m-chloroperoxybenzoic acid (purity of 65% or more) was added to a mixture of the present compound 1-1 (0.10 g) and 10 mL of chloroform under ice cooling, and the mixture was stirred at room temperature for 2 hours. A 10% aqueous sodium thiosulfate solution was added to the reaction mixture, and the mixture was stirred at room temperature for 10 minutes. The organic layer was sequentially washed with a saturated aqueous sodium bicarbonate solution, water and a saturated aqueous sodium chloride solution and dried over anhydrous sodium sulfate, then concentrated under reduced pressure. The resulting residue was applied to a silica gel column chromatography to obtain 0.02 g of the present compound 1-2 and 0.06 g of the present compound 1-3 shown below.

Present Compound 1-2

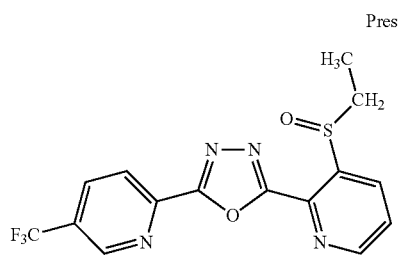

$^1$H-NMR (CDCl$_3$) δ: 9.10 (1H, s), 8.94 (1H, dd), 8.65 (1H, dd), 8.48 (1H, d), 8.19 (1H, dd), 7.77 (1H, dd), 3.53-3.42 (1H, m), 3.09-2.98 (1H, m), 1.40 (3H, t)

Present Compound 1-3

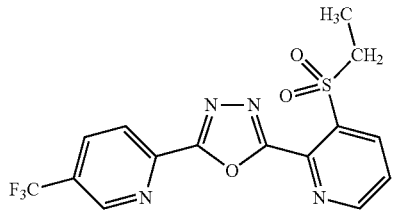

$^1$H-NMR (CDCl$_3$) δ: 9.07 (1H, s), 9.05 (1H, dd), 8.58 (1H, dd), 8.47 (1H, d), 8.18 (1H, dd), 7.77 (1H, dd), 3.90 (2H, q), 1.42 (3H, t)

Production Example 3

0.32 g of Lawesson's reagent was added to a mixture of 0.14 g of the intermediate (1) and 5 mL of 1,4-dioxane, and the mixture was stirred at 100° C. for 1 hour. The reaction mixture was cooled to room temperature, and water and a saturated aqueous sodium bicarbonate solution were added thereto, and the mixture was extracted with ethyl acetate. The organic layer was dried over anhydrous sodium sulfate and concentrated under reduced pressure to obtain 0.14 g of a compound (hereinafter, referred to as present compound 1-40) shown below.

Present Compound 1-40

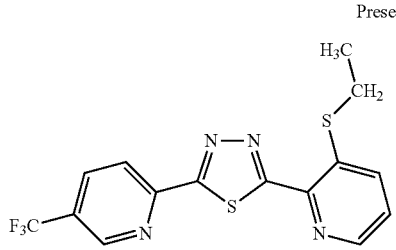

$^1$H-NMR (CDCl$_3$) δ: 8.94 (1H, s), 8.56 (1H, d), 8.46 (1H, d), 8.11 (1H, d), 7.76 (1H, d), 7.34 (1H, dd), 3.05 (2H, q), 1.46 (3H, t)

Production Example 4

0.27 g of m-chloroperoxybenzoic acid (purity of 65% or more) was added to a mixture of the present compound 1-40 (0.14 g) and 10 mL of chloroform under ice cooling, and the mixture was heated to room temperature and stirred at room temperature for 2 hours. A 10% aqueous sodium thiosulfate solution was added to the reaction mixture, and the mixture was stirred at room temperature for 10 minutes. The organic layer was sequentially washed with a saturated aqueous sodium bicarbonate solution, water and a saturated aqueous sodium chloride solution and dried over anhydrous sodium sulfate, then concentrated under reduced pressure. The resulting residue was applied to a silica gel column chromatography to obtain 0.17 g of a compound shown below (hereinafter, referred to as present compound 1-4).

Present Compound 1-4

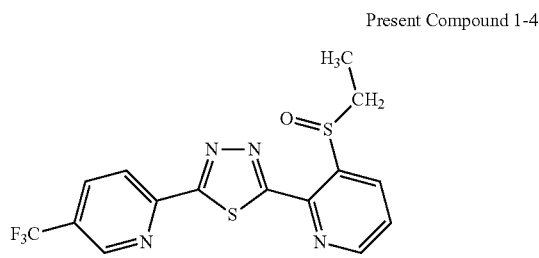 [SMILES: CCS(=O)c1cccnc1-c1nnc(-c2ccc(C(F)(F)F)cn2)s1]

¹H-NMR (CDCl₃) δ: 8.97 (1H, s), 8.79 (1H, dd), 8.64 (1H, dd), 8.54 (1H, d), 8.15 (1H, dd), 7.68 (1H, dd), 3.54-3.43 (1H, m), 3.10-2.99 (1H, m), 1.39 (3H, t)

Production Example 5

0.23 g of m-chloroperoxybenzoic acid (purity of 65% or more) was added to a mixture of the present compound 1-4 (0.15 g) and 10 mL of chloroform under ice cooling, and the mixture was stirred at room temperature for 1 day. A 10% aqueous sodium thiosulfate solution was added to the reaction mixture, and the mixture was stirred at room temperature for 10 minutes. The organic layer was sequentially washed with a saturated aqueous sodium bicarbonate solution, water and a saturated aqueous sodium chloride solution and dried over anhydrous sodium sulfate, then concentrated under reduced pressure. The resulting residue was applied to a silica gel column chromatography to obtain 0.1.3 g of a compound shown below (hereinafter, referred to as present compound 1-5).

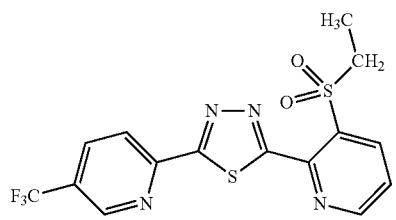 [SMILES: CCS(=O)(=O)c1cccnc1-c1nnc(-c2ccc(C(F)(F)F)cn2)s1]

¹H-NMR (CDCl₃) δ: 8.95 (1H, s), 8.93 (1H, dd), 8.62 (1H, dd), 8.54 (1H, d), 8.15 (1H, dd), 7.67 (1H, dd), 4.08 (2H, q), 1.43 (3H, t)

Production Example 6

A mixture of 0.50 g of 2-(ethylsulfanyl)-4-(trifluoromethyl)benzoyl chloride and 5 mL of DMF was added to a mixture of 0.41 g of N'-hydroxy-5-(trifluoromethyl pyridine-2-carboximidamide and 5 mL of DMF, subsequently, 0.30 g of triethylamine was added thereto, and the mixture was stirred under heat-reflux for 2 hours. The reaction mixture was cooled to room temperature, and a saturated aqueous sodium bicarbonate solution was added thereto, and the mixture was extracted with ethyl acetate. The organic layer was dried over anhydrous sodium sulfate and concentrated under reduced pressure. The resulting residue was applied to a silica gel column chromatography to obtain 0.21 g of a compound shown below (hereinafter, referred to as present compound 1-6).

Present Compound 1-6

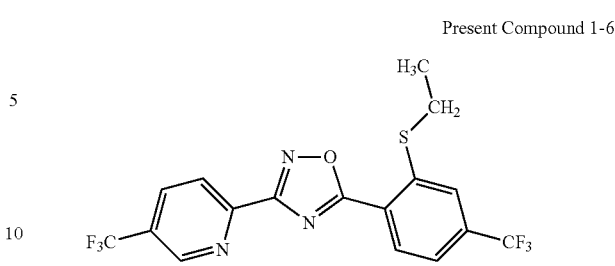

¹H-NMR (CDCl₃) δ: 9.10 (1H, s), 8.40 (1H, d), 8.32 (1H, d), 8.16 (1H, d), 7.66 (1H, s), 7.54 (1H, d), 3.12 (2H, q), 1.46 (3H, t).

Production Example 7

0.14 g of m-chloroperoxybenzoic acid (purity of 65% or more) was added to a mixture of the present compound 1-6 (0.10 g) and 10 mL of chloroform under ice cooling, and the mixture was stirred at room temperature for 2 hours. A 10% aqueous sodium thiosulfate solution was added to the reaction mixture, and the mixture was stirred at room temperature for 10 minutes. The organic layer was sequentially washed with a saturated aqueous sodium bicarbonate solution, water and a saturated aqueous sodium chloride solution and dried over anhydrous sodium sulfate, then concentrated under reduced pressure. The resulting residue was applied to a silica gel column chromatography to obtain 0.10 g of a compound shown below (hereinafter, referred to as present compound 1-7).

Present Compound 1-7

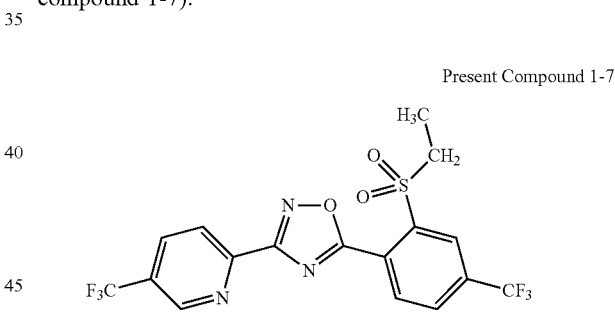

¹H-NMR (CDCl₃) δ: 9.09 (1H, S), 8.51 (1H, s), 8.33 (1H, d), 8.19-8.10 (3H, m), 3.73 (2H, q), 1.44 (3H, t).

Production Example 8 (1)

5.29 g of m-chloroperoxybenzoic acid (purity of 65% or more) was added to a mixture of 2.31 g of 2-cyano-3-(ethylsulfanyl)pyridine and 20 mL of chloroform under ice cooling, and the mixture was stirred at room temperature for 2 hours. A 10% aqueous sodium thiosulfate solution was added to the reaction mixture, and the mixture was stirred at room temperature for 10 minutes. The organic layer was sequentially washed with a saturated aqueous sodium bicarbonate solution, water and a saturated aqueous sodium chloride solution and dried over anhydrous sodium sulfate, then concentrated under reduced pressure. The resulting residue was applied to a silica gel column chromatography to obtain 1.49 g of an intermediate (2) shown below.

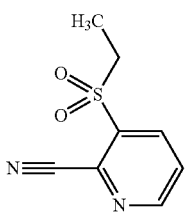

Intermediate (2)

$^1$H-NMR (CDCl$_3$) δ: 8.97 (1H, dd), 8.47 (1H, dd), 7.77 (1H, dd), 3.48 (2H, q), 1.38 (3H, t).

Production Example 8 (2)

1.93 g of sodium bicarbonate was added to a mixture of 1.61 g of hydroxylamine hydrochloride and 15 mL of ethanol, and the mixture was stirred under heat-reflux for 45 minutes. The reaction mixture was cooled to room temperature, then ice-cooled, and 2.15 g of the intermediate (2) was added thereto, then the mixture was stirred at room temperature for 2 hours. Water and a saturated aqueous ammonium chloride solution were added to the reaction mixture, and the mixture was extracted with ethyl acetate. The organic layer was dried over anhydrous sodium sulfate and concentrated under reduced pressure to obtain 2.02 g of an intermediate (3) shown below.

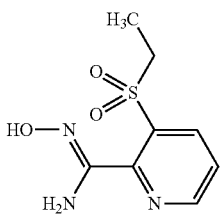

$^1$H-NMR (CDCl$_3$) δ: 8.83 (1H, d), 8.47 (1H, d), 7.56 (1H, dd), 6.70 (1H, brs), 5.27 (2H, brs), 3.75 (2H, q), 1.29 (3H, t).

Production Example 8 (3)

A mixture of 0.26 g of 3,5-bis(trifluoromethyl)benzoyl chloride and 1 mL of DMF was added to a mixture of 0.23 g of the intermediate (3) and 2 mL of DMF, subsequently, 0.15 g of triethylamine was added thereto, and the mixture was stirred at 80° C. for 2 hours and under heat-reflux for 2 hours. A saturated aqueous sodium bicarbonate solution was added to the reaction mixture cooled to room temperature, and the mixture was extracted with ethyl acetate. The organic layer was dried over anhydrous sodium sulfate and concentrated under reduced pressure. The resulting residue was applied to a silica gel column chromatography to obtain 0.21 g of a compound shown below (hereinafter, referred to as present compound 1-15).

Present Compound 1-15

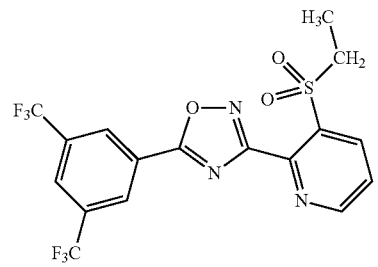

$^1$H-NMR (CDCl$_3$) δ: 9.07 (1H, dd), 8.70 (2H, s), 8.55 (1H, dd), 8.14 (1H, s), 7.76 (1H, dd), 3.73 (2H, q), 1.42 (3H, t).

The compounds produced according to the method described in the production examples described above are shown in [Table 1] to (Table 2).

Compounds represented by formula (1-X),

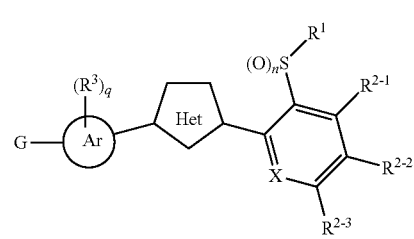

(1-X)

wherein $R^{2-1}$, $R^{2-2}$ and $R^{2-3}$ each independently represent the same meaning as $R^2$, and other symbols represent the same meaning as in the formula (1).

In the formula, $R^1$, n, $R^{2-1}$, $R^{2-2}$, $R^{2-3}$, X, Het and $(R^3)_q$GAr-represent the combinations shown in [Table 1] to [Table 2] be low.

TABLE 1

| Present Compound | $R^1$ | n | $R^{2-1}$ | $R^{2-2}$ | $R^{2-3}$ | X | Het | $(R^3)_q$GAr- |
|---|---|---|---|---|---|---|---|---|
| 1-1 | CH$_2$CH$_3$ | 0 | H | H | H | N | H2—O | 5-(trifluoromethyl)pyridin-2-yl |
| 1-2 | CH$_2$CH$_3$ | 1 | H | H | H | N | H2—O | 5-(trifluoromethyl)pyridin-2-yl |
| 1-3 | CH$_2$CH$_3$ | 2 | H | H | H | N | H2—O | 5-(trifluoromethyl)pyridin-2-yl |
| 1-4 | CH$_2$CH$_3$ | 1 | H | H | H | N | H2—S | 5-(trifluoromethyl)pyridin-2-yl |
| 1-5 | CH$_2$CH$_3$ | 2 | H | H | H | N | H2—S | 5-(trifluoromethyl)pyridin-2-yl |
| 1-6 | CH$_2$CH$_3$ | 0 | H | CF$_3$ | H | CH | H3—O | 5-(trifluoromethyl)pyridin-2-yl |
| 1-7 | CH$_2$CH$_3$ | 2 | H | CF$_3$ | H | CH | H3—O | 5-(trifluoromethyl)pyridin-2-yl |
| 1-8 | CH$_2$CH$_3$ | 2 | H | H | H | N | H3—O | 5-(trifluoromethyl)pyridin-2-yl |
| 1-9 | CH$_2$CH$_3$ | 1 | H | CF$_3$ | H | CH | H2—S | 5-(trifluoromethyl)pyridin-2-yl |
| 1-10 | CH$_2$CH$_3$ | 0 | H | CF$_3$ | H | CH | H2—S | 5-(trifluoromethyl)pyridin-2-yl |
| 1-11 | CH$_2$CH$_3$ | 2 | H | H | H | N | H1—O | 5-(trifluoromethyl)pyridin-2-yl |
| 1-12 | CH$_2$CH$_3$ | 2 | H | H | H | N | H1—O | 4-(trifluoromethyl)phenyl |
| 1-13 | CH$_2$CH$_3$ | 2 | H | H | H | N | H1—O | 3-(trifluoromethyl)phenyl |
| 1-14 | CH$_2$CH$_3$ | 2 | H | H | H | N | H1—O | 2-(trifluoromethyl)phenyl |
| 1-15 | CH$_2$CH$_3$ | 2 | H | H | H | N | H1—O | 3,5-bis(trifluoromethyl)phenyl |

TABLE 1-continued

| Present Compound | R¹ | n | R²⁻¹ | R²⁻² | R²⁻³ | X | Het | (R³)qGAr- |
|---|---|---|---|---|---|---|---|---|
| 1-16 | CH₂CH₃ | 2 | H | CF₃ | H | CH | H1—O | 3,5-bis(trifluoromethyl)phenyl |
| 1-17 | CH₂CH₃ | 2 | H | H | H | N | H1—O | 4-(trifluoromethylsulfanyl)phenyl |
| 1-18 | CH₂CH₃ | 2 | H | CF₃ | H | CH | H1—O | 4-(trifluoromethylsulfanyl)phenyl |
| 1-19 | CH₂CH₃ | 2 | H | H | H | N | H3—O | 3,5-bis(trifluoromethyl)phenyl |
| 1-20 | CH₂CH₃ | 2 | H | CF₃ | H | CH | H3—O | 3,5-bis(trifluoromethyl)phenyl |
| 1-21 | CH₂CH₃ | 2 | H | CF₃ | H | N | H1—O | 3,5-bis(trifluoromethyl)phenyl |
| 1-22 | CH₂CH₃ | 2 | H | CF₃ | H | N | H3—O | 3,5-bis(trifluoromethyl)phenyl |
| 1-23 | CH₂CH₃ | 2 | H | H | H | CH | H3—O | 3,5-bis(trifluoromethyl)phenyl |
| 1-24 | CH₂CH₃ | 2 | H | H | H | CH | H1—O | 3,5-bis(trifluoromethyl)phenyl |
| 1-25 | CH₂CH₃ | 2 | H | H | H | N | H2—O | 3,5-bis(trifluoromethyl)phenyl |

TABLE 2

| Present Compound | R¹ | n | R²⁻¹ | R²⁻² | R²⁻³ | X | Het | (R³)qGAr- |
|---|---|---|---|---|---|---|---|---|
| 1-26 | CH₂CH₃ | 2 | H | H | H | N | H1—O | 3-fluoro-5-(trifluoromethyl)phenyl |
| 1-27 | CH₂CH₃ | 2 | H | H | H | N | H1—O | 3-bromo-5-(trifluoromethyl)phenyl |
| 1-28 | CH₂CH₃ | 2 | H | H | H | N | H1—O | 4-fluoro-3-(trifluoromethyl)phenyl |
| 1-29 | CH₂CH₃ | 2 | H | H | H | N | H1—O | 4-(trifluoromethyl)pyridin-2-yl |
| 1-30 | CH₂CH₃ | 2 | H | H | H | N | H1—O | 5-(trifluoromethyl)pyridin-3-yl |
| 1-31 | CH₂CH₃ | 2 | H | H | H | N | H1—O | 2-(trifluoromethyl)pyridin-4-yl |
| 1-32 | CH₂CH₃ | 2 | H | H | H | N | H1—O | 3-(trifluoromethylsulfanyl)phenyl |
| 1-33 | CH₂CH₃ | 2 | H | H | H | N | H1—O | 6-(trifluoromethyl)pyridin-2-yl |
| 1-34 | CH₂CH₃ | 2 | H | H | H | N | H1—O | 3,5-dibromophenyl |
| 1-35 | CH₂CH₃ | 2 | H | H | H | N | H1—O | 3,5-difluorophenyl |
| 1-36 | CH₂CH₃ | 2 | H | H | H | N | H1—O | 1-methyl-3-(trifluoromethyl)pyrazol-5-yl |
| 1-37 | CH₂CH₃ | 2 | H | H | H | N | H1—O | 5-(trifluoromethyl)thiophen-2-yl |
| 1-38 | CH₂CH₃ | 2 | H | H | H | N | H1—O | 3,5-dichlorophenyl |
| 1-39 | CH₂CH₃ | 2 | H | H | H | N | H2—S | 3,5-bis(trifluoromethyl)phenyl |
| 1-40 | CH₂CH₃ | 0 | H | H | H | N | H2—S | 5-(trifluoromethyl)pyridin-2-yl |
| 1-41 | CH₂CH₃ | 2 | H | H | H | N | H1—O | 4-chloro-1,3-benzodioxolan-6-yl |
| 1-42 | CH₂CH₃ | 2 | H | H | H | N | H1—O | 3-chloro-5-(trifluoromethyl)phenyl |
| 1-43 | CH₂CH₃ | 2 | H | H | H | N | H2—S | 3-chloro-5-(trifluoromethyl)phenyl |
| 1-44 | CH₂CH₃ | 2 | H | H | H | N | H2—S | 3-(trifluoromethyl)-1,2,4-triazol-1-yl |
| 1-45 | CH₂CH₃ | 2 | H | H | H | N | H2—S | 4-(trifluoromethyl)imidazol-1-yl |
| 1-46 | CH₂CH₃ | 2 | H | H | H | N | H2—S | 3-(trifluoromethyl)pyrazol-1-yl |
| 1-47 | CH₂CH₃ | 2 | H | H | H | N | H2—S | 4-(trifluoromethyl)pyrazol-1-yl |

¹H-NMR data of the present compound shown in [Table 1] to [Table 2] are shown below.

Present Compound 1-8

¹H-NMR (CDCl₃) δ: 9.10-9.04 (2H, m), 8.56 (1H, d), 8.35 (1H, d), 8.16 (1H, d), 7.81 (1H, dd), 3.78 (2H, q), 1.42 (3H, t).

Present Compound 1-9

¹H-NMR (CDCl₃) δ: 8.95 (1H, s), 8.57 (1H, d), 8.38 (1H, d), 8.14 (1H, dd), 7.80 (1H, s), 7.62 (1H, d), 3.03 (2H, q), 1.35 (3H, t).

Present Compound 1-10

¹H-NMR (CDCl₃) δ: 8.94 (1H, s), 8.55-8.51 (2H, m), 8.16 (1H, dd), 8.05 (1H, d), 7.82 (1H, d), 3.69 (2H, q), 1.38 (3H, t).

Present Compound 1-11

¹H-NMR (CDCl₃) δ: 9.11 (1H, d), 9.05 (1H, dd), 8.54 (1H, dd), 8.49 (1H, d), 8.21 (1H, dd), 7.75 (1H, dd), 3.75 (2H, q), 1.41 (3H, t).

Present Compound 1-12

¹H-NMR (CDCl₃) δ: 9.05 (1H, dd), 8.54 (1H, dd), 8.36 (2H, d), 7.84 (2H, d), 7.74 (1H, dd), 3.76 (2H, q), 1.41 (3H, t).

Present Compound 1-13

¹H-NMR (CDCl₃) δ: 9.06 (1H, d), 8.58-8.49 (2H, m), 8.42 (1H, d), 7.90 (1H, d), 7.78-7.70 (2H, m), 3.76 (2H, q), 1.41 (3H, t).

Present Compound 1-14

¹H-NMR (CDCl₃) δ: 9.04 (1H, dd), 8.53 (1H, dd), 8.17 (1H, dd), 7.93 (1H, dd), 7.80-7.75 (2H, m), 7.73 (1H, dd), 3.75 (2H, q), 1.38 (3H, t).

Present Compound 1-16

¹H-NMR (CDCl₃) δ: 8.64 (2H, s), 8.50 (1H, s), 8.16 (1H, s), 8.08 (1H, d), 8.02 (1H, d), 3.73 (2H, q), 1.43 (3H, t).

Present Compound 1-17

¹H-NMR (CDCl₃) δ: 9.05 (1H, dd), 8.54 (1H, dd), 8.28 (2H, d), 7.85 (2H, d), 7.73 (1H, dd), 3.75 (2H, q), 1.40 (3H, t).

Present Compound 1-18

¹H-NMR (CDCl₃) δ: 8.49 (1H, brs), 8.23 (2H, d), 8.06 (1H, dd), 8.02 (1H, d), 7.86 (2H, d), 3.77 (2H, q), 1.42 (3H, t).

Present Compound 1-19

¹H-NMR (CDCl₃) δ: 9.08 (1H, dd), 8.63 (2H, s), 8.58 (1H, dd), 8.06 (1H, s), 7.84 (1H, dd), 3.75 (2H, q), 1.46 (3H, t).

Present Compound 1-20

¹H-NMR (CDCl₃) δ: 8.60 (2H, s), 3.53 (1H, s), 8.13 (2H, s), 8.08 (1H, s), 3.73 (2H, q), 1.48 (3H, t).

Present Compound 1-21

¹H-NMR (CDCl₃) δ: 9.30 (1H, dd), 8.79 (1H, dd), 8.70 (2H, s), 8.14 (1H, s), 3.80 (2H, q), 1.46 (3H, t).

Present Compound 0.1-22

¹H-NMR (CDCl₃) δ: 9.31 (1H, d), 3.81 (1H, d), 8.61 (2H, s), 8.08 (1H, s), 3.82 (2H, q), 1.50 (3H, t).

Present Compound 1-23
¹H-NMR (CDCl₃) δ: 8.61 (2H, s), 8.27 (1H, dd), 8.06 (1H, s), 7.95 (1H, dd), 7.90-7.85 (2H, m), 3.68 (2H, q), 1.44 (3H, t).

Present Compound 1-24
¹H-NMR (CDCl₃) δ: 8.64 (2H, s), 6.25-8.22 (1H, in), 8.13 (1H, s), 7.85-7.77 (3H, m), 3.67 (2H, q), 1.40 (3H, t).

Present Compound 1-25
¹H-NMR (CDCl₃) δ: 9.05 (1H, dd), 8.63 (2H, s), 8.59 (1H, dd), 8.09 (1H, s), 7.80 (1H, dd), 3.68 (2H, q), 1.42 (3H, t).

Present Compound 1-26
¹H-NMR (CDCl₃) δ: 9.06 (1H, dd), 8.55 (1H, dd), 8.33 (1H, s), 8.12 (1H, d), 7.76 (1H, dd), 7.62 (1H, d), 3.74 (2H, q), 1.41 (3H, t).

Present Compound 1-27
¹H-NMR (CDCl₃) δ: 9.06 (1H, dd), 8.58 (1H, s), 8.54 (1H, dd), 8.44 (1H, d), 8.03 (1H, s), 7.76 (1H, dd), 3.74 (2H, q), 1.41 (3H, t).

Present Compound 1-28
¹H-NMR (CDCl₃) δ: 9.06 (1H, dd), 8.57-8.51 (2H, m), 8.47-8.42 (1H, m), 7.75 (1H, dd), 7.44 (1H, dd), 3.75 (2H, q), 1.41 (3H, t).

Present Compound 1-29
¹H-NMR (CDCl₃) δ: 9.08-9.04 (2H, m), 8.60 (1H, s), 8.55 (1H, dd), 7.79 (1H, dd), 7.75 (1H, dd), 3.75 (2H, q), 1.41 (3H, t).

Present Compound 1-30
¹H-NMR (CDCl₃) δ: 9.64 (1H, d), 9.14 (1H, d), 9.07 (1H, dd), 8.79-8.76 (1H, m), 8.55 (1H, dd), 7.77 (1H, dd), 3.74 (2H, q), 1.42 (314, t).

Present Compound 1-31
¹H-NMR (CDCl₃) δ: 9.07 (1H, dd), 9.04 (1H, d), 8.55 (1H, dd), 8.48 (1H, s), 8.28 (1H, dd), 7.78 (1H, dd), 3.72 (2H, q), 1.42 (3H, t).

Present Compound 1-32
¹H-NMR (CDCl₃) δ: 9.05 (1H, dd), 8.56-8.52 (2H, m), 8.38-8.34 (1H, n), 7.93 (1H, d), 7.74 (1H, dd), 7.66 (1H, did), 3.77 (2H, q), 1.41 (3H, t).

Present Compound 1-33
¹H-NMR (CDCl₃) δ: 9.05 (1H, dd), 8.56-8.51 (2H, m), 8.23 (1H, dd), 7.98 (1H, d), 7.80 (1H, dd), 3.77 (2H, q), 1.40 (3H, t).

Present Compound 1-34
¹H-NMR (CDCl₃) δ: 9.05 (1H, dd), 8.54 (1H, dd), 8.33-8.29 (2H, m), 7.94-7.90 (1H, m), 7.75 (1H, dd), 3.74 (2H, q), 1.41 (3H, t).

Present Compound 1-35
¹H-NMR (CDCl₃) δ: 9.04 (1H, dd), 8.53 (1H, dd), 7.80-7.72 (3H, m), 7.15-7.08 (1H, m), 3.75 (2H, q), 1.40 (3H, t).

Present Compound 1-36
¹H-NMR (CDCl₃) δ: 9.05 (1H, dd), 8.53 (1H, dd), 7.77 (1H, dd), 7.38 (1H, s), 4.41 (3H, s), 3.66 (2H, q), 1.40 (3H, t).

Present Compound 1-37
¹H-NMR (CDCl₃) δ: 9.04 (1H, dd), 8.53 (1H, dd), 7.96 (1H, dd), 7.74 (1H, dd), 7.56 (1H, dd), 3.74 (2H, q), 1.41 (3H, t).

Present Compound 1-38
¹H-NMR (CDCl₃) δ: 9.05 (1H, dd), 8.54 (1H, dd), 8.12 (2H, d), 7.74 (1H, dd), 7.62 (1H, dd), 3.74 (2H, q), 1.41 (3H, t).

Present Compound 1-39
¹H-NMR (CDCl₃) δ: 8.92 (1H, dd), 8.64 (1H, dd), 8.51 (2H, s), 8.05 (1H, s), 7.69 (1H, dd), 4.08 (2H, q), 1.44 (3H, t).

Present Compound 1-41
¹H-NMR (CDCl₃) δ: 9.04 (1H, dd), 8.53 (1H, dd), 7.84 (1H, d), 7.72 (1H, dd), 7.54 (1H, d), 6.19 (2H, s), 3.76 (2H, q), 1.42 (3H, t).

Present Compound 1-42
¹H-NMR (CDCl₃) δ: 9.06 (1H, dd), 6.54 (1H, dd), 8.41 (2H, d) 7.88 (1H, s), 7.75 (1H, dd), 3.74 (2H, q), 1.41 (3H, t).

Present Compound 1-43
¹H-NMR (CDCl₃) δ: 8.91 (1H, dd), 8.63 (1H, dd), 8.22 (2H, t), 7.78 (1H, s), 7.68 (1H, dd), 4.07 (2H, q), 1.43 (3H, t).

Present Compound 1-44
¹H-NMR (CDCl₃) δ: 9.21 (1H, d), 8.91 (1H, dd), 8.64 (1H, dd), 7.71 (1H, dd), 4.00 (2H, q), 1.43 (3H, t).

Present Compound 1-45
¹H-NMR (CDCl₃) δ: 8.90 (1H, td), 8.65 (1H, dt), 8.29 (1H, s), 7.97 (1H, d), 7.71 (1H, ddd), 4.00 (2H, q), 1.43 (3H, t).

Present Compound 1-46
¹H-NMR (CDCl₃) δ: 8.90 (1H, dd), 8.63 (1H, dd), 8.56 (1H, td), 7.67 (1H, dd), 6.81 (1H, d), 4.02 (2H, q), 1.41 (3H, t).

Present Compound 1-47
¹H-NMR (CDCl₃) δ: 8.90 (1H, dd), 8.78 (18, d), 8.62 (1H, dd), 8.00 (1H, s), 7.67 (1H, dd), 4.01 (2H, q), 1.41 (3H, t).

Next, formulation examples of the control agent of the present invention are shown. The part means part by weight.

Formulation Example 1

10 parts of any one of the present compounds 1-1 to 1-47 is dissolved in a mixture of 35 parts of xylene and 35 parts of DMF, 14 parts of polyoxyethylenestyrylphenyl ether and 6 parts of calcium dodecylbenzenesulfonate are added thereto. The mixture is mixed to obtain each emulsifiable concentrate.

Formulation Example 2

4 parts of sodium lauryl sulfate, 2 parts of calcium lignosulfonate, 20 parts of synthetic hydrous silicon oxide fine powder and 54 parts of diatomaceous earth are mixed, and 20 parts of any one of the present compounds 1-1 to 1-47 is further added thereto. The mixture is mixed to obtain each wettable powder.

Formulation Example 3

1 part of synthetic hydrous silicon oxide fine powder, 2 parts of calcium lignosulfonate, 30 parts of bentonite and 65 parts of kaolin clay are added to 2 parts of any one of the present compounds 1-1 to 1-47. Subsequently, an appropriate amount of water is added to this mixture, and the mixture is further stirred, granulated with a granulator, and forced-air dried to obtain each granule.

Formulation Example 4

1 part of any one of the present compounds 1-1 to 1-47 is dissolved in an appropriate amount of acetone, and 5 parts of synthetic hydrous silicon oxide fine powder, 0.3 parts of PAP (isopropyl acid phosphate) and 93.7 parts of Fubasami clay are added thereto. The mixture is sufficiently stirred and mixed to evaporate and eliminate acetone to obtain each powder formulation.

Formulation Example 5

35 parts of a mixture of polyoxyethylene alkyl ether sulfate ammonium salt and white carbon (weight ratio 1:1), 10 parts of any one of the present compounds 1-1 to 1-47 and 55 parts of water are mixed, and finely pulverized by wet grinding method to obtain each flowable.

Formulation Example 6

0.1 parts of any one of the present compounds 1-1 to 1-47 is dissolved in 5 parts of xylene and 5 parts of trichloroethane, and the mixture is mixed with 89.9 parts of deodorized kerosene to obtain each oil solution.

Formulation Example 7

10 mg of any one of the present compounds 1-1 to 1-47 is dissolved in 0.5 ml of acetone, and this solution is applied to 5 g of solid feed powder for animal (solid feed powder for breeding CE-2, product of CLEA Japan, Inc.), and the mixture is uniformly mixed. Subsequently, acetone is evaporated to dryness to obtain each poisonous bait.

Formulation Example 8

0.1 parts of any one of the present compounds 1-1 to 1-47 and 49.9 parts of Neothiozol (Chuo Kasei Co., Ltd.) are filled into an aerosol can, and an aerosol valve is attached, then the container is filled with 25 parts of dimethyl ether and 25 parts of LPG and shaken, and an actuator is attached to obtain an oil-based aerosol.

Formulation Example 9

0.6 parts of any one of the present compounds 1-1 to 1-47, 0.01 parts of BHT (2,6-di-tert-butyl-4-methylphenol), 5 parts of xylene, 3.39 parts of deodorized kerosene and 1 part of emulsifier {RHEODOL MO-60 (manufactured by Kao Corporation)} are mixed and dissolved, and the resulting solution and 50 parts of distilled water are filled into an aerosol container. A valve is attached to the container, then 40 parts of a propellant (LPG) is filled under pressure through the valve to obtain an aqueous aerosol.

Formulation Example 10

0.1 g of any one of the present compounds 1-1 to 1-47 is dissolved in 2 ml of propylene glycol, and the solution is impregnated in a porous ceramic plate with a size of 4.0 cm×4.0 cm and 1.2 cm in thickness to obtain a heating type smoking agent.

Formulation Example 11

5 parts of any one of the present compounds 1-1 to 1-47 and 95 parts of an ethylene-methyl methacrylate copolymer (a ratio of methyl methacrylate in the copolymer: 10% by weight, Acryft WD301, manufactured by Sumitomo Chemical Co., Ltd.) are melt-kneaded with a closed pressurizing kneader (manufactured by Moriyama Works), and the resulting kneaded matter is extruded from a molded matter through a molding die to obtain a rod-shaped molded body with a size of 15 cm in length and 3 mm in diameter.

Formulation Example 12

5 parts of any one of the present compounds 1-1 to 1-47 and 95 parts of a soft vinyl chloride resin are melt-kneaded with a closed pressurizing kneader (manufactured by Moriyama Works), and the resulting kneaded matter is extruded from a molded matter through a molding die to obtain a rod-shaped molded body with a size of 15 cm in length and 3 mm in diameter.

Formulation Example 13

100 mg of any one of the present compounds 1-1 to 1.47, 68.75 mg of lactose, 237.5 mg of corn starch, 43.75 mg of microcrystalline cellulose, 18.75 mg of polyvinylpyrrolidone, 28.75 mg of sodium carboxymethyl starch and 2.5 mg of magnesium stearate are mixed, and the resulting mixture was compressed to an appropriate size to obtain a tablet.

Formulation Example 14

25 mg of any one of the present compounds 1-1 to 1-47, 60 mg of lactose, 25 mg of corn starch, 6 mg of carmellose calcium and an appropriate amount of 5% hydroxypropyl methylcellulose, and the resulting mixture is filled into a hard shell gelatin capsule or a hydroxypropyl methylcellulose capsule to obtain an encapsulated formulation.

Formulation Example 15

Distilled water is added to 1000 mg of any one of the present compounds 1-1 to 1-47, 500 mg of fumaric acid, 2000 mg of sodium chloride, 150 mg of methylparaben, 50 mg of propylparaben, 25000 mg of granulated sugar, 13000 mg of sorbitol (70% solution), 100 mg of Veegum K (Vanderbilt Co.), 35 mg of flavor and 500 mg of colorant, such that a final volume is 100 ml, and the mixture is mixed to obtain a suspension for oral administration.

Formulation Example 16

5% by weight of any one of the present compounds 1-1 to 1-47 is dissolved in 5% by weight of polysorbate 85, 3% by weight of benzyl alcohol and 30% by weight of propylene glycol, and a phosphate buffer is added to this solution so as to have a pH of 6.0 to 6.5, then water is added until it reaches the final volume to obtain a liquid formulation for oral administration.

Formulation Example 17

5% by weight of aluminum distearate is dispersed in 57% by weight of fractionated pain oil and 3% by weight of polysorbate 85 by heating. This dispersion is cooled to room temperature, and 25% by weight of saccharin is dispersed in an oily vehicle thereof. 10% by weight of any one of the present compounds 1-1 to 1-47 is distributed thereto to obtain a paste formulation for oral administration.

Formulation Example 18

5% by weight of any one of the present compounds 1-1 to 1-47 and 95% by weight of limestone filler are mixed, and a granule for oral administration is obtained using wet granulation method.

Formulation Example 19

5 parts of any one of the present compounds 1-1 to 1-47 is dissolved in 80 parts of diethylene glycol monoethyl ether, and 15 parts of propylene carbonate is mixed therewith to obtain a spot-on solution.

Formulation Example 20

10 parts of any one of the present compounds 1-1 to 1-47 is dissolved in 70 parts of diethylene glycol monoethyl ether, and 20 parts of 2-octyl dodecanol is mixed therewith to obtain a pour-on solution.

Formulation Example 21

60 parts of NIKKOL TEALS-42 (Nikko Chemicals Co., Ltd., 42% aqueous solution of triethanolamine lauryl sulfate) and 20 parts of propylene glycol are added to 0.5 parts of any one of the present compounds 1-1 to 1-47, and the mixture is sufficiently stirred and mixed until it becomes a uniform solution, then 19.5 parts of water is added and further sufficiently stirred and mixed to obtain a shampoo agent as a uniform solution.

Formulation Example 22

0.15% by weight of any one of the present compounds 1-1 to 1-47, 95% by weight of an animal feed and 4.85% by weight of a mixture of secondary calcium phosphate, diatomaceous earth, Aerosil and carbonate (or chalk) are sufficiently stirred and mixed to obtain a feed premix for animal.

Formulation Example 23

7.2 g of any one of the present compounds 1-1 to 1-47 and 92.8 g of VOSCO (registered trademark) S-55 (manufactured by Maruishi Pharmaceutical Co., Ltd.) are dissolved and mixed at 100° C., poured into a suppository mold, and cooled and solidified to obtain a suppository.

Next, the arthropod pest control effect of the control agent of the present invention is shown as test examples.

Test Example 1

The formulations of the compounds 1-7, 1-8, 1-15, 1-19, 1-23 to 1-26, 1-28 to 1-30, 1-33 to 1-34, 1-36, 1-38 or 1-42 to 1-43 as obtained in Formulation Example 5 were diluted with water, so as to have a concentration of each compound of 500 ppm, and Sindain (manufactured by Sumitomo Chemical Co., Ltd.) was further added thereto so as to dilute 3000 times to obtain a diluent.

On the other hand, on a cucumber seedling (the first true leaf stage) planted in a plastic cup was inoculated with about 30 *Aphis gossypii* (whole stage), and leaving it for a day. 20 ml of the diluent was sprayed on the seedling.

Six days after spraying, the number of the surviving *Aphis gossypii* parasitic on the leaves of the cucumber was examined, and the control value was calculated according to the following equation:

Control value (%)=(1−($Cb \times Tai$)/($Cai \times Tb$))×100 wherein the symbols represent as follows:
Cb: the number of the insects in a non-treated section before treatment
Cai: the number of the surviving parasitic insects in a non-treated section on observation
Tb: the number of the insects in a treated section before treatment
Tai: the number of the surviving parasitic insects in a treated section on observation
wherein the non-treated section refers to a section where a liquid prepared by diluting the formulation not containing the present compound in Formulation Example 5 with the same amount of water as in the treated section was sprayed.

As a result, in the treated sections of the compounds 1-7, 1-8, 1-15, 1-19, 1-23 to 1-26, 1-28 to 1-30, 1-33 to 1-34, 1-36, 1-38 or 1-42 to 1-43, the control value was each 90% or more.

Test Example 2

The formulations of the compound 1-24 as obtained in Formulation Example 5 was diluted with water, so as to have a concentration of each compound of 500 ppm, to obtain a diluent.

On the other hand, a cucumber seedling (the second true leaf stage) planted in a plastic cup was drenched at its foot with 5 ml of the diluent, and kept in a greenhouse at 25° C. for 7 days. On the cucumber leaf surface was inoculated about 30 *Aphis gossypii* (whole stage), and further kept in the greenhouse for 6 days, then the number of the surviving *Aphis gossypii* parasitic on the leaves of the cucumber was examined, and the control value was calculated according to the following equation:

Control value (%)=(1−($Cb \times Tai$)/($Cai \times Tb$))×100 wherein the symbols represent as follows:
Cb: the number of the insects in a non-treated section on inoculating insects
Cai: the number of the surviving parasitic insects in a non-treated section on observation
Tb: the number of the insects in a treated section on inoculating insects
Tai: the number of the surviving parasitic insects in a treated section on observation
wherein the non-treated section refers to a section where a liquid prepared by diluting the formulation not containing the present compound in Formulation Example 5 with the same amount of water as in the treated section was sprayed.

As a result, in the treated-section of the compound 1-24, the controlling value was 90% or more.

Test Example 3

The formulations of the compounds as obtained in Formulation Example 5 are diluted with water, so as to have a concentration of the compound of 500 ppm, and Sindain (manufactured by Sumitomo Chemical Co., Ltd.) is further added thereto so as to dilute 3000 times to obtain a diluent.

On a rice seedling in the second leaf stage planted in a polyethylene cup is sprayed 10 ml of the diluent. After air-drying, 20 third instar larvae of *Nilaparvata lugens* are released, and kept in the greenhouse at 25° C. After 6 days, the number of surviving *Nilaparvata lugens* parasitic on the rice is examined, and the death rate is calculated according to the following equation:

Death rate (%)=(1−Surviving insects/20)×100 wherein the non-treated section refers to a section where a liquid prepared by diluting the formulation not containing the present compound in Formulation Example 5 with the same amount of water as in the treated section was sprayed.

As a result, in the treated-section of the present compound, a control effect is recognized.

Test Example 4

The formulation of the compound 1-15 as obtained in Formulation Example 5 was diluted with water, so as to have a concentration of the compound of 500 ppm, to obtain a diluent.

On the other hand, a rice seedling (2 weeks after sowing, the second leaf stage) planted in a plastic cup was drenched at its foot with 5 ml of the diluent, and kept in a greenhouse at 25° C. for 7 days. 20 third instar larvae of *Nilaparvata lugens* were released, and further kept in the greenhouse for 6 days, then the number of surviving *Nilaparvata lugens* parasitic on the rice was examined, and the death rate was calculated according to the following equation:

Death rate (%)=(1−Surviving insects/20)×100 wherein the non-treated section refers to a section where a liquid prepared by diluting the formulation not containing the present compound in Formulation Example 5 with the same amount of water as in the treated section was sprayed.

As a result, in the treated-section of the compound 1-15, the death rate was 90% or more.

Test Example 5

The formulations of the compounds as obtained in Formulation Example 5 are diluted with water, so as to have a concentration of the compound of 500 ppm, and Sindain (manufactured by Sumitomo Chemical Co., Ltd.) is further added thereto so as to dilute 3000 times to obtain a diluent.

On the other hand, *Bemisia tabaci* adult is released on a tomato seedling (the third true leaf stage) planted in a polyethylene cup, and made to lay eggs for about 72 hours. The tomato seedling is kept in a greenhouse for 8 days, and when instar larvae hatches from the eggs, the diluent is sprayed at a rate of 20 mil/cup, and the cup is kept in a greenhouse at 25° C. After 7 days, the number of surviving instar larvae on the tomato leaves is examined, and the controlling value is calculated according to the following equation:

Control value (%)={1−(Cb×Tai)/(Cai×Tb)}×100 wherein the symbols represent as follows:

Cb: the number of the instar larvae in a non-treated section before treatment

Cai: the number of the surviving instar larvae in a non-treated section on observation Tb: the number of the instar larvae in a treated section before treatment Tai: the number of the surviving instar larvae in a treated section on observation wherein the non-treated section refers to a section where a liquid prepared by diluting the formulation not containing the present compound in Formulation Example 5 with the same amount of water as in the treated section was sprayed.

As a result, in the treated-section of the present compound, a control effect is recognized.

Test Example 6

The formulations of the present compounds 1-5, 1-8, 1-11 to 1-16, 1-19, 1-21 to 1-22, 1-24 to 1-25, 1-33 to 1-36, 1-38 to 1-39, 1-42 to 1-43 or 1-46 to 1-47 as obtained in Formulation Example 5 were diluted with water, so as to have a concentration of each compound of 500 ppm, and Sindain (manufactured by Sumitomo Chemical Co., Ltd.) was further added thereto so as to dilute 3000 times to obtain a diluent.

On the other hand, on cabbage at the third leaf stage planted in a polyethylene cup was sprayed at a rate of 20 mL/cup of the diluent. After spraying, the plant was air-dried, and the foliage part was cut off, and placed in a 50 mL volume cup. Five second instar larvae of *Plutella xylostella* were released into the cup, and the cup was sealed with a lid.

After the cup was kept at 25° C. for 5 days, the number of dead insects was counted. The death rate was calculated according to the following equation:

Death rate (%)=((Number of tested insects−Number of surviving insects)/Number of tested insects)×100

As a result, in the treated sections of the compounds 1-5, 1-8, 1-11 to 1-16, 1-19, 1-21 to 1-22, 1-24 to 1-25, 1-33 to 1-36, 1-38 to 1-39, 1-42 to 1-43 or 1-46 to 1-47, the death rate was each 680 or more.

Test Example 7

The formulations of the compounds 1-4 to 1-5, 1-7 to 1-8, 1-11 to 1-16, 1-19 to 1-21 or 1-23 to 1-25 as obtained in Formulation Example 5 were diluted with water, so as to have a concentration of each compound of 500 ppm, and Sindain (manufactured by Sumitomo Chemical Co., Ltd.) was further added thereto so as to dilute 3000 times to obtain a diluent. On the other hand, an apple tree was planted in a plastic cup, and grown until the seventh-eighth true leaf was spread. To the apple tree was sprayed at a rate of 20 mL/cup of the diluent. After spraying, the plant was air-dried, 60 first-instar *Adoxophyes orana fasciata* were released, and the plastic cup the bottom of which was cut off and on which a filter paper was put was upside-down and covered. After 7 days, the number of dead insects was counted, and the death rate was calculated according to the following equation:

Death rate (%)=((Number of tested insects−Number of surviving insects)/Number of tested insects)×100

As a result, in the treated sections of the compounds 1-4 to 1-5, 1-7 to 1-8, 1-11 to 1-16, 1-19 to 1-21 or 1-23 to 1-25, the death rate was each 90% or more.

Test Example 8

The formulations of the present compounds as obtained in Formulation Example 5 are diluted with water, so as to have a concentration of the compound of 500 ppm, to obtain a diluent. A filter paper having a diameter of 5.5 cm is spread on the bottom of a polyethylene cup having the same diameter and 0.7 ml of the diluent is added dropwise onto the filter paper, and 30 mg of sucrose is uniformly placed as bait. Into the polyethylene cup, 10 female imagoes of *Musca domestica* are released, and the cup is sealed with a lid. After 24 hours, the life and death of *Musca domestica* is examined, the number of dead insects was counted, and the death rate is calculated according to the following equation.

Death rate (%)=(Number of dead insects/Number of tested insects)×100

As a result, in the treated-section of the present compound, a control effect is recognized.

Test Example 9

The formulation of the compound 1-6 or 1-24 as obtained in Formulation Example 5 was diluted with water, so as to have a concentration of each compound of 500 ppm, to obtain a diluent.

A filter paper having a diameter of 5.5 cm was spread on the bottom of a polyethylene cup having the same diameter and 0.7 ml of the diluent was added dropwise onto the filter paper, and 30 mg of sucrose was uniformly placed as bait.

Into the polyethylene cup, 2 male imagoes of *Blattella germanica* were released, and the cup was sealed with a lid. After 6 days, the life and death of *Blattella germanica* was examined, the number of dead insects was counted, and the death rate was calculated according to the following equation.

Death rate (%)=(Number of dead insects/Number of tested insects)×100

As a result, in the treated-section of the compound 1-6 or 1-24, the death rate was each 100%.

Test Example 10

The formulations of the compounds 1-13, 1-15, 1-19, 1-24 to 1-25, 1-39, or 1-42 to 1-43 as obtained in Formulation Example 5 were diluted with water, so as to have a concentration of each compound of 500 ppm, to obtain a diluent.

0.7 ml of the diluent was added to 100 ml of ion-exchanged water (active ingredient concentration: 3.5 ppm). 20 last-instar larvae of *Culex pipiens pallens* were released into the solution. One day later, the life and death of the *Culex pipiens pallens* was examined, and the number of dead insects was counted to calculate the death rate.

Death rate (%)=(Number of dead insects/Number of tested insects)×100

As a result, in the treated sections of the compounds 1-13, 1-15, 1-19, 1-24 to 1-25, 1-39, or 1-42 to 1-43, the death rate was each 95% or more.

Test Example 11

2 mg of each of the compounds 1-6, 1-10, 1-15, 1-24 or 1-37 to 1-38 was weighed in a screw tube (Maruemu No. 5; 27×55 mm), and 0.2 mL of acetone was added thereto and sealed with a cap to dissolve the compound. The screw tube was rotated and inverted to uniformly coat the liquid onto the whole inner wall of the tube. After removing the cap, the solution was air-dried for about 2 hours, then non-blood-sucking nymphal ticks, *Haemaphysalis longicornis* (5 ticks/group) were released, and the tube was sealed with the cap. After 2 days, the number of dead insects was counted, and the death rate was calculated according to the following equation:

Death rate (%)=100×(Number of dead insects/Number of tested insects)

As a result, in the treated sections of the compounds 1-6, 1-10, 1-15, 1-24 or 1-37 to 1-38, the death rate was each 100%.

Test Example 12

The formulations of the compounds 1-15, 1-19, 1-25, 1-39, 1-42 or 1-44 to 1-45 as obtained in Formulation Example 1 were diluted with water, so as to have a concentration of the compound of 500 ppm, and Sindain (manufactured by Sumitomo Chemical Co., Ltd.) was further added thereto so as to dilute 3000 times to obtain a diluent.

On the other hand, on cucumber at the third leaf stage planted in a polyethylene cup was sprayed at a rate of 30 mL/cup of the diluent. After spraying, the plant was air-dried, and the second leaf was cut off and then placed in a 200 mL volume cup. Ten second instar larvae of *Aulacophora femoralis* were released into the cup, and the cup was sealed with a lid. After the cup was kept at 25° C. for 5 days, the number of dead insects was counted. The death rate was calculated according to the following equation:

Death rate (%)=(Number of dead insects/Number of tested insects)×100

As a result, in the treated sections of the compounds 1-15, 1-19, 1-25, 1-39, 1-42 or 1-44 to 1-45, the death rate was each 80% or more.

Test Example 13

The formulations of the present compounds as obtained in Formulation Example 1 are diluted with water, so as to have a concentration of the compound of 500 ppm, to obtain a diluent.

On the other hand, artificial feed for *Diabrotica virgifera virgifera* is prepared according to the procedures of Pleau, et al. (Entomologia Experimentalis et Applicata 105: 1-11, 2002), and 2 mL is put in each well of a 24-well microplate (manufactured by Becton Dickinson). The diluent is sprayed on the surface of the artificial feed at a rate of 40 µL/well, and after the artificial feed is dried, five first-instar *Diabrotica virgifera virgifera* are released per 1 well, and the well is sealed by being covered with parafilm (manufactured by Bemis Company, Inc.). The cup is kept at 25° C., and after 3 days of treatment, the number of dead insects is counted. The death rate is calculated according to the following equation:

Death rate (%)=(Number of dead insects/Number of tested insects)×100

As a result, in the treated-section of the present compound, a control effect is recognized.

INDUSTRIAL APPLICABILITY

The control agent of the present invention has a controlling effect on arthropod pests and is useful as an active ingredient of an arthropod pest control agent.

The invention claimed is:
1. An arthropod pest control agent comprising an inert carrier and a diaryl-azole compound represented by formula (1):

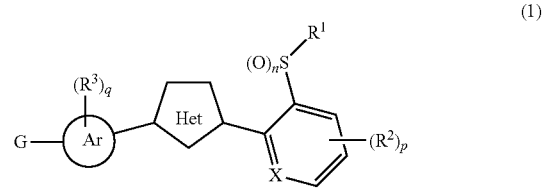

or an N-oxide thereof,
wherein
X represents a nitrogen atom,
R$^1$ represents a C1 to C6 chain hydrocarbon group optionally substituted with one or more atoms or groups selected from group α,
R$^2$ and R$^3$ independently represent a C1 to C6 chain hydrocarbon group optionally substituted with one or more atoms or groups selected from group α, a C3 to C9 alicyclic hydrocarbon group optionally substituted with one or more atoms or groups selected from group β, a phenyl group optionally substituted with one or more atoms or groups selected from group γ, a 5- or 6-membered heterocyclic group optionally substituted with one or more atoms or groups selected from group γ, C(O)R$^5$, C(O)OR$^5$, C(O)NR$^5$R$^6$, OR$^5$, SR$^5$, S(O)$_r$R$^{5x}$, S(O)$_2$NR$^5$R$^6$, NR$^5$R$^6$, NR$^5$C(O)R$^6$, NR$^5$C(O)OR$^6$, a nitro group, a cyano group, or a halogen atom, R$^5$ and R$^6$ independently represent a C1 to C6 chain hydrocarbon group optionally substituted with one or more atoms or groups selected from group α, a C3 to C9 alicyclic hydrocarbon group optionally substituted with one or more atoms or groups selected from group β, a phenyl group optionally substituted with one or more atoms or groups selected from group γ, a 5- or 6-membered heterocyclic group optionally substituted with one or more atoms or groups selected from group γ, or a hydrogen atom, R$^{5x}$ represents a C1 to C6 chain hydrocarbon group optionally substituted with one or more atoms or groups selected from group α, a C3 to C9 alicyclic hydrocarbon group optionally substituted with one or more atoms or groups selected from group β, a phenyl group optionally substituted with one or more atoms or groups selected from group γ, or a 5- or 6-membered heterocyclic group optionally substituted with one or more atoms or groups selected from group γ, Het represents the following formula H2:

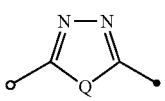

(H2)

wherein Q represents an oxygen atom or a sulfur atom,

Ar represents a phenyl group,

G represents a C1 to C6 chain hydrocarbon group optionally substituted with one or more halogen atoms, or a C3 to C6 alicyclic hydrocarbon group optionally substituted with one or more halogen atoms, n represents 0, 1, or 2, m represents 0, 1, or 2, r represents 1 or 2, p represents 0, 1, 2, or 3, and when p represents 2 or 3, each R$^2$ can be the same or different, and q represents 0, 1, 2, 3, or 4, and when q represents 2, 3, or 4, each R$^3$ can be the same or different, Group α is selected from the group consisting of a C1 to C6 alkoxy group optionally substituted with one or more halogen atoms, a C2 to C6 alkenyloxy group optionally substituted with one or more halogen atoms, a C2 to C6 alkynyloxy group optionally substituted with one or more halogen atoms, a C1 to C6 alkylsulfanyl group optionally substituted with one or more halogen atoms, a C1 to C6 alkylsulfinyl group optionally substituted with one or more halogen atoms, a C1 to C6 alkylsulfonyl group optionally substituted with one or more halogen atoms, a C2 to C6 alkylcarbonyl group optionally substituted with one or more halogen atoms, a C2 to C6 alkoxycarbonyl group optionally substituted with one or more halogen atoms, a C3 to C6 cycloalkyl group optionally substituted with one or more halogen atoms or one or more C1 to C3 alkyl groups, a cyano group, a hydroxy group, and a halogen atom, Group β is selected from the group consisting of a C1 to C6 chain hydrocarbon group optionally substituted with one or more halogen atoms, a C1 to C6 alkoxy group optionally substituted with one or more halogen atoms, a C2 to C6 alkenyloxy group optionally substituted with one or more halogen atoms, a C2 to C6 alkynyloxy group optionally substituted with one or more halogen atoms, and a halogen atom, and Group γ is selected from the group consisting of a C1 to C6 chain hydrocarbon group optionally substituted with one or more halogen atoms, a C1 to C6 alkoxy group optionally substituted with one or more halogen atoms, a C1 to C6 alkylsulfanyl group optionally substituted with one or more halogen atoms, a C1 to C6 alkylsulfinyl group optionally substituted with one or more halogen atoms, a C1 to C6 alkylsulfonyl group optionally substituted with one or more halogen atoms, a C2 to C6 alkylcarbonyl group optionally substituted with one or more halogen atoms, a C2 to C6 alkoxycarbonyl group optionally substituted with one or more halogen atoms, a C1 to C6 alkylamino group optionally substituted with one or more halogen atoms, a C2 to C8 dialkylamino group optionally substituted with one or more halogen atoms, a halogen atom, a cyano group, and a nitro group.

2. The arthropod pest control agent according to claim 1, wherein Q is an oxygen atom.

3. The arthropod pest control agent according to claim 1, wherein Q is a sulfur atom.

4. A diaryl-azole compound represented by formula (1):

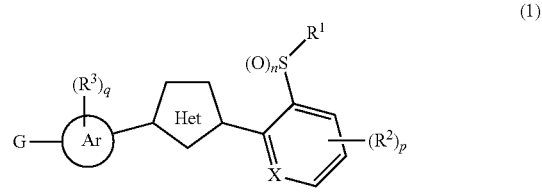

(1)

or an N-oxide thereof, wherein

X represents a nitrogen atom,

R$^1$ represents a C1 to C6 chain hydrocarbon group optionally substituted with one or more atoms or groups selected from group α, R$^2$ and R$^3$ independently represent a C1 to C6 chain hydrocarbon group optionally substituted with one or more atoms or groups selected from group α, a C3 to C9 alicyclic hydrocarbon group optionally substituted with one or more atoms or groups selected from group β, a phenyl group optionally substituted with one or more atoms or groups selected from group γ, a 5- or 6-membered heterocyclic group optionally substituted with one or more atoms or groups selected from group γ, C(O)R$^5$, C(O)OR$^5$, C(O)NR$^5$R$^6$, OR$^5$, SR$^5$, S(O)$_r$R$^{5x}$, S(O)$_2$NR$^5$R$^6$, NR$^5$R$^6$, NR$^5$C(O)R$^6$, NR$^5$C(O)OR$^6$, a nitro group, a cyano group, or a halogen atom, R$^5$ and R$^6$ independently represent a C1 to C6 chain hydrocarbon group optionally substituted with one or more atoms or groups selected from group α, a C3 to C9 alicyclic hydrocarbon group optionally substituted with one or more atoms or groups selected from group β, a phenyl group optionally substituted with one or more atoms or groups selected from group γ, a 5- or 6-membered heterocyclic group optionally substituted with one or more atoms or groups selected from group γ, or a hydrogen atom, $R^{5x}$ represents a C1 to C6 chain hydrocarbon group optionally substituted with one or more atoms or groups selected from group α, a C3 to C9 alicyclic hydrocarbon group optionally substituted with one or more atoms or groups selected from group β, a phenyl group optionally substituted with one or more atoms or groups selected from group γ, or a 5- or 6-membered heterocyclic group optionally substituted with one or more atoms or groups selected from group γ, Het represents the following formula H2:

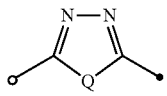

(H2)

wherein Q represents an oxygen atom or a sulfur atom,

Ar represents a phenyl group,

G represents a C1 to C6 chain hydrocarbon group optionally substituted with one or more halogen atoms, or a C3 to C6 alicyclic hydrocarbon group optionally substituted with one or more halogen atoms, n represents 0, 1, or 2, m represents 0, 1, or 2, r represents 1 or 2, p represents 0, 1, 2, or 3, and when p represents 2 or 3, each $R^2$ can be the same or different, and q represents 0, 1, 2, 3, or 4, and when q represents 2, 3, or 4, each $R^3$ can be the same or different, Group α is selected from the group consisting of a C1 to C6 alkoxy group optionally substituted with one or more halogen atoms, a C2 to C6 alkenyloxy group optionally substituted with one or more halogen atoms, a C2 to C6 alkynyloxy group optionally substituted with one or more halogen atoms, a C1 to C6 alkylsulfanyl group optionally substituted with one or more halogen atom, a C1 to C6 alkylsulfinyl group optionally substituted with one or more halogen atoms, a C1 to C6 alkylsulfonyl group optionally substituted with one or more halogen atoms, a C2 to C6 alkylcarbonyl group optionally substituted with one or more halogen atoms, a C2 to C6 alkoxycarbonyl group optionally substituted with one or more halogen atoms, a C3 to C6 cycloalkyl group optionally substituted with one or more halogen atoms or one or more C1 to C3 alkyl groups, a cyano group, a hydroxy group, and a halogen atom, Group β is selected from the group consisting of a C1 to C6 chain hydrocarbon group optionally substituted with one or more halogen atoms, a C1 to C6 alkoxy group optionally substituted with one or more halogen atoms, a C2 to C6 alkenyloxy group optionally substituted with one or more halogen atoms, a C2 to C6 alkynyloxy group optionally substituted with one or more halogen atoms, and a halogen atom, and Group γ is selected from the group consisting of a C1 to C6 chain hydrocarbon group optionally substituted with one or more halogen atoms, a C1 to C6 alkoxy group optionally substituted with one or more halogen atoms, a C1 to C6 alkylsulfanyl group optionally substituted with one or more halogen atoms, a C1 to C6 alkylsulfinyl group optionally substituted with one or more halogen atoms, a C1 to C6 alkylsulfonyl group optionally substituted with one or more halogen atoms, a C2 to C6 alkylcarbonyl group optionally substituted with one or more halogen atoms, a C2 to C6 alkoxycarbonyl group optionally substituted with one or more halogen atoms, a C1 to C6 alkylamino group optionally substituted with one or more halogen atoms, a C2 to C8 dialkylamino group optionally substituted with one or more halogen atoms, a halogen atom, a cyano group, and a nitro group.

5. The diaryl-aryl azole compound of formula (1) according to claim 4, wherein $R^1$ is $CH_2CH_3$.

6. A method for controlling arthropod pests comprising applying an effective amount of an arthropod pest control agent comprising an inert carrier and a diaryl-azole compound represented by formula (1):

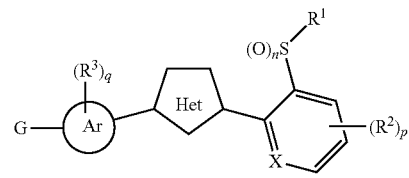

(1)

or an N-oxide thereof, to an arthropod pest or an arthropod pest-infested area, wherein X represents a nitrogen atom or $CR^4$, $R^1$ represents a C1 to C6 chain hydrocarbon group optionally substituted with one or more atoms or groups selected from group α, $R^2$ and $R^3$ independently represent a C1 to C6 chain hydrocarbon group optionally substituted with one or more atoms or groups selected from group α, a C3 to C9 alicyclic hydrocarbon group optionally substituted with one or more atoms or groups selected from group β, a phenyl group optionally substituted with one or more atoms or groups selected from group γ, a 5- or 6-membered heterocyclic group optionally substituted with one or more atoms or groups selected from group γ, $C(O)R^5$, $C(O)OR^5$, $C(O)NR^5R^6$, $OR^5$, $SR^5$, $S(O)_rR^{5x}$, $S(O)_2NR^5R^6$, $NR^5R^6$, $NR^5C(O)R^6$, $NR^5C(O)OR^6$, a nitro group, a cyano group, or a halogen atom, $R^4$ represents a C1 to C6 chain hydrocarbon group optionally having one or more atoms or groups selected from group α, a C3 to C9 alicyclic hydrocarbon group optionally having one or more atoms or groups selected from group β, a phenyl group optionally having one or more atoms or groups selected from group γ, a 5- or 6-membered heterocyclic group optionally having one or more atoms or groups selected from group γ, $C(O)R^5$, $C(O)OR^5$, $C(O)NR^5R^6$, $OR^5$, $SR^5$, $S(O)_rR^{5x}$, $S(O)_2NR^5R^6$, $NR^5R^6$, $NR^5C(O)R^6$, $NR^5C(O)OR^6$, a nitro group, a cyano group, a halogen atom, or a hydrogen atom, $R^5$ and $R^6$ independently represent a C1 to C6 chain hydrocarbon group optionally substituted with one or more atoms or groups selected from group α, a C3 to C9 alicyclic hydrocarbon group optionally substituted with one or more atoms or groups selected from group β, a phenyl group optionally substituted with one or more atoms or groups selected from group γ, a 5- or 6-membered heterocyclic group optionally substituted with one or more atoms or groups selected from group γ, or a hydrogen atom, R$^{5x}$ represents a C1 to C6 chain hydrocarbon group optionally substituted with one or more atoms or groups selected from group α, a C3 to C9 alicyclic hydrocarbon group optionally substituted with one or more atoms or groups selected from group β, a phenyl group optionally substituted with one or more atoms or groups selected from group γ, or a 5- or 6-membered heterocyclic group optionally substituted with one or more atoms or groups selected from group γ, Het represents the following formula H2:

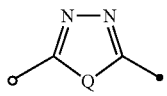

(H2)

wherein Q represents an oxygen atom or a sulfur atom,

Ar represents a phenyl group,

G represents a C1 to C6 chain hydrocarbon group optionally substituted with one or more halogen atoms, or a C3 to C6 alicyclic hydrocarbon group optionally substituted with one or more halogen atoms, n represents 0, 1, or 2, m represents 0, 1, or 2, r represents 1 or 2, p represents 0, 1, 2, or 3, and when p represents 2 or 3, each R$^2$ can be the same or different, and q represents 0, 1, 2, 3, or 4, and when q represents 2, 3, or 4, each R$^3$ can be the same or different, Group α is selected from the group consisting of a C1 to C6 alkoxy group optionally substituted with one or more halogen atoms, a C2 to C6 alkenyloxy group optionally substituted with one or more halogen atoms, a C2 to C6 alkynyloxy group optionally substituted with one or more halogen atoms, a C1 to C6 alkylsulfanyl group optionally substituted with one or more halogen atom, a C1 to C6 alkylsulfinyl group optionally substituted with one or more halogen atoms, a C1 to C6 alkylsulfonyl group optionally substituted with one or more halogen atoms, a C2 to C6 alkylcarbonyl group optionally substituted with one or more halogen atoms, a C2 to C6 alkoxycarbonyl group optionally substituted with one or more halogen atoms, a C3 to C6 cycloalkyl group optionally substituted with one or more halogen atoms or one or more C1 to C3 alkyl groups, a cyano group, a hydroxy group, and a halogen atom, and Group β is selected from the group consisting of a C1 to C6 chain hydrocarbon group optionally substituted with one or more halogen atoms, a C1 to C6 alkoxy group optionally substituted with one or more halogen atoms, a C2 to C6 alkenyloxy group optionally substituted with one or more halogen atoms, a C2 to C6 alkynyloxy group optionally substituted with one or more halogen atoms, and a halogen atom, and Group γ is selected from the group consisting of a C1 to C6 chain hydrocarbon group optionally substituted with one or more halogen atoms, a C1 to C6 alkoxy group optionally substituted with one or more halogen atoms, a C1 to C6 alkylsulfanyl group optionally substituted with one or more halogen atoms, a C1 to C6 alkylsulfinyl group optionally substituted with one or more halogen atoms, a C1 to C6 alkylsulfonyl group optionally substituted with one or more halogen atoms, a C2 to C6 alkylcarbonyl group optionally substituted with one or more halogen atoms, a C2 to C6 alkoxycarbonyl group optionally substituted with one or more halogen atoms, a C1 to C6 alkylamino group optionally substituted with one or more halogen atoms, a C2 to C8 dialkylamino group optionally substituted with one or more halogen atoms, a halogen atom, a cyano group, and a nitro group.

7. A method for controlling arthropod pests comprising applying an effective amount of the arthropod pest control agent according to claim 1 to an arthropod pest or an arthropod pest-infested area.

8. A method for controlling arthropod pests comprising applying an effective amount of a diaryl-azole compound represented by formula (1):

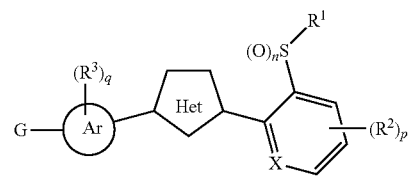

(1)

or an N-oxide thereof, to an arthropod pest or an arthropod pest-infested area, wherein X represents a nitrogen atom or CR$^4$, R$^1$ represents a C1 to C6 chain hydrocarbon group optionally substituted with one or more atoms or groups selected from group α, R$^2$ and R$^3$ independently represent a C1 to C6 chain hydrocarbon group optionally substituted with one or more atoms or groups selected from group α, a C3 to C9 alicyclic hydrocarbon group optionally substituted with one or more atoms or groups selected from group β, a phenyl group optionally substituted with one or more atoms or groups selected from group γ, a 5- or 6-membered heterocyclic group optionally substituted with one or more atoms or groups selected from group γ, C(O)R$^5$, C(O)OR$^5$, C(O)NR$^5$R$^6$, OR$^5$, SR$^5$, S(O)$_r$R$^{5x}$, S(O)$_2$NR$^5$R$^6$, NR$^5$R$^6$, NR$^5$C(O)R$^6$, NR$^5$C(O)OR$^6$, a nitro group, a cyano group, or a halogen atom, R$^4$ represents a C1 to C6 chain hydrocarbon group optionally having one or more atoms or groups selected from group α, a C3 to C9 alicyclic hydrocarbon group optionally having one or more atoms or groups selected from group β, a phenyl group optionally having one or more atoms or groups selected from group γ, a 5- or 6-membered heterocyclic group optionally having one or more atoms or groups selected from group γ, C(O)R$^5$, C(O)OR$^5$, C(O)NR$^5$R$^6$, OR$^5$, SR$^5$, S(O)$_r$R$^{5x}$, S(O)$_2$NR$^5$R$^6$, NR$^5$R$^6$, NR$^5$C(O)R$^6$, NR$^5$C(O)OR$^6$, a nitro group, a cyano group, a halogen atom, or a hydrogen atom, R$^5$ and R$^6$ independently represent a C1 to C6 chain hydrocarbon group optionally substituted with one or more atoms or groups selected from group α, a C3 to C9 alicyclic hydrocarbon group optionally substituted with one or more atoms or groups selected from group β, a phenyl group optionally substituted with one or more atoms or groups selected from group γ, a 5- or 6-membered heterocyclic group optionally substituted with one or more atoms or groups selected from group γ, or a hydrogen atom, $R^{5x}$ represents a C1 to C6 chain hydrocarbon group optionally substituted with one or more atoms or groups selected from group α, a C3 to C9 alicyclic hydrocarbon group optionally substituted with one or more atoms or groups selected from group β, a phenyl group optionally substituted with one or more atoms or groups selected from group γ, or a 5- or 6-membered heterocyclic group optionally substituted with one or more atoms or groups selected from group γ, Het represents the following formula H2:

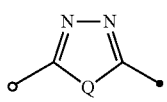

(H2)

wherein Q represents an oxygen atom or a sulfur atom,

Ar represents a phenyl group,

G represents a C1 to C6 chain hydrocarbon group optionally substituted with one or more halogen atoms, or a C3 to C6 alicyclic hydrocarbon group optionally substituted with one or more halogen atoms, n represents 0, 1, or 2, m represents 0, 1, or 2, r represents 1 or 2, p represents 0, 1, 2, or 3, and when p represents 2 or 3, each $R^2$ can be the same or different, and q represents 0, 1, 2, 3, or 4, and when q represents 2, 3, or 4, each $R^3$ can be the same or different, Group α is selected from the group consisting of a C1 to C6 alkoxy group optionally substituted with one or more halogen atoms, a C2 to C6 alkenyloxy group optionally substituted with one or more halogen atoms, a C2 to C6 alkynyloxy group optionally substituted with one or more halogen atoms, a C1 to C6 alkylsulfanyl group optionally substituted with one or more halogen atom, a C1 to C6 alkylsulfinyl group optionally substituted with one or more halogen atoms, a C1 to C6 alkylsulfonyl group optionally substituted with one or more halogen atoms, a C2 to C6 alkylcarbonyl group optionally substituted with one or more halogen atoms, a C2 to C6 alkoxycarbonyl group optionally substituted with one or more halogen atoms, a C3 to C6 cycloalkyl group optionally substituted with one or more halogen atoms or one or more C1 to C3 alkyl groups, a cyano group, a hydroxy group, and a halogen atom, and Group β is selected from the group consisting of a C1 to C6 chain hydrocarbon group optionally substituted with one or more halogen atoms, a C1 to C6 alkoxy group optionally substituted with one or more halogen atoms, a C2 to C6 alkenyloxy group optionally substituted with one or more halogen atoms, a C2 to C6 alkynyloxy group optionally substituted with one or more halogen atoms, and a halogen atom, and Group γ is selected from the group consisting of a C1 to C6 chain hydrocarbon group optionally substituted with one or more halogen atoms, a C1 to C6 alkoxy group optionally substituted with one or more halogen atoms, a C1 to C6 alkylsulfanyl group optionally substituted with one or more halogen atoms, a C1 to C6 alkylsulfinyl group optionally substituted with one or more halogen atoms, a C1 to C6 alkylsulfonyl group optionally substituted with one or more halogen atoms, a C2 to C6 alkylcarbonyl group optionally substituted with one or more halogen atoms, a C2 to C6 alkoxycarbonyl group optionally substituted with one or more halogen atoms, a C1 to C6 alkylamino group optionally substituted with one or more halogen atoms, a C2 to C8 dialkylamino group optionally substituted with one or more halogen atoms, a halogen atom, a cyano group, and a nitro group.

9. A method for controlling arthropod pests comprising applying an effective amount of the diaryl-azole compound of formula (1) according to claim 4 to an arthropod pest or an arthropod pest-infested area.

* * * * *